United States Patent
Jain et al.

(10) Patent No.: US 11,102,304 B1
(45) Date of Patent: Aug. 24, 2021

(54) DELIVERING INFORMATION AND VALUE TO PARTICIPANTS IN DIGITAL CLINICAL TRIALS

(71) Applicant: Vignet Incorporated, Fairfax, VA (US)

(72) Inventors: Praduman Jain, Fairfax, VA (US); James Clive Wade, Pasadena, CA (US); Josh Schilling, Salem, OR (US)

(73) Assignee: Vignet Incorporated, Fairfax, VA (US)

( * ) Notice: Subject to any disclaimer, the term of this patent is extended or adjusted under 35 U.S.C. 154(b) by 0 days.

(21) Appl. No.: 16/881,081

(22) Filed: May 22, 2020

(51) Int. Cl.
*H04L 29/08* (2006.01)

(52) U.S. Cl.
CPC ........ *H04L 67/12* (2013.01); *H04L 29/08972* (2013.01); *H04L 67/327* (2013.01)

(58) Field of Classification Search
CPC .. H04L 67/12; H04L 67/327; H04L 29/08972
See application file for complete search history.

(56) References Cited

U.S. PATENT DOCUMENTS

| | | | |
|---|---|---|---|
| 7,170,993 B2 | 1/2007 | Anderson et al. |
| 8,583,453 B2 | 11/2013 | Plummer et al. |
| 8,684,922 B2 | 4/2014 | Tran |
| 8,706,521 B2 | 4/2014 | Ramarajan et al. |
| 8,707,392 B2 | 4/2014 | Birtwhistle et al. |
| 8,825,775 B2 | 9/2014 | Bohner et al. |
| 9,286,442 B2 | 3/2016 | Csoma et al. |
| 9,361,011 B1 | 6/2016 | Burns |
| 9,426,433 B1 | 8/2016 | Mazzarella |
| 9,461,972 B1 | 10/2016 | Mehta |
| 9,514,655 B1 | 12/2016 | Nusbaum et al. |
| 10,069,934 B2 | 9/2018 | Jain et al. |
| 10,231,622 B2 | 3/2019 | Soyao et al. |
| 10,452,816 B2 | 10/2019 | Kidd et al. |
| 10,546,339 B2 | 1/2020 | Jiao et al. |
| 10,580,531 B2 | 3/2020 | Jiao et al. |
| 10,636,525 B2 | 4/2020 | Jiao et al. |

(Continued)

OTHER PUBLICATIONS

Wilson, David, Eoin McLoughlin, Dympna O'Sullivan, and Michela Bertolotto, "Contextual Media Integration and Recommendation for Mobile Medical Diagnosis", 2006, Springer, pp. 334-337. (Year: 2006).*

(Continued)

*Primary Examiner* — Nam T Tran
(74) *Attorney, Agent, or Firm* — Fish & Richardson P.C.

(57) ABSTRACT

Methods, systems, and apparatus, including computer programs encoded on computer-storage media, for context-based evaluation to enhance the relevance and usefulness of computer system output. In some implementations, a computer system is configured to customize its interactions for a particular situation or user. The system can obtain context information and evaluate the relevance and usefulness of potential outputs and actions with respect to the context indicated by the context information. For example, the system can vary the type and format of output information based on information that describes the intended recipient and the situation of the recipient. The system can take into account many different factors in its evaluation, including timing, user preferences, user history, user classification, impact or effect of the system's decisions on users, and more.

24 Claims, 22 Drawing Sheets

(56) References Cited

U.S. PATENT DOCUMENTS

| | | | |
|---|---|---|---|
| 10,650,474 B2 | 5/2020 | Jiao et al. | |
| 10,672,519 B2 | 6/2020 | Jiao et al. | |
| 2001/0019338 A1 | 9/2001 | Roth | |
| 2002/0022973 A1 | 2/2002 | Sun | |
| 2005/0086587 A1 | 4/2005 | Balz | |
| 2005/0186550 A1 | 8/2005 | Gillani | |
| 2006/0107219 A1 | 5/2006 | Ahya | |
| 2008/0005679 A1* | 1/2008 | Rimas-Ribikauskas | H04L 67/303 715/745 |
| 2008/0127040 A1 | 5/2008 | Barcellona | |
| 2009/0024944 A1 | 1/2009 | Louch | |
| 2009/0043689 A1 | 2/2009 | Yang | |
| 2009/0163182 A1 | 6/2009 | Gatti | |
| 2009/0172002 A1 | 7/2009 | Bathiche | |
| 2010/0041378 A1 | 2/2010 | Aceves | |
| 2011/0200979 A1 | 8/2011 | Benson | |
| 2012/0102050 A1 | 4/2012 | Button | |
| 2012/0272156 A1* | 10/2012 | Kerger | H04M 3/487 715/747 |
| 2013/0110565 A1 | 5/2013 | Means | |
| 2013/0166494 A1 | 6/2013 | Davis | |
| 2013/0238686 A1 | 9/2013 | O'Donoghue | |
| 2013/0326375 A1 | 12/2013 | Barak et al. | |
| 2014/0088995 A1 | 3/2014 | Damani | |
| 2014/0100883 A1 | 4/2014 | Hamilton | |
| 2014/0156823 A1 | 6/2014 | Liu | |
| 2014/0181715 A1* | 6/2014 | Axelrod | G06F 3/0487 715/771 |
| 2014/0240122 A1 | 8/2014 | Roberts | |
| 2014/0273913 A1 | 9/2014 | Michel | |
| 2014/0278474 A1 | 9/2014 | McClure et al. | |
| 2015/0088955 A1 | 3/2015 | Hendrick et al. | |
| 2015/0135160 A1 | 5/2015 | Gauvin | |
| 2015/0148061 A1 | 5/2015 | Koukoumidis | |
| 2016/0058287 A1 | 3/2016 | Dyell | |
| 2016/0086505 A1 | 3/2016 | Hanlon | |
| 2016/0300570 A1 | 10/2016 | Gustafson et al. | |
| 2016/0342906 A1* | 11/2016 | Shaashua | H04L 67/12 |
| 2016/0358479 A1* | 12/2016 | Riedelsheimer | H04L 67/12 |
| 2017/0118159 A1 | 4/2017 | Ratiu et al. | |
| 2017/0155737 A1* | 6/2017 | Jannink | H04L 67/327 |
| 2017/0235912 A1 | 8/2017 | Moturu et al. | |
| 2018/0025125 A1 | 1/2018 | Crane et al. | |
| 2018/0089568 A1* | 3/2018 | Allen | G06N 5/04 |
| 2018/0176331 A1 | 6/2018 | Jain et al. | |
| 2018/0295013 A1* | 10/2018 | Deb | H04L 41/16 |
| 2018/0365028 A1 | 12/2018 | Hosabettu | |
| 2019/0002982 A1 | 1/2019 | Wang | |
| 2019/0068753 A1 | 2/2019 | Jain et al. | |
| 2019/0122266 A1 | 4/2019 | Ramer et al. | |
| 2019/0140892 A1 | 5/2019 | Jain et al. | |
| 2020/0106841 A1* | 4/2020 | Delaney | H04L 67/12 |

OTHER PUBLICATIONS

Cleveland Clinic, "Office of the Patient Experience Newsletter—Spring 2010," May 26, 2010, retrieved at URL<https://my.clevelandclinic.org/ccf/media/files/Patient-Experience/OPE-Newsletter-5-26-10>, 16 pages.

Cleveland Clinic, "The Center for Excellence in Healthcare Communication Overview," Sep. 26, 2013, retrieved at URL<https://my.clevelandclinic.org/ccf/media/Files/Patient-Experience/cehc-overview.pdf>, 12 pages.

Crockett, "The Patient Experience is Critical," Verge Health, Feb. 2017, retrieved at URL<https://www.vergehealth.com/news/media-hits/patient-experience-clinical/>, 3 pages.

HealthcareSuccess.com, "At Cleveland Clinic, Patient Experience is Not Just About Patient Satisfaction," Oct. 7, 2019, retrieved form URL<https://healthcaresuccess.com/blog/podcast-interview/at-cleveland-clinic-patient-experience-is-not-about-patient-satisfaction.html>, 15 pages.

KhanAcademic.org, 2017, retrieved at URL<http://www.khanacademic.org>, 1 page.

National Research Council, "The Role of Human Factors in Home Health Care: Workshop Summary," 2010, Chapter 8, 35 pages.

Sofian et al., "Online Peer Coaching Integrated with Multiple Interventions to Extend DM Effectiveness," The NewSof Group, Inc., 2007, 21 pages.

Sofian et al., "Strengthen Context to Enhance Health Promotion Effectiveness,"American Journal of Health Promotion, Mar./Apr. 2003, 17(4):1-9.

* cited by examiner

| Criteria | Information | Question(s) if Information Unavailable | At Risk Scoring Criteria (formula) | Adjusted Score based on MoM (formula) | Weighting if at Risk (weighting) |
|---|---|---|---|---|---|
| 1 | Current Mood | Scoring Questionnaire (resource) | Value <> Risk Limit, then lookup risk score | If Age <> Age Limit, then <adjust> risk by <value>; Additional conditions | Based on risk value, select weight factor (e.g. 10) |
| 2 | Current Allergies | Enter current allergies and sensitivity, use allergy lookup table (resource) | Value <> Risk, then lookup score | If Sex at Birth <> Male or Female, then <adjust> risk by <value> | Based on risk value, select weight factor (e.g. 5) |
| 3 | Current Medications | Enter current medications and quantities, use medication lookup table (resource) | Value <> Risk, then lookup score | If Education Limit, then <adjust> risk by <value> | Based on risk value, select weight factor (e.g. 10) |
| 4 | Genomic Data | Upload genomic data from personal testing (request upload) | SNP Value <> Risk, then lookup risk score (based on attributes identified) | If family history <> direct family members, then <adjust> risk by <value> | Based on risk value, select weight factor (e.g. 30) |
| 5 | Exposure to Lead | Single question (yes or no) | Value <> Risk, then Risk Identified | If Spouse Exposure, then <adjust> risk by <value> | Based on risk value, select weight factor (e.g. 15) |

DELIVERING INFORMATION AND VALUE TO PARTICIPANTS IN DIGITAL CLINICAL TRIALS

BACKGROUND

Many computer systems are configured to consistently provide a standard set of outputs or a standard type of output. However, a standard output may not be relevant and useful in all situations, since users may find themselves in different situations or may have different needs. For example, the level of detail of information in a user interface may be excessive and confusing for some users while at the same time being insufficient for other users. As a result, in many cases, the outputs of devices, software applications, control systems, and other computer-based systems are not as relevant and useful to the recipients as they could be.

SUMMARY

In some implementations, a computer system is configured to customize its output for a particular situation or user. The system can obtain context information and evaluate the relevance and usefulness of potential outputs and actions with respect to the context indicated by the context information. For example, the system can vary the type and format of output information based on information that describes the intended recipient and the situation of the recipient. As discussed further below, the system can take into account many different factors in its evaluation, including timing, user preferences, user history, user classification, impact or effect of the system's decisions on users, and more. These evaluations can allow the system to return information to users and perform actions (e.g., control functions, management functions, etc.) in a manner that is most appropriate and useful. In addition to improving the quality and type of information provided as output, the evaluations can more generally allow the system to enhance the overall utility of its actions, e.g., by maximizing the value or benefit provided by the actions that the system recommends or performs.

Beyond adjusting output to user interfaces, the system can be used to dynamically adjust output that causes actions on behalf of a subject. For example, the system can provide output that manage devices, change device configurations, update software or hardware settings, and so on. For example, to maximize the benefit that a system provides to a user, the system may adjust monitoring and reporting of information from a client device to a server in a way that is customized for the context and preference of the device and user. For one user's phone, the system may determine that the phone has a battery power level above a threshold and that the phone is moving quickly. In response, the system may determine that an appropriate system output is a control instruction to instruct the phone to increase the frequency of acquiring and reporting sensor data to a server, because this monitoring will better describe the current level of activity. For another user's phone, however, the system may determine that the phone's battery power level is below a threshold or that the current level of movement is low, and in response the system may determine that an appropriate system output is a control instruction for the phone to decrease the frequency of acquiring and reporting sensor data to a server, to conserve power and network bandwidth.

To determine an action to perform (e.g., instructing an increase or decrease in measurement and reporting frequency), the system can evaluate the appropriateness of the action for the current context across multiple dimensions, e.g., whether an assessment of the context is reliable, whether the candidate action is likely to be effective, whether the action is applicable for the context, whether the timing of the action is appropriate, the amount of benefit the action will provide, and so on. With this analysis, the system can appropriately select its actions and outputs to improve the state of the subject, e.g., improve the functioning of a device or provide benefit to a user. The evaluation of the system can be used to limit or avoid actions that would lead to negative outcomes or uncertain results. For example, the system can obtain data indicating an action to be performed for a subject, whether the proposed action is determined by the system, by the user, or by a third party. The system can evaluate the action with respect to the current context of the subject and to block or bypass the action if the system's evaluation predicts the likelihood or magnitude of benefit provided is too low. On the other hand, the system can validate and approve actions that it predicts to be beneficial for the subject.

In customizing outputs and making other decisions, the system can use machine learning models that are based on data sets for a variety of subjects. The models can include clustering models that group subjects according to similar characteristics and historical patterns, classifiers to interpret contexts and generate inferences about subjects, and predictive models that can be used to predict the types of outcomes that might occur and the likelihoods of the outcomes. In some implementations, one or more of the evaluations of the system can be based on output of one or more trained machine learning models, such as neural networks, maximum entropy classifiers, reinforcement learning models, and so on.

The system can be used to improve outputs to or on behalf of different types of subjects. In some implementations, the system customizes output for a user, but in other implementations the system can customize output for another type of subject, such as a device, a system, a network, a model, a hardware component, a software module, an organization, a group of people, etc. For example, the techniques discussed herein can be used to customize the type of outputs that a server, client device, software application, or other technology provides for output to a user on a user interface. As another example, the same techniques can be used to customize how an operating system or server manages other components, such as by customizing load balancing and resource allocation according to the context of components. As another example, a system can customize the actions it takes to maintain or manage a network by using context information to customize control instructions provided in different situations.

The system can perform processing to enhance the relevance and usefulness of outputs. Relevance can represent to the applicability of information and actions to a subject, for example, whether information is related to or is likely to be of interest to a user and the subject's current situation. Usefulness can represent the level of value that information and actions provide to a subject, for example, the extent that an action of the system benefits the subject. Relevance and usefulness can be enhanced through analysis of characterization data that describes the subject for which the system is customizing output. For example, the characterization data can indicate attributes of the subject, activities of the subject, preferences of the subject (e.g., a user profile, a device profile, etc.), and so on. Relevance and usefulness can also be enhanced with analysis of context data that describes the current situation of the subject, e.g., a location of the subject, a task or activity of the subject, an identity of people or devices near the subject, a state of the subject (e.g., an operating state of a device, a physiological or mental state of a person, etc.), an environment of the subject, etc.

In some implementations, the system is configured to select or analyze actions to be taken on behalf of a subject. The system can provide a decision engine or recommendation engine to evaluate options for improving the state of a subject. The system can evaluate actions to be taken by people or devices to determine whether the actions affect the state of the subject positively rather than negatively. In some implementations, the system evaluates different options and selects one that is predicted to improve the status or condition of the subject. As an example, for managing network infrastructure, the system can be used to select control instructions predicted to improve data transfer performance given the current traffic or configuration of the network. As another example, in medical applications, the system can be used to select treatment or behavioral recommendations predicted to improve a person's health and wellbeing.

The system can act in a supervisory role or advisory role to validate actions for user or a device to perform, using inputs from various sources to evaluate the potential effects of the actions and the applicability for the current context. The system may block or filter out actions that are predicted to not achieve the desired improvements and thus do not provide sufficient utility or value for the subject. For example, for managing network infrastructure, the system can review proposed network changes given the current context of the network, and then adjust or cancel the changes if they are predicted to cause disruption or fail to achieve desired improvement. As another example, in medical applications, the system can evaluate a proposed treatment for a person in view of the person's current situation, and then recommend changes if the calculated benefits are not sufficiently greater than the predicted risks and costs of proceeding.

The system can perform processing to evaluate actions and outputs across multiple aspects or dimensions, such as reliability, efficacy, applicability, timing, variability of results, benefits and costs, and so on. These aspects can be evaluated whether the system is selecting actions to be perform or is evaluating actions already selected. These evaluations can be performed to evaluate outputs to provide (e.g., recommendations, instructions, information for display on a user interface, etc.) as well as actions to perform (e.g., changes to device configurations, medical treatments, etc.). As discussed further below, these evaluations can be made using data from a variety of sources, including sensor data from sensing devices, usage logs, activity logs, user inputs, and other information that is stored in databases or is otherwise collected.

The system can perform reliability evaluation to assess whether a classification for the subject is correct (e.g., status of a device, diagnosis for a person, etc.). This can involve evaluating the extent that the classification of a subject or other data about the subject is consistent with the overall set of information about the subject. In other words, the reliability evaluation can assess the extent to which the data about a subject (as well as inferences or conclusions made using that data) can be trusted. This can help ensure that the system is addressing the right problem, for example that a condition or error to be addressed is legitimate and is correctly identified. The reliability evaluation may involve generating a reliability score or confidence score indicating a level of confidence in the classification for the subject or for data about the subject.

The system can perform efficacy evaluation to assess the predicted results of performing an action or providing an output, including a determination of whether and to what extent performing the action is likely to improve the condition of the subject. This can help ensure that the action under evaluation is the right action to improve the state of the subject. The efficacy evaluation can be made using a target outcome (e.g., a benchmark, a goal, a reference state, etc.) to evaluate whether the action can achieve or contribute to achieving the target outcome. The efficacy evaluation may involve generating an efficacy score, for example, a measure that quantifies predicted effects of the action, a probability score indicating a likelihood that a desired result will be achieved by the action, etc.

The system can perform applicability evaluation to assess how applicable an action or output is for a subject. This can help ensure that the action is applicable and relevant to the subject. The applicability evaluation can assess whether the subject is the right one (e.g., the right device, the right user, etc.) to receive the output or to have the action performed for the subject. In general, the system aims to customize or tailor actions and outputs for the subject and the subject's current context. The efficacy evaluation may involve generating an applicability score or customization score, for example, a measure that indicates how appropriate an action is for a specific subject.

The system can perform timing evaluation to assess timing appropriate to provide an output or perform an action for a subject. Even if an action or output is appropriate for a subject, the current time may not be appropriate because of other activities, conditions, or preferences of the subject. Thus, the timing evaluation can assess whether the current time (or another time) is the right time to perform an action or provide an output for the subject. The timing evaluation may involve generating a timing score that indicates, for example, how appropriate a particular time is for performing an action or providing an output.

The system can perform an uncertainty evaluation to assess the variability of results or range of potential results that may result from an action. The results of an action can vary, often based on the subject and circumstances but also based on unknown or unpredictable factors. The system can use data describing similar actions taken for similar subjects in similar contexts to estimate the range of outcomes that are likely. The uncertainty evaluation can involve generating a variability score indicating a level of variation or uncertainty in results of carrying out an action.

The system can perform evaluations to assess benefits of performing an action, costs of performing an action, and whether the benefits sufficiently outweigh the costs. This type of processing can evaluate the tradeoffs that are required by actions that the system performs or recommends. Even if an action is determined to be beneficial for the subject, there are additional costs that may diminish our outweigh the benefits. In general, cost can refer to what is given up or lost by performing an action, such as lost time, lost opportunities, options foreclosed by carrying out the action, etc. For example, in management of devices, the cost may involve committing resources (e.g., processing power, memory capacity, storage capacity, network bandwidth, battery power or battery life, etc.) or the fact that a configuration may improve one aspect of performance (e.g., throughput) but may negatively affect another aspect of performance (e.g., latency).

The system can use the evaluation to ensure that the actions it performs or recommends for a subject improve the state of the subject. As an example, the system can be used to monitor and manage network infrastructure. The system can receive information indicating a classification (e.g., for a status or condition) of the subject, such as response time being below a desired level, and may evaluate different candidate options for (e.g., restarting a router, changing the value of a network setting, etc.). For each of the options, the system can evaluate the factors discussed above. For example, the system can assess whether the status information is reliable, e.g., whether the low response time measure is consistent with other performance measures and is not an outlier in a series of response time measurements. The system can assess whether a candidate option is likely to improve the response time, given the effect of the same or similar action in other networks. The system can assess the applicability of a candidate option for the particular network, given the configuration and current activity of the network. The system can assess the timing of carrying out the candidate option, including whether to delay or postpone corrective action until conditions in the network change. These and other evaluations allow the system to determine whether to recommend or carry out the candidate option to address the issue of low response time detected. In this manner, the system can improve the functioning of devices with customized control and configuration based on the context of a device.

As another example, the techniques can be used to select or review a medical treatment. The system can receive information about an individual, such as a classification (e.g., for a status or condition) of the individual, such as a diagnosis of a health condition. The system can use information about the individual, including sensor data, mobile device data, electronic health records, and so on, to evaluate whether the classification is correct. The system can assess whether a candidate option (e.g., a digital therapeutic provided through a mobile device, a pharmaceutical, etc.) for the individual is likely to improve the condition of the individual, based on a rich set of data (e.g., behavior data, genomics data, survey data, etc.) about the individual and other individuals. The system can also assess the applicability of the candidate option for the individual, based on context data indicating a current situation and environment of the individual. The system can assess the timing of carrying out the candidate option, including whether to delay or postpone implementing the candidate option. These and other evaluations allow the system to determine whether to recommend or carry out the candidate option, and safe and effective care is provided. This aspect of the system can provide effective decision support to doctors, patients, and others. For example, the system can be integrated with electronic health record systems to automatically vet proposed actions and reduce errors, as well as to identify and reduce unnecessary procedures and tests that have marginal benefit.

In one general aspect, a method includes: obtaining, by the one or more computers, characterization data describing a subject, where the characterization data comprises data indicating one or more physical characteristics of the subject obtained from data stored in a database; identifying, by the one or more computers, a classification for the subject and a candidate option for altering a state of the subject; generating, by the one or more computers, one or more evaluation measures for the candidate option based on the characterization data for the subject and the classification for the subject; validating, by the one or more computers, the candidate action for the subject based on evaluating each of the one or more evaluation measures with respect to a corresponding reference value; and in response to validating the candidate action for the subject, providing, by the one or more computers, output to cause at least one of initiating one or actions of the candidate option, storing the candidate option in association with the subject, or causing a notification presenting the candidate option to be provided to a device associated with the subject.

In some implementations, the method includes obtaining context data indicating a current context of the subject, the context data indicating a current status of the subject. The context data comprises sensor data from one or more sensors of the subject or a device associated with the subject. The one or more evaluation measures for the candidate option are based on the characterization data for the subject and the context data for the subject.

In some implementations, validating the candidate option comprises at least one of: comparing at least one of the evaluation measures with a predetermined threshold; and comparing at least one of the evaluation measures with a reference value representing an evaluation measure for an alternative candidate option for altering the state of the subject.

In some implementations, the subject is a device, a system, a network, a model, a hardware component, a software module, an individual, a group of people, or an organization.

In some implementations, obtaining the characterization data comprises obtaining information generated based on sensor data from one or more sensors.

In some implementations, the method comprises at least one of: generating at least one evaluation measure for the subject using a machine learning model; or generating the reference value corresponding to at least one evaluation measure using a machine learning model.

In some implementations, the classification is an indication of a condition of the subject, and generating the one or more evaluation measures comprises generating a confidence score for the classification based on the physical characteristics of the subject.

In some implementations, generating the one or more evaluation measures comprises generating an efficacy score for the candidate option, where the efficacy score is indicative of predicted results of the candidate option for the subject based at least on the physiological data.

In some implementations, the classification is an indication of a condition of the subject. The efficacy score is a measure of a likelihood or degree that the candidate option will reduce or remove the condition.

In some implementations, generating the efficacy score for the candidate option comprises: providing feature data derived from the characterization data for the subject and context data for the subject to a trained machine learning model that has been trained based on example data sets including (i) characterization data for other subjects, and (ii) context data for the other subjects, and (iii) outcomes of performing the candidate option for at least some of the other subjects; and generating the efficacy score based on output that the trained machine learning model generated by processing the feature data.

In some implementations, the method includes receiving context data indicating a context of the subject. Generating the one or more evaluation measures comprises generating a customization score indicating a level of applicability of the candidate option for the subject, the customization score being generated based on the context data.

In some implementations, generating the one or more evaluation measures comprises generating a timing score indicating an appropriateness of the candidate option for the subject, where the timing score is based on (i) historical data for the subject and (ii) the context data for the subject.

In some implementations, generating the one or more evaluation measures comprises generating a variability score indicating a level of variation or uncertainty for results of implementing the candidate option.

In some implementations, the method includes generating the one or more evaluation measures comprises generating a one or more scores based on predicted benefits of the candidate option and one or more costs of the candidate option.

In some implementations, the method includes: determining a target outcome for the state of the subject; and selecting the candidate option, from among multiple candidate options, based on the target outcome for the state of the subject.

In some implementations, the method includes: clustering a plurality subjects into clusters based on characterization data for the plurality of subjects; and identifying a cluster for the subject. Generating the one or more evaluation measures is based on the identified cluster for the subject.

In some implementations, generating the one or more evaluation measures comprises obtaining output of one or more machine learning models that comprises a prediction based on feature data derived from the characterization data, where the one or more models have been trained based on training data indicating (i) activities or attributes of other subjects and (ii) outcomes identified for the other subjects.

In some implementations, the one or more machine learning models comprise at least one of a neural network, a support vector machine, a classifier, a regression model, a reinforcement learning model, a clustering model, a decision tree, a random forest model, a genetic algorithm, a Bayesian model, or a Gaussian mixture model.

In another general aspect, a method performed by one or more computers includes: obtaining, by the one or more computers, characterization data describing a state of a subject, the characterization data indicating one or more physical characteristics of the subject; determining, by the one or more computers, a target state for the subject, where achieving the target state requires a change in the state of the subject; generating, by the one or more computers, a context profile for the subject based on the characterization data for the subject and characterization data for other subjects, where the context profile comprises data to customize evaluation of actions to interact with the subject; based on the context profile, selecting, by the one or more computers, an action to change the state of the subject toward the target state, where the action is selected from among a plurality of candidate actions; and providing, by the one or more computers, output configured to initiate the selected action for the subject or provide an indication of the selected action for display on a user interface of a device associated with the subject.

In some implementations, generating the context profile comprises using a machine learning model to generate a classification for the subject. The classification for the subject is used to generate the context profile.

In some implementations, the machine learning model is trained based on the characterization data of the other subjects. Using the machine learning model to generate a classification for the subject includes: processing input feature data for the subject that is derived from the characterization data for the subject using the machine learning model; and determining the classification based on output that the machine learning model provided in response to processing the input feature data for the subject.

In some implementations, the machine learning model comprises at least one of a neural network, a support vector machine, a classifier, a regression model, a reinforcement learning model, a clustering model, a decision tree, a random forest model, a genetic algorithm, a Bayesian model, or a Gaussian mixture model.

In some implementations, selecting the action comprises: using a machine learning model to provide a prediction for one or more of the candidate actions based on the characterization data describing the subject, where the prediction comprises at least one of (i) a predicted likelihood of change toward the target state or (ii) a predicted magnitude of change toward the target state; and selecting the action based on the prediction of the machine learning model.

In some implementations, performing clustering subjects into clusters based on similarities among the characterization data of the subjects. The context profile for the subject is generated based on tracked outcomes for subjects in a cluster that includes the subject.

In some implementations, the subject is a device, and the method comprises determining a classification for the state of the subject based on the characterization data for the subject, where the classification corresponds to an error state of the device. Generating the context profile comprises generating the context profile based on data about other devices that are in or have experienced the error state.

In some implementations, the context profile comprises at least one of: a scoring function for generating an evaluation measure for the subject; a weighting for one or more evaluation factors; a reference value or function for generating a reference value; a preference derived from data about the other subjects; or a function for generating a composite score or a reference value corresponding to a composite score.

Other embodiments of these and other aspects disclosed herein include corresponding systems, apparatus, and computer programs encoded on computer storage devices, configured to perform the actions of the methods. A system of one or more computers can be so configured by virtue of software, firmware, hardware, or a combination of them installed on the system that, in operation, cause the system to perform the actions. One or more computer programs can be so configured by virtue having instructions that, when executed by data processing apparatus, cause the apparatus to perform the actions.

The details of one or more embodiments of the invention are set forth in the accompanying drawings and the description below. Other features and advantages of the invention will become apparent from the description, the drawings, and the claims.

BRIEF DESCRIPTION OF THE DRAWINGS

FIG. 18 illustrates an example of a table illustrating types of information and related scoring functions.

Like reference numbers and designations in the various drawings indicate like elements.

DETAILED DESCRIPTION

Figure 1A:
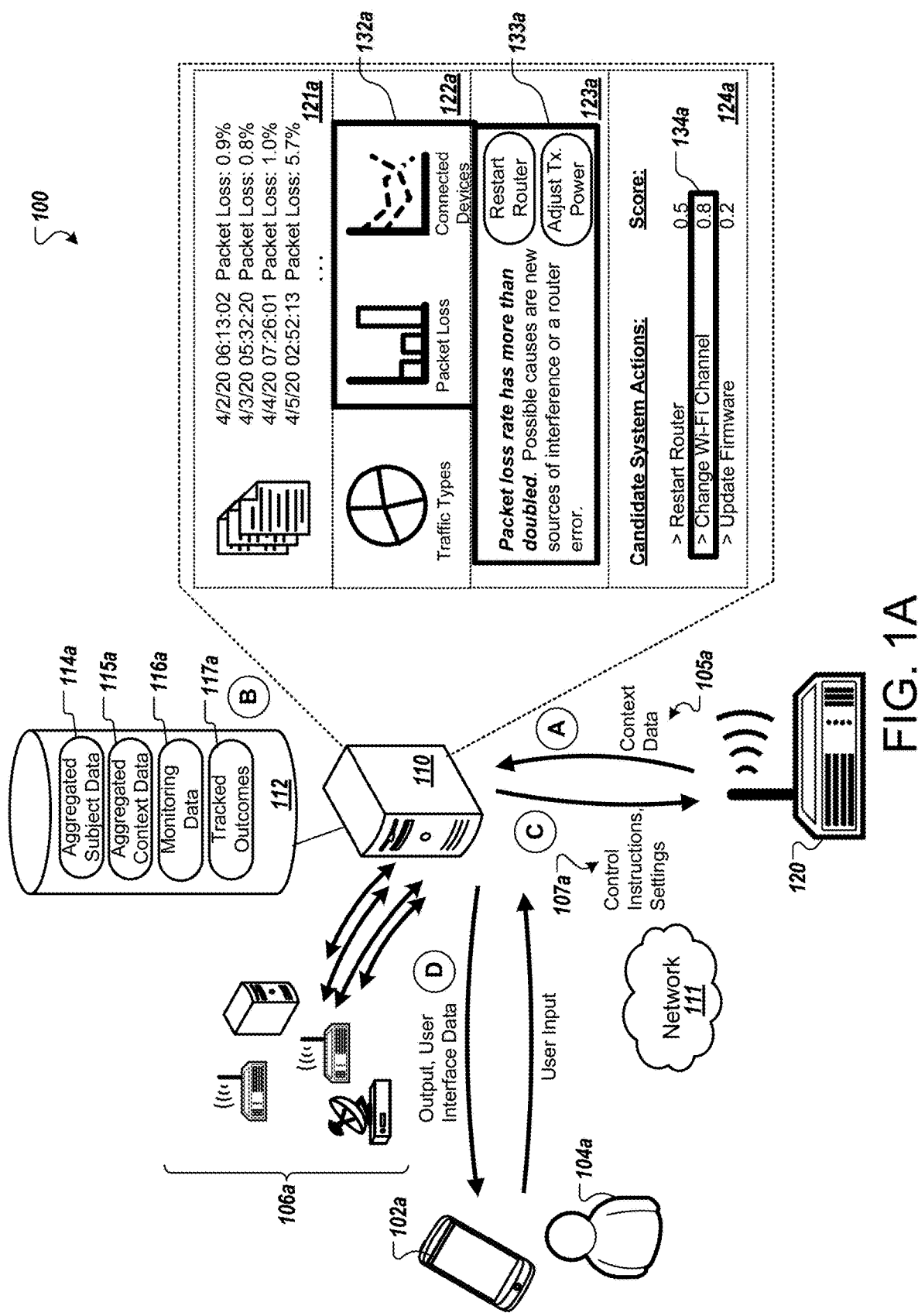
FIGS. 1A and 1B are diagrams showing an example of a system including a server system configured to perform context-based analysis to enhance computer output.
Figure 1B:
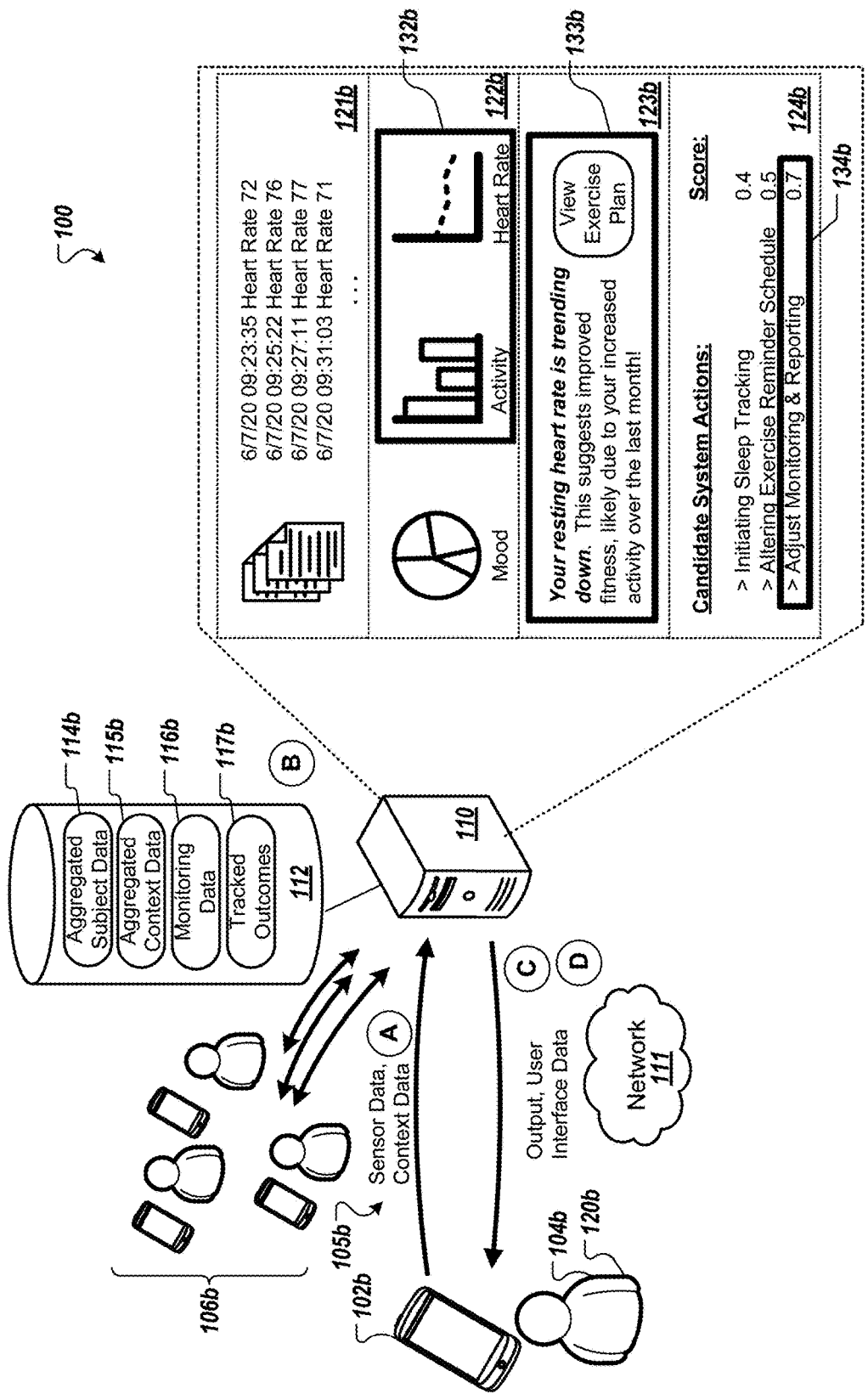

FIGS. 1A and 1B are diagrams showing an example of a system 100 for context-based analysis to enhance computer output. The system 100 includes a computer system 110, a database 112, a client device 102a, a subject 120a, and other subjects 106a. The computer system 110 is configured to receive context data about the subject 120a and evaluate potential actions to improve the state of the subject 120a and customize outputs of the computer system 110. The computer system 110 is configured to monitor and adjust outputs for a variety of subjects 106a, which in this case are all types of computer network infrastructure. The computer system 110 uses the aggregated data about all of these subjects 106a, 120a, to customize the management of each subject individually, according to its particular context.

Unlike many computing devices and software applications, the computer system 110 includes capabilities to adaptively adjust the outputs it provides and the actions it performs. The computer system 110 uses these capabilities to address the uniqueness of different subject and their situations. In particular, the computer system 110 can selectively provide outputs that the computer system 110 determines are likely to provide at least a minimum level of benefit given context data indicating a current context. For example, based on context data provided by a mobile device or other device, the computer system 110 can select a subset from among the various types of information that are known to be relevant to the context of the device. The computer system 110 can make this selection based on various evaluations, described in more detail with respect to FIG. 2. In short, the computer system 110 can perform evaluations of relevance, importance, benefit, and more based on characterization data (e.g., data describing a subject, including physical attributes, history, and so on) and context data (e.g., data indicating the current situation of the subject, e.g., current status, activities, location, and so on). The computer system 110 can predictively quantify the benefit or value that a given output or action is expected to provide, and provide only the outputs predicted to provide a sufficient amount of value.

As an example, the computer system 110 can selectively adjust the types of outputs it provides, e.g., from among different levels of detail or precision, from among different communication channels (e.g., e-mail, text message, phone notification, etc.), from among different types of media (e.g., image, video, text, audio, etc.), from among messages with different purposes (e.g., educational messages, notification messages, warning messages, recommendation messages, etc.). The type of message provided to a given user can vary based on the context of a device and an associated user, as well as the characteristics of the device and user.

The computer system 110 can include one or more computers, which may be located together or may be distributed in multiple locations. The computer system 110 communicates with other devices, including the subjects 106a, 120a, over a network 111. The network can include public and private networks, including the Internet.

The subjects 120a, 106a each provide context data that includes information about respective contexts. This context data can include, for example, settings, configuration data, status information, usage statistics, physical location, interactions with users or other devices, performance data, error data, workload and resource utilization data, and so on. Each subject can be associated with a unique identifier, and the computer system 110 stores information about the subjects in the database 112. In many cases, different sets of subjects may be monitored and assisted by the computer system 110 at different times. The computer system 110 may store and use information about subjects that were previously monitored and assisted by the computer system 110, even if those subjects are not currently being actively monitored or assisted by the computer system 110.

The aggregated subject data 114a can include characterization data that describes each subject 120a, 106a. The characterization data can describe attributes of a subject, activities of the subject, historical information about the subject, and so on. In some implementations, the characterization data for a subject can include historical context data, e.g., a series of previous context data reports (e.g., communications indicating a prior state or context of the subject) or information derived from previous context data reports.

The computer system 110 can obtain information about the subjects from various different sources. Information can be obtained from subjects directly, for example, in response to requests from the computer system 110 or from periodic reports provided by the subjects. Information may be obtained from other sources, such as other servers, to provide specifications, historical data, and so on.

In addition to various types of general information about subjects in the aggregated subject data 114a, the computer system 110 also receives context data from the subjects 120a, 106a. This context data can be provided by subjects directly or indirectly. For example, subjects may provide context data periodically, in response to changes in context, and so on. As another example, context data can be provided by users, nearby devices, or other systems. The context data for the various subjects is shown as aggregated context data 115a.

The computer system 110 monitors the status of subjects over time. This includes capturing sensor data, results of actions, and more. This is shown as monitoring data 116a. From the context data and monitoring data, The computer system 110 identifies outcomes due to various contexts and conditions, as well as results of actions that the computer system 110 instructs. This information is stored as tracked outcomes 117*a*.

With the various types of data stored in the database 112, the computer system 110 can use the tracked outcomes 117*a* for many subjects to customize the server's actions and outputs for individual subjects.

FIG. 1A shows an example in which the subject 120*a* is a router in a communication network and the computer system 110 evaluates the context of the subject 120*a* and determines management actions and outputs for display at a client device 102*b*. The server has many potential outputs that it can provide to the client device 102*a* add to the subject 120*a*. The computer system 110 evaluates the various options, based on information about the subject 120*a* and its context, to selectively provide outputs and selectively perform actions to improve the state of the subject 120*a*.

In stage (A), the subject 120*a* provides context data 105*a*. The context data 105*a* can indicate status of the subject 120*a*, characteristics of an environment of the subject 120*a*, resources allocated to the subject 120*a*, activities or workload of the subject 120*a*, and more. In this example, the subject 120*a* also provides usage logs indicating how the subject 120*a* has been used over at a period of time in the past.

The subject 120*a* (or a device associated with the subject 120*a*) provides the context data 105*a* to the computer system 110 over the network 111. The computer system 110 stores the received context data 105*a* in the database 112 in association with an identifier for the subject 120*a* to which the context data 105*a* corresponds.

In stage (B), the computer system 110 uses information from the database 112 to assess the current context for the subject 120*a* and to select outputs and actions that are appropriate for the subject and its current context. This includes various evaluations of the appropriateness of different options for the subject 120*a*, including an assessment of timing, reliability of data, potential benefits and costs, and more.

The computer system 110 uses previously stored information about the subject 120*a* from the aggregated subject data 114*a*. This can include characterization data indicating physical characteristics (e.g., size, dimensions, weight, structure, capabilities, etc.), history (e.g., previous activities, conditions experienced, previous communications, etc.), and more. In this example, where the subject is a router, this can include information such as a model number for the router, specifications of the router, a location or arrangement of the router in a network, historical use data for the router, and so on.

The computer system 110 makes a series of determinations about the subject 120*a*. These include making a classification for the subject 120*a*, identifying aspects of the context of the subject 120*a*, and determining if action is needed to correct or improve the state of the subject 120*a*. Using the information about the subject 120*a* in the subject data 114*a* and context data 115*a*, the computer system 110 determines a classification for the subject 120*a*. This can involve selecting a classification from various predetermined options, such as normal operation, error, decreased performance, above average performance, light load, heavy load, average load, and so on. Each of these classifications may refer to a state or condition of the subject 120*a*. Some of the classifications may be desirable or benign, so that no corrective action is needed. On the other hand, some classifications may correspond to conditions showing that the subject 120*a* is not in a desirable or properly operating state.

For these, the computer system 110 determines management actions that can improve the state of the subject 120*a*. The computer system 110 also determines outputs for presentation to a user that can help address the needs of the subject 120*a*. The management actions and the outputs for presentation on the client device 102*a* can be customized for the characteristics of the specific subject 120*a* and the current context of the subject 120*a*.

In the illustrated example, the subject 120*a* is a router that has its performance and operation monitored and adjusted by the computer system 110. The router 120*a* recently began experiencing higher than usual packet loss rates. In the example, the computer system 110 analyzes the available information about the subject 120*a*. The computer system 110 can also compare information about the subject 120*a* with information about other subjects 106*a*. For example, the computer system 110 has available raw data 121*a* that indicates packet loss statistics over time for the subject 120*a*. The computer system 110 determines that the most recent packet loss measurement of 5% is significantly larger than previous or average measurements. The computer system 110 can also compare the most recent measurement, or pattern of measurements, with measurement data for the other subjects 106*a*. The computer system 110 can determine that the pattern experienced by the subject 120*a* matches or is similar to patterns of measurements for the other subjects 106*a* when they experienced error conditions. From these and other evaluations, the computer system 110 determines the classification for the subject 120*a*, which in this case is that the subject 120*a* is in an error state with high packet loss.

Other techniques for determining a classification or detecting a problem with the subject 120*a* can also be used. For example, a machine learning model can be trained, based on data in the database 112 (e.g., indicating subject data 114*a*, context data 115*a*, monitoring data 116*a*, and tracked outcomes 117*a*) to predict classifications. For example, based on input feature data indicating subject characterization data and context data, the model can output a likelihood score (e.g., a probability or confidence score) for each of one or more classifications in a predetermined set of classifications, with each likelihood score indicating how likely the corresponding classification applies to the subject whose information is provided as input to the model.

Once a classification for the subject 120*a* is determined, the computer system 110 determines whether action is needed to change the state of the subject 124. The computer system 110 also determines whether output should be provided for presentation by the client device 102*a*, and if so, what the form and content of the output should be. The computer system 110 can store data (such as look up tables) that indicate which classifications or conditions of subjects need to be addressed or corrected. In this case, the high packet loss classification is determined to warrant corrective action and output. The computer system 110 selectively determines which types of actions and outputs to provide based at least in part on the context data for the subject 120*a*.

The computer system 110 has the option to provide various types of outputs, including raw data, processed data, applied data or inferences, and control or management information.

The first category, raw data 121*a*, can include measurement from sensors, from the subject 120*a*, and from other sources. The usefulness of this data to a user may vary significantly, with the data being very useful to some users and not useful to others. Similarly different types of measurements are relevant to different conditions or classifications of a subject. In the example, the computer system 110 determines, based on the classification and current context, that the raw data 121*a* would not be appropriate as an output for presentation.

The second category, processed data 122*a*, can include aggregations, interpretations, and inferences based on gathered data. There are many options for creating and selecting this type of information, and the relevance or importance of the various types can vary significantly based on the subject 120*a*, the context, the classification for the subject, preferences of an associated user 104*a*, and so on. In the example, the options for processed data include visualizations of different aspects of the subject 120*a*. These include charts of traffic types, packet loss, and connected devices. In the example, the computer system 110 determines that the measures of packet loss and connected devices are relevant to the classification for the subject and the current context, and so the computer system 110 selects visualizations for these measurements to be provided. These selected output elements 132*a* can then be provided for presentation by the client device 102*a*.

The third category of output is applied or actionable information 123*a*. For example, the computer system 110 can interpret the processed data 122*a* and generate inferences or interpretations to explain the cause or nature of the conditions that resulted in the classification. In some cases, the computer system 110 can use the classification process to guide this interpretation, for example, by identifying the factors that led to the classification and providing an explanation about those factors.

As part of providing the applied or actionable information 123*a*, the computer system 110 can provide data for interactive user interface elements relevant to the classification. For example, given the classification of a high packet loss, the computer system 110 can identify a set of actions that are predicted to improve the state of the subject 120*a*. These include restarting the router and adjusting transmission power. The computer system 110 can instruct the client 102*a* to provide user interface controls that, when selected, initiate the corresponding actions. In this example, restarting the router may clear memory buffers, reload software, and change the operating state to recover from errors that may be contributing to the packet loss rate. Similarly, increasing transmission power may improve signal quality in the presence of interference and thus also reduce the packet loss rate.

The fourth category of output includes system actions 124*a* that the computer system 110 may initiate to improve the state of the subject 120*a*. These actions can be evaluated so that they are taken only when calculated to provide improvement or otherwise provide value. First, the computer system 110 can identify actions that have improved the state of subjects in the condition or classification of the current subject. For example, the computer system 110 can use the data in the database 112 and identify actions performed for the other subjects 106*a* when they had the same classification as the subject 120*a*, and identify which of those actions lead to improvement and the extent of improvement. This analysis can be context-dependent, so the computer system 110 limits its analysis to or at least weights its analysis based on examples of other subjects 106*a* having attributes similar to the subject 120*a*, and/or have contexts similar to the current context of the subject 120*a*.

As an example, the computer system 110 identified three candidate options for improving the state of the subject 120*a*, each involving a different action. These include restarting the router, changing the Wi-Fi channel of the router, and updating firmware for the router. The computer system 110 evaluates each of these options and assigns a score to each. The score can indicate the applicability of the candidate option given the information known about the subject 120*a* and the current context of the subject 120*a*. For example, data about other subjects 106*a* (e.g., other routers or other networking devices) may indicate that updating firmware has a very high likelihood of resolving packet loss problems, at least in general among a population of many devices. However, subject characterization data for the subject 120*a* may indicate that the subject 120*a* already has up-to-date firmware, and so this action would not provide a benefit. In addition, or alternatively, the computer system 110 may determine that the firmware update option would disrupt the function of the subject 120*a* for an excessive amount of time, making it a poor choice for the subject 120*a* at the current time when context data indicates moderate to heavy use.

On the other hand, the computer system 110 may determine that changing the Wi-Fi channel of the router has a high likelihood of improving the packet loss rate. Tracked outcomes 117*a* for similar subjects 106*a* may show a high likelihood of success. As another example, context data from the subject 120*a* may indicate high congestion on the current channel and less congestion on other channels, suggesting that changing the channel would have a positive effect. Similarly, the computer system 110 may determine that the level of disruption to the subject 120*a* for this candidate option is relatively low, e.g., only for a short duration. As a result, the computer system 110 assigns a score for this option that is higher than the others. The computer system 110 selects this option as an action 134*a* to be performed.

The computer system 110 does not necessarily perform any action, even if relevant candidate options for improving the state of the subject 120*a* are available. For example, if all of the available candidate options have scores that are less than a minimum threshold (e.g., indicating that the applicability, relevance, or benefit of the options is low), then the computer system 110 may choose not to perform any of the candidate options. Nevertheless, if the conditions and classification of subject 120*a* persist, the computer system 110 can perform the evaluations again as new information is received, especially as the context of the subject 120*a* changes and potentially makes some of the candidate options more appropriate or beneficial.

In stage (C), the computer system 110 carries out the selected action 134*a* to improve the state of subject 120*a*. In this case, the computer system 110 sends control instructions 107*a* to the router over the network 111, instructing the router to change its Wi-Fi channel to channel that is less congested. This action is performed automatically by the computer system 110 based on its evaluation that the change will improve the operation of the router, e.g., to reduce the severity of or remove the high packet loss condition classified for the router.

In stage (D), the computer system 110 sends selected outputs 132*a* and 133*a* to the client device 102*a* for presentation to the user 104*a*. Although the computer system 110 had many types of outputs that were determined to be relevant to the subject 120*a* and its classification, and even to its current context, the computer system 110 provides only a selected subset for presentation. For example, the computer system 110 could provide raw data 121*a*, processed data 122*a*, and applied or actionable information 123*a* which are determined to be relevant to the subject 120*a*, its classification of high packet loss, and its current context. Nevertheless, the computer system 110 selects only a subset of those categories of information, based on determining that not all of the information would be beneficial to the user 104a. In this case, not all the categories of information 121a, 122a, 123a are provided (e.g., no raw data 121a is provided). Within the category of processed data 122a, not all of the potential visualizations or data types are provided either, with only a portion being selected for presentation. The computer system 110 can select this subset of the available and relevant data based on the information known about the user 104a and the current context of the user 104a.

FIG. 1B shows another example in which the computer system 110 determines customized output and management actions. In this example, the subject 120b is a user 104b associated with a mobile device 102b (e.g., a phone, smart watch or other wearable device, etc.). Through communication with the mobile device 102b over the network 111, the computer system 110 can obtain information about the subject 120b, such as physiological information, behavioral information, mood information, and more. The mobile device 102b provides context data that describes the current context of the subject 102b, such as the location, environment, activities, and movement of the subject 120b and the mobile device 102b. The computer system 110 uses the information, and information about other subjects 106b that each have corresponding devices, to determine personalized output suited for the subject 120b. The computer system 110 also determines and carries out actions to improve the state of the subject 120b, e.g., to enhance the health, performance, wellbeing of the subject 120b. These actions can be performed through behavioral support interactions, medical treatment, digital therapeutics, preventive care, etc., which can be provided using the mobile device 102b, medical devices (e.g., monitoring devices, respiratory equipment, assistive technology, insulin pumps, etc.) in a clinical or at-home setting, or other devices.

The computer system 110 receives context data for each of the subjects 120b, 106b that indicates information about their respective contexts. This context data can include, for example, settings, configuration data, status information, usage statistics, physical location, interactions with users or other devices, performance data, error data, workload and resource utilization data, and so on. Each subject 120b, 106b can be associated with a unique identifier, and the computer system 110 stores information about the subjects in the database 112. In many cases, different sets of subjects may be monitored and assisted by the computer system 110 at different times. The computer system 110 may store and use information about subjects that were previously monitored and assisted by the computer system 110, even if those subjects are not currently being actively monitored or assisted by the computer system 110.

The aggregated subject data 114b can include characterization data that describes each subject 120b, 106a. The characterization data can describe attributes of a subject, activities of the subject, historical information about the subject, and so on. In some implementations, the characterization data for a subject can include historical context data, e.g., a series of previous context data reports (e.g., communications indicating a prior state or context of the subject) or information derived from previous context data reports.

The computer system 110 can obtain information about the subjects from various different sources. Information can be obtained from subjects directly, for example, in response to requests from the computer system 110 or from periodic reports provided by the subjects. Information may be obtained from other sources, such as other computer systems (e.g., EMR/EHR systems, doctors' computer systems, hospital computer systems, etc.).

In addition to various types of general information about subjects in the aggregated subject data of 114b, the computer system 110 also receives context data from the subjects 120b, 106b. This context data can be provided by subjects directly or indirectly. For example, subjects may provide context data periodically, in response to changes in context, and so on. As another example, context data can be provided by nearby devices or other systems. The context data for the various subjects is shown as aggregated context data 115b.

The computer system 110 monitors the status of subjects over time. This includes capturing sensor data, results of actions, and more. This is shown as monitoring data 116b. From the context data and monitoring data, The computer system 110 identifies outcomes due to various contexts and conditions, as well as results of actions that the computer system 110 instructs. This information is stored as tracked outcomes 117b.

With the various types of data stored in the database 112, the computer system 110 can use the tracked outcomes 117b for many subjects to customize the server's actions and outputs for individual subjects.

FIG. 1B shows an example in which the subject 120b is an individual associated with the device 102b and the computer system 110 evaluates the context of the subject 120b and determines management actions and outputs for display at a client device 102b. The server has many potential outputs that it can provide to the client device 102b add to the subject 120b. The computer system 110 evaluates the various options, based on information about the subject 120b and its context, as well as information about other subjects 106b that are determined to be similar and/or to have experienced contexts similar to the context of the subject 120b, to selectively provide outputs and selectively perform actions to improve the state of the subject 120b.

In stage (A), the client device 102b provides context data 105b for the subject 120b. The context data 105b can indicate status of the subject 120b, characteristics of an environment of the subject 120b, activities of the subject 120b, and more. The device 102b associated with the subject 120b provides the context data 105b to the computer system 110 over the network 111. The computer system 110 stores the received context data 105b in the database 112 in association with an identifier for the subject 120b to which the context data 105b corresponds.

In stage (B), the computer system 110 uses information from the database 112 to assess the current context of the subject 120b and to select outputs and actions that are appropriate for the subject and its current context. This includes various evaluations of the appropriateness of different options for the subject 120b, including an assessment of timing, reliability of data, potential benefits and costs, and more.

The computer system 110 uses previously stored information about the subject 120b from the aggregated subject data 114b. This can include characterization data indicating physical characteristics of the subject 120b (e.g., height, weight, capabilities, test results, medical diagnoses, etc.), history (e.g., previous activities, conditions experienced, previous communications, medical history, treatment history, etc.), and more. In this example, where the subject is a person, this can include information such as EMR/EHR, reports of laboratory tests, reports of doctor visits, patient self-reported information, and so on.

The computer system 110 uses the information in the database 112 to determine a classification for the subject 120b. For example, the classification can represent a state or condition of the subject 120b. In the illustrated example, the subject 120b is a the user 104b, and the user's heart rate and physical activity (e.g., exercise) are being monitored by the system 100. The subject 120b has shown a pattern of resting heart rates that have decreased slightly over the previous few weeks.

Using the information about the subject 120b in the subject data 114b and context data 115b, the computer system 110 determines a classification for the subject 120b. This can involve selecting a classification from various predetermined options, such as healthy, compliant with a treatment regimen, non-compliant with a treatment regimen, and so on. Different classifications may represent the presence of different medical conditions (e.g., heart disease, diabetes, lung cancer, etc.) and/or different levels of severity of a medical condition (e.g., stage 1 cancer, stage 2 cancer, stage 3 cancer, cancer remission, etc.). Each of the classifications may refer to a state or condition of the subject 120b. Some of the classifications may be desirable or benign, so that no corrective action is needed. On the other hand, some classifications may correspond to conditions showing that the subject 120b is not in a desirable or healthy state, or that the state does not yet meet a goal or target for the subject 120b. For these, the computer system 110 determines management actions that can improve the state of the subject 120b. The computer system 110 also determines outputs for presentation to a user, which in this example is the subject 120b. The management actions and the outputs for presentation on the client device 102b can be customized for the characteristics of the specific subject 120b and the current context of the subject 120b.

The computer system 110 makes a series of determinations about the subject 120b. These include making a classification for the subject 120b, identifying aspects of the context of the subject 120b, and determining if action is appropriate to correct or improve the state of the subject 120b, e.g., to improve health or fitness, or to help achieve a goal. The computer system 110 also determines which outputs are most appropriate for the subject 120b given the subject's overall history and the most recent context data 105b for the subject 120b.

In the example, the computer system 110 analyzes the available information about the subject 120b. The computer system 110 can also compare information about the subject 120b with information about other subjects 106b of a similar type (e.g., other individuals, or other individuals determined to have similar attributes or histories to the subject 120b). For example, the computer system 110 has available raw data 121b that indicates heart rate over time for the subject 120b. The computer system 110 determines that the measured resting heart rates have decreased over the last few weeks. The computer system 110 can also compare the most recent measurement, or pattern of measurements, with measurement data for the other subjects 106b. The computer system 110 can determine that the pattern experienced by the subject 120b matches or is similar to patterns of measurements for the other subjects 106b when they had similar data patterns. From these and other evaluations, the computer system 110 determines the classification for the subject 120b, which in this case is that the subject 120b is showing indications of improved fitness. The computer system 110 may determine this by finding matching or similar patterns among the data of other subjects 106b, for example, where the aggregated subject data 114b indicates that decreasing resting heart rates have been indicative of greater exercise performance or better health outcomes for the other subjects 106b.

Other techniques for determining a classification for the subject 120b can also be used. For example, a machine learning model can be trained, based on data in the database 112 (e.g., indicating subject data 114b, context data 115b, monitoring data 116a, and tracked outcomes 117b) to predict classifications. For example, based on input feature data indicating subject characterization data and context data for the subject 120b, the model can output a likelihood score (e.g., a probability or confidence score) for each of one or more classifications in a predetermined set of classifications, with each likelihood score indicating how likely the corresponding classification applies to the subject 120b whose information is provided as input to the model.

Once a classification for the subject 120b is determined, the computer system 110 determines whether action is needed to initiate change in the state of the subject 124 or in one or more devices that monitor or assist the subject 120b. The computer system 110 also determines whether output should be provided for presentation by the client device 102b, and if so, what the form and content of the output should be. The computer system 110 can store data (such as look up tables) that indicate which classifications or conditions of subjects need to be addressed or corrected. In this case, the decreasing resting heart rate classification is determined to be a beneficial condition, so that no corrective action is needed, but output and monitoring adjustment are still appropriate. The computer system 110 selectively determines which types of actions and outputs to provide based at least in part on the context data for the subject 120b.

The computer system 110 has the option to provide various types of outputs, including raw data, processed data, applied data or inferences, and control or management information.

The first category, raw data 121b, can include measurement from sensors, from the device 102b and from other sources. The usefulness of this data to a user may vary significantly, with the data being very useful to some users and not useful to others. Similarly different types of measurements are relevant to different conditions or classifications of a subject. In the example, the computer system 110 determines, based on the classification and current context, that the raw data 121b would not be appropriate as an output for presentation.

The second category, processed data 122b, can include aggregations, interpretations, and inferences based on gathered data. There are many options for creating and selecting this type of information, and the relevance or importance of the various types can vary significantly based on the subject 120b, the context, the classification for the subject, user preferences, and so on. In the example, the options for processed data include visualizations of different aspects of the subject 120b. These include charts of mood, activity, and heart rate. In the example, the computer system 110 determines that the measures of activity and heart rate are relevant to the classification for the subject and the current context, and so the computer system 110 selects visualizations for these measurements to be provided. These selected output elements 132b can then be provided for presentation by the client device 102b.

The third category of output is applied or actionable information 123b. For example, the computer system 110 can interpret the processed data 122b and generate inferences or interpretations to explain the cause or nature of the conditions that resulted in the classification. In some cases, the computer system 110 can use the classification process to guide this interpretation, for example, by identifying the factors that led to the classification and providing an explanation about those factors.

As part of providing the applied or actionable information 123b, the computer system 110 can provide data for interactive user interface elements relevant to the classification. For example, given the classification of a reduced resting heart rate, the computer system 110 can identify a set of actions that are predicted to improve the state of the subject 120b or otherwise benefit the subject. The actions can be actions to be performed by the device 102b, the computer system 110, or the subject 120b. The computer system 110 can instruct the client device 102b to provide user interface controls that, when selected, initiate the corresponding actions. For example, the information 123b can include a user interface control that enables an action related to the information displayed (e.g., regarding increased activity and reduced heart rate), such as to view an exercise plan.

The fourth category of output includes system actions 124b that the computer system 110 may initiate to improve the state of the subject 120b. These actions can be evaluated so that they are taken only when calculated to provide improvement or otherwise provide value. First, the computer system 110 can identify actions that have improved the state of subjects in the condition or classification of the current subject. For example, the computer system 110 can use the data in the database 112 and identify actions performed for the other subjects 106a when they had the same classification as the subject 120b, and identify which of those actions lead to improvement and the extent of improvement. This analysis can be context-dependent, so the computer system 110 limits its analysis to, or at least weights its analysis based on, examples of other subjects 106b having attributes similar to the subject 120b, and/or have contexts similar to the current context of the subject 120b.

As an example, the computer system 110 identified three candidate options for improving the state of the subject 120b, each involving a different action. These include initiating sleep tracking for the subject 120b, altering a schedule for exercise reminders to the subject 120b, or adjusting monitoring and reporting of data by the device 102b. The computer system 110 evaluates each of these options and assigns a score to each. The score can indicate the applicability of the candidate option given the information known about the subject 120b and the current context of the subject 120b. For example, data about other subjects 106b may indicate that, for individuals that have similar attributes to the subject 120a (e.g., individuals of similar age, height, fitness level, or other attributes), and who have experienced the "decreased resting heart rate" condition, increasing monitoring and reporting of physiological data leads to improved health. This may be, for example, due to collection of more detailed or more comprehensive data, which allows for more accurate recommendations or greater engagement by the subject 120b. The computer system 110 may more determine which settings or changes to monitoring (e.g., adjusting which sensors, data types, collection frequencies, etc.) have led to improvement, in order to instruct corresponding changes for the device 102b. For the same group of other subjects 106b, the data may indicate that tracking sleep or altering exercise reminder schedules provided a moderate benefit but did not sufficiently improve results to warrant a change under the circumstances (e.g., context, as specified by the context data) of the subject 120b.

The computer system 110 does not necessarily perform any action, even if relevant candidate options for improving the state of the subject 120b are available. For example, if all of the available candidate options have scores that are less than a minimum threshold (e.g., indicating that the applicability, relevance, or benefit of the options is low), then the computer system 110 may choose not to perform any of the candidate options. Nevertheless, the computer system 110 can perform the evaluations again as new information is received, especially as the context of the subject 120b changes and potentially makes some of the candidate options more appropriate or beneficial.

In stage (C), the computer system 110 carries out the selected action 134b. In this case, the computer system 110 sends control instructions 107b to the device 102b over the network 111, instructing the device 102b to adjust monitoring and reporting of one or more types of data. For example, this may cause the device 102b to change the types of sensor data acquired and stored or to adjust the frequency or precision of measurement. This action is performed automatically by the computer system 110 based on its evaluation that the change will help improve the state of the subject 120b, for example, to provide information that would help improve the health and fitness of the subject 120b.

In stage (D), the computer system 110 sends selected outputs 132b and 133a to the client device 102b for presentation. Although the computer system 110 had many types of outputs that were determined to be relevant to the subject 120b and its classification, and even relevant to its current context, the computer system 110 provides only a selected subset for presentation. For example, the computer system 110 could provide raw data 121b, processed data 122b, and applied or actionable information 123b which are determined to be relevant to the subject 120b, its classification of reduced heart rate, and its current context. Nevertheless, the computer system 110 selects only a subset of those categories of information, based on determining that not all of the information would be beneficial to the user 104b. In this case, not all the categories of information 121b, 122b, 123a are provided (e.g., no raw data 121b is provided). Within the category of processed data 122b, not all of the potential visualizations or data types are provided either, with only a portion being selected for presentation. The computer system 110 can select this subset of the available and relevant data based on the information known about the user 104b and the current context of the user 104b.

Figure 2:
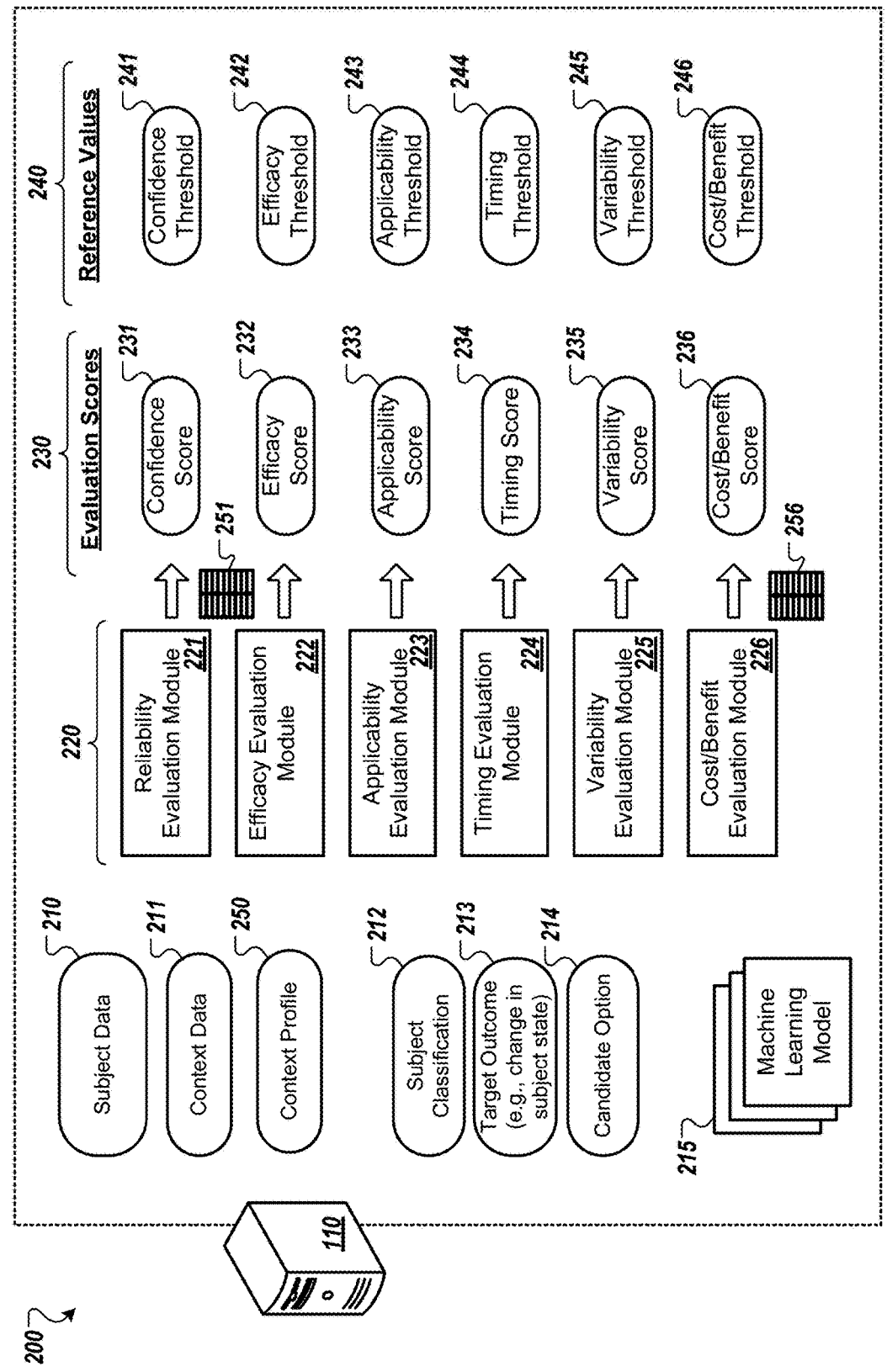
FIG. 2 is a diagram illustrating an example of a server system of FIGS. 1A-1B.

FIG. 2 is a diagram illustrating an example of the computer system 110 of FIGS. 1A-1B. FIG. 2 shows an example of processing by the computer system 110. The server can include analysis software 220 used to evaluate different aspects of potential actions to take or recommend for a subject. For clarity in illustration, the analysis software 220 is shown as various modules 221-226. Nevertheless, the various evaluation functions are not required to be performed by separate modules.

In the example of FIG. 2, a candidate option 214 has been identified as a potential option to initiate or to recommend for a subject. In some implementations, the candidate option 214 may be one of multiple options that the computer system 110 identifies as an option to improve the state of the subject. In this case, the computer system 110 is selecting and evaluating options to manage or assist the subject. In some implementations, the candidate option 214 is an option input to the system, for example, by a technician, a user, a doctor, a third-party computer system, and so on. In this case, the computer system 110 may validate or verify the appropriateness of an option selected by a person or system. This may be used to ensure the quality of actions performed for example to provide decision support to a doctor or patient to determine whether a proposed course of action is appropriate. In the example of FIG. 2, the analysis done for the candidate option 214 is prospective, performed in advance of recommending or carrying out the candidate option 214. Nevertheless, the same processing may be performed during or after the selection or carrying out of the candidate option 214. For example, in some cases, the techniques of FIG. 2 may be used to evaluate a history or log of actions to determine whether individual actions or a pattern of actions meet a quality and effectiveness standard.

Each of the modules 221-226 is used to evaluate a different aspect of the appropriateness of the candidate option 214 for a specific subject. The modules include a reliability evaluation module 221, and efficacy evaluation module 222, an applicability evaluation module 223, a timing evaluation module 224, a variability evaluation module 225, and a cost/benefit evaluation module 226. These modules 221-226 can each produce an evaluation score 231-236 which can be compared with a corresponding reference value 241-246. The comparisons between the evaluation scores 230 and the corresponding reference values 240 are used to ultimately determine whether the computer system 110 recommends and/or carries out the candidate option 214 for the subject.

The evaluation modules 221-226 can each use a variety of information for the subject. This includes subject data 210, which can indicate attributes of the subject, historical data for the subject, description of the subject, and other information about the subject from the database 112. The context data 211 can include data indicating the current and/or recent status of the subject and circumstances of the subject. For example, the context data 211 may indicate information reported by the subject, sensor data collected about the subject and its environment, data from devices associated with the subject, and so on, representing data acquired or conditions present over a certain time period (e.g., currently, over the previous five minutes, over the previous day, over the previous week, etc., depending on the implementation).

The subject classification 212 represents a classification for the subject. The examples of FIGS. 1A and 1B involve the computer system 110 determining the classification for a subject, but this is not required in all cases. The classification 212 may be determined by the computer system 110 or may be received from a user, extracted from records, received in communications of a third-party system, and so on. In some implementations, the computer system 110 uses a machine learning model 215 to determine a classification for the subject. For example, using information from the subject data 210 and context data 211, the computer system 110 may generate feature values as input to a machine learning model 215. The machine learning model 215 may process the input feature values and determine one or more classifications that are applicable to the subject.

The computer system 110 can also have data indicating a target outcome 213, which represents a desired result or change in the state of the subject. The target outcome 213 may be generated by the computer system 110, for example, based on the subject classification 212. For example, if the classification 212 indicates reduced performance or impairment of the subject in some way, a target outcome 213 can be set to represent improved functioning. In some implementations, the target outcome 213 is set by another system or by a user. For example, the target outcome 213 may represent a goal for the subject to achieve. If the subject is an individual, the target outcome 213 may be indicated by the individual (e.g., a personal goal) or may be set by a doctor, or may be set in another way.

The reliability evaluation module 221 evaluates the reliability of the classification 212 and of the data used to make the classification 212. If the classification 212 is incorrect (e.g., contrary to or not supported by the subject data 210 and context data 211), then taking action based on it would be improper. Similarly, if the subject data 210 and contact data 211 are incomplete or inconsistent, then the classification 212 is likely improper also. Thus, the computer system 110 can evaluate reliability on both of these levels, e.g., evaluating the quality of the underlying data and the reliability of the classification or inference made from the data.

For example, the reliability evaluation module 221 can assess the quantity, consistency, and accuracy of data about the subject. Not all of the data about the subject 210 needs to be assessed. The computer system 110 may identify the specific subset of the subject data 210 and context data 211 that were used to make, or are relevant to, the classification 212. When the computer system 110 determines the classification, it can use the algorithms or methods used to select the classification to identify the underlying data inputs to the classification determination process. In other words, the data that provides input to the analysis portion for the classification (e.g., the inputs relevant to that classification) can be selected for evaluation. Even if the computer system 110 did not determine the classification 212, the type of classification decision can be used to infer relevant subject data. The computer system 110 can store various tables 251 of data that indicate, for each of various classifications, the data types that are indicators or predictors for the classification 212. For example in the FIG. 1A example, the classification of high packet loss can be identified as depending on packet loss measurement data 121a. Similarly, in the example of FIG. 1B, the classification of decreased heart rate depends on heart rate measurements, e.g., heart rate data 121b. Other more complex classifications may involve multiple different types of data, potentially from different sources. For example, if the classification is that a person has diabetes, the table of classifications and corresponding related data can indicate that fasting plasma glucose (FPG) test results or A1C test results are typically needed.

With the set of data relevant to the classification 212 identified, the computer system 110 examines the data to determine if it is sufficient to support the classification 212. The data tables 251 can indicate, for each type of data relevant to the classification 212, the characteristics that are expected or needed to reliably reach the classification 212. This may include thresholds or ranges for various aspects of the data, such as expected or typical ranges of values corresponding to the classification 212, an amount of data needed to reach the classification 212, an amount of consistency among data collected (e.g., ranges within which a series measurements should fall), an amount of different data types needed (e.g., if only one of three types are needed, or if all three are needed), and so on. For example, in the case of a diabetes diagnosis, the data tables 251 may indicate (1) valid ranges for results from a FPG test generally (e.g., to allow impossible or clearly erroneous results to be identified), as well as (2) ranges for results of the FPG test that support a diabetes diagnosis. Similarly, data from the tables 251 may indicate similar information for the A1C test. The data in the tables 251 can also indicate that at least one of these two tests are needed, and that when results from both tests corroborate the classification a higher reliability should be given to the classification. With the reliability evaluation module 221, the computer system 110 evaluates the data about the subject 210 with respect to the standards set forth in the data tables 251. The result of the evaluation can be a confidence score 231 indicating how reliable the classification 212 is, taking into account how well the data 210, 211 matches the expected data profile for that classification 212 indicated in the data table 252. The confidence score 231 and other results can also be based on determinations about other factors such as whether the data 210, 211 is internally consistent, whether there are any conflicting or outlying measurements, and so on. The confidence score 231 and then be compared with a confidence threshold 241. The confidence threshold 241 can represent a minimum level of confidence needed in order to proceed with an action taken based on the classification 212. The confidence threshold 241 may vary depending on what the classification is. For example, a diagnosis of diabetes may require a higher confidence then a classification that the user experienced a temporary condition such as eyestrain. In some implementations, confidence thresholds for different classifications are indicated in the data table 252 to account for varying needs for reliability for different types of classifications.

The efficacy evaluation module 222 evaluates the predicted effectiveness of the candidate option 214 in helping the subject achieve or at least progress toward the target outcome 213. The efficacy evaluation module 222 can use the classification 212 and information defining the nature of the candidate option 214 (e.g., actions to be taken, pharmaceuticals to be prescribed, and so on), and the target outcome 213. For example, the module 222 can determine whether the actions of the candidate option 214 have assisted other subjects who have had the same classification 212 to progress toward or reach the target outcome 213. This can include analysis of historical data for various subjects, including looking at patterns of progressions of certain subject state characteristics over time and the actions performed for the subjects. In some implementations, the module 222 can evaluate data for a subset of subjects or cluster of subjects determined to have similar subject attributes and/or similar contexts as the subject currently under evaluation. As a result, the module 222 can determine whether the candidate option 212 has helped subjects in similar circumstances to the subject, and if so, what magnitude or degree of improvement resulted. By quantifying the likelihood of improvement and amount of improvement, the module 222 can then generate an efficacy score 232 that indicates how beneficial the candidate option 214 is expected to be for the current subject. For example, the score 232 may indicate a measure of the average magnitude of improvement for users in a cluster, weighted by the likelihood or prevalence of improvement among the users in the cluster. In the domain of health management and medical treatment, and the efficacy evaluation can assess whether the candidate option 214 provides the right treatment or therapy for the specific patient being considered. The efficacy score 232 can be compared with an efficacy threshold 242, which can indicate a minimum level of effectiveness required for an option to be considered appropriately effective for the classification 212 and target outcome 213. As with the other reference values 240 (e.g., references values 241-246, representing thresholds or other references), the value can be a default value, a value personalized based on data in a subject's context profile 250, a value dynamically determined based on the data about the subject (e.g., the classification 212, subject data 210, or other data), and so on. If the efficacy score 232 does not indicate at least a minimum level of effectiveness, then the candidate option 214 may be excluded or flagged as inappropriate.

In some implementations, a machine learning model 215 is trained, based on the examples of many different subjects, to be able to predict efficacy of different options in reaching certain outcomes. In some cases, a separate model may be generated for each type of classification or outcome to be assessed. In other cases, a combined model can be trained to predict effectiveness for multiple classifications, target outcomes, and options, and the model receive an indication of the relevant classification, target outcome, and options under consideration as inputs to the model 215.

The applicability evaluation module 223 is used to evaluate the applicability of the candidate option 214 for the specific subject. This can include determining whether the candidate option 214 is appropriate given the subject data 210 and context data 211 for the specific subject. Although the efficacy evaluation may indicate that the candidate option 214 is effective for subjects generally—or even for subjects determined to be similar to the current subject—the candidate option 214 may not be appropriate for this specific subject. To account for this, the module 223 can identify elements of the context data and subject data 210 that may indicate an increased or decreased applicability of the option 214 for the particular subject. For example the candidate option 214 may have been used before with the same subject, and the subject data 210 may indicate that good results were achieved before. The module 223 can use that data to increase the applicability or customized relevance of the option 214 for the subject. On the other hand, if the subject data 210 indicated that the same option 214 was used earlier and did not produce good results, or produced diminishing results over time, the module 223 can indicate that the candidate option 214 is less applicable than before. The module 223 can use that data to increase the applicability or customized relevance of the option 214 for the subject. As another example, the candidate option may indicate an action or element that may involve a pharmaceutical, but the subject data 210 may indicate that the subject is allergic to that pharmaceutical. As another example, the candidate option may indicate that certain actions or involvement by the subject is needed to carry out the option 214, but the context data 211 may indicate that the subject is busy and not able to devote the time or involvement needed.

In some implementations, genetics and genomics information may be used in the applicability analysis. For example, the system 110 may determine that, based on a person's genetic information, the person 90% more likely than average to be sensitive to a medication than other individuals. This can thus affect a score for the applicability of the medication.

The applicability evaluation module 223 generates and applicability score 233, which can be compared with an applicability threshold 243. As with the other evaluation scores 230 and corresponding reference values 240, the applicability threshold 243 can indicate a minimum level required in order to select or use the candidate option 214.

The timing evaluation module 224 can evaluate when the candidate option 214 should be carried out, for example, whether it is appropriate to carry out the action at the current time or at a later time, perhaps a scheduled future time. To make this determination, the module 224 can access the context data 211 to indicate the current activities and status of the subject, and determine if the actions of the option 214 would conflict with those activities. For example, in the example of FIG. 1A, the computer system 110 determined that the option of restarting the router would not be ideal given the current usage and traffic of the router. Similarly, if the subject is a person, the system can assess the calendar for the person, current activity data from a device associated with the person, location data for the person, and so on to determine if the candidate option 214 is appropriate for the person's current context.

The variability evaluation module 225 evaluates the range of outcomes expected if the candidate option 214 is carried out. For example, even though the candidate option 214 may be predicted to improve the state of the subject, there may be risks of undesired outcomes, and also the range of benefits may vary significantly from person to person. The module 225 can use examples where the candidate option 214 has been applied, and look at the range of results achieved, both in the short term and long term. From this evaluation, the variability evaluation module 225 can provide a variability score 235 indicating the level of uncertainty in the results of carrying out the candidate option 214. This analysis may take into account specific factors in the subject data 210 and context data 211 to customize the analysis for the specific subject. The variability score 235 may be required to be less than a variability threshold 245 in order for the candidate option 214 to be selected or recommended for the subject.

The cost/benefit evaluation module 226 can determine both cost of implementing the candidate option 214 and compare those with the benefits (e.g. likely improvement instead of the subject). For example, in the example of FIG. 1a, actions like restarting the router have costs in terms of making the router temporarily unavailable, disrupting current traffic, and so on. As another example, a patient being considered for surgery may be expected to incur costs of last time during the surgical procedure, last time during recovery, potential restrictions on activities, pain, risk of infection, and so on. The module 226 can identify these costs and quantify them, for example, using a data table 256 that associates different actions or options with corresponding costs or requirements. The data table 256 or other data can also indicate a weighting of different types of costs. The context profile 250 for the subject can also indicate custom weightings or adjustments to the cost calculations to customize the analysis. For example, a person who is retired may have greater flexibility and availability to visit a doctor's office then someone who is working daily, and so may have a context profile 250 indicating that the cost to attend an appointment or travel to an appointment is lower than for other subjects. In a similar manner to the identification and qualification of costs, the module 226 also identifies and qualifies benefits of the candidate option 214. This can involve using data from the data table 256 which can be generated based on examples in the aggregated subject data 114a/114b. For example, the costs and benefits can be determined based on longitudinal, population level data for many representative subjects of a given type.

Using the evaluation scores 230 and reference values 240, the computer system 110 may generate a composite or combined score for the candidate option 214. For example, the computer system 110 may apply weightings to the various scores 230 to generate the composite or combined score. This score may be used to compare with the scores of other candidate options, allowing different options to be ranked relative to each other. The weightings can be customized based on the context profile 250, which can customize the analysis for the specific subject or for the subset or cluster of subjects identified as similar to the current subject.

The computer system 110 can use the evaluation results in other ways. For example, the reference values 240 may represent thresholds that are required to be met in order for the candidate option 214 to be selected or recommend. As a result, if any of the evaluation score is 231-236 does not satisfy the corresponding threshold 241-246 (e.g., is above or below the threshold depending on the criteria that are set), then the candidate option 214 may be rejected. This may include, in some cases, indicating to the subject or to another system e.g. a third-party system that recommended the kind of option 214 or another person (e.g., a technician, doctor, or other person) that the option 214 is inappropriate. In some cases, such as for the timing evaluation, the option 214 may be determined to be inappropriate at the current time, but the computer system 110 may determine to apply the candidate option 214 at a later time or in response to detecting a change in the current context. For example, the computer system 110 may schedule the candidate option 214 to be carried out after a user completes an activity, or when the user reaches a certain location, or at a scheduled time in the future.

In general, the evaluations discussed with respect to FIG. 2 can be used to ensure that actions taken or recommended by the computer system 110 are providing a net improvement and benefit to the subject. This analysis weighs the strength of evidence for the classification 212 (e.g., reliability evaluation), the expected result of carrying out the option 214 (e.g., efficacy evaluation), the applicability of the option 214 for the specific subject (e.g., applicability evaluation), the timing for the option 214 given the subject's current context (e.g., timing evaluation), the variability or uncertainty in outcomes of carrying out the option 214 (e.g., variability analysis), and the relative costs and benefits of the option 214 for the subject (e.g., cost/benefit evaluation). This can help ensure that an action endorsed by the computer system 110 is based on the right classification, represents the right action to take (e.g., is likely to be effective), is appropriate for the specific subject, is taken at the right time, accounts for risks (e.g., by discounting scores for uncertainty levels), and on the whole provides benefits or utility greater than costs.

The various evaluations and scores 231-236 of FIG. 2 can be used to guide interactions with a user. For example, the applicability analysis may show that a patient has a 30% likelihood of having been exposed to lead. In response, the computer system 110 can generate a survey for the person, deliver it for display by a device of the user, and recommend topics for the person to discuss with their doctor.

The techniques of FIG. 2 can be used to determine the information provided to participants in research studies (e.g., clinical trials, pharmaceutical dosing trials, etc.), during the study and after the study is completed. This can be used to identify the relevant and useful information returned to them that they can discuss with, for example, their family health practitioner. In some cases, the computer system 110 can selectively provide information from the study to a patient's healthcare provider.

Many types of research can be performed such as generalized (e.g., observational) research and therapeutic research. The techniques herein can be used for both types as well as others. On the therapeutic side, the evaluation techniques can be used to determine if, for example, including a person in a study would represent a combination of the right drug, the right patient, and the right disease to provide a benefit. The scores and evaluations can be used to define a cohort, e.g., to identify candidates for whom the actions of a research study are a good fit and would be appropriately safe. In some cases, the techniques can be used to define a group for a sub-study, e.g., a subset of a cohort for a different intervention or interaction.

The techniques of FIG. 2 can also be used to selectively provide information to researchers running a research study or to support the study itself. Naturally, the researchers have different needs and interests than the study participants. The computer system 110 can be configured to use the information it collect to determine new surveys to send to study participants. For example, in this case, rather than weigh the potential benefits and costs with respect to the user alone, the system can also take into account the benefits and costs to the researcher. The computer system can identify information needed to complete a data set for the study, and then selectively initiate interactions (e.g., surveys, games, activities, requests for lab tests, etc.) with participants to collect the needed data and fill gaps. The computer system 110 can specifically contact participants identified as needing to provide a certain type of data, with interactions or requests targeted to the set of data needing to be collected. In some cases, this may not require any study participant interaction, such as when the computer system 110 causes a device of the study participant to increase sensing and reporting of data using a sensor of a phone, wearable, medical device, etc., and the computer system 110 can instruct this change directly.

In some implementations, participants in a study may use a web page or downloadable application to participate in the study or obtain information for the study. The computer system 110 may selectively unlock or make available different reports or interactive modules for different individuals, depending on the status of data gathered for each participant, the needs of the participants and what may benefit them, and so on.

In some implementations, the subject represents a group of study participants (e.g., a cohort), and the candidate option can be an action for the cohort or study as a whole. For example, the candidate option may be to change a parameter of the study, to extend the duration, to change medication dosing generally, etc.

In some implementations, the scores 231-236 or other measures can be provided for presentation, to provide visibility to a researcher and/or to a participant in a research study. The scores can demonstrate the value and benefit that is being provided by an individual's participation in a study, to the individual directly (e.g., through improved health monitoring, actual increases in health, etc.) and/or in general through advancement of knowledge based on the cohort as a whole. In some implementations, the computer system 110 can provide data for a user interface that provides an individual with his or her own results. For example, an individual may be taking medication and answering questions as part of a study. The computer system 110 can provide information and benefit to the user by showing results related to the participation, such as day-to-day scores of the items measured in the study being reported to the participant. Thus, the study can further engage individual participants by providing information that is relevant for them, but selectively tailoring the amount and scope for each participant as discussed in FIGS. 1A and 1B. For the researcher, information about the results of the study can be provided for individual participants and/or in aggregate for the cohort as a whole.

In general, information that the computer system 110 supports collection of for research studies can be provided at the level of individual study participants, for the cohort as a whole, or for a sub-group within the cohort (e.g., broken down by demographic factors, locations, status, compliance level with the study protocol, etc.). The computer system 110 can provide information that indicates, e.g., compliance levels, overall receptiveness for treatment, adverse effects, beneficial effects, and so on.

In many research studies, such as clinical trials, it is beneficial to monitor positive effects and adverse effects. The computer system 110, with its capability to store and analyze longitudinal data as well as context data, can perform this function. The computer system 110 can be configured to monitor collected context data to detect indicators of adverse events, for individual study participants and for the cohort as a whole. Similarly, the computer system 110 can monitor collected data to identify signs of effectiveness of study actions, such as to determine how well a the targeted therapeutic is working. While monitoring effectiveness, the system can evaluate whether any new risks being introduced. If the study is being run based on a protocol, the computer system 110 can store data indicating the elements needed for the study, a definition of adverse events, how to report adverse events, and so on.

The computer system 110 can monitor data for participants to determine how many participants are reporting adverse reactions and what the magnitude or severity of adverse effects are. The computer system 110 can store this information in a log and may also be configured to send alerts or notifications to researchers when adverse events occur. In some cases, the computer system 110 can be configured to provide results to an independent review board (IRB) when adverse events rise to a certain threshold quantity, severity, or type. In general, the computer system 110 may provide researchers a robust platform for detecting and reporting adverse events, allowing the person running the clinical trial to better manage their study. The platform can include a reporting option for a researcher to manually or automatically provide reports based on risks, events, and risk indicators determined based on data determined from study participants.

The computer system 110 can be used to provide information to clinical providers, such as doctors, hospitals, etc. Information collected during a research study for an individual can be provided, in some cases selectively depending on the needs of the individual and the provider.

While much of the analysis done by the computer system 110 can be done for analysis of prospective actions, the system 110 can also be used retrospectively to assess outcomes and determine whether outputs sent, actions taken, treatments prescribed or given, etc. met appropriate standards.

Figure 3:
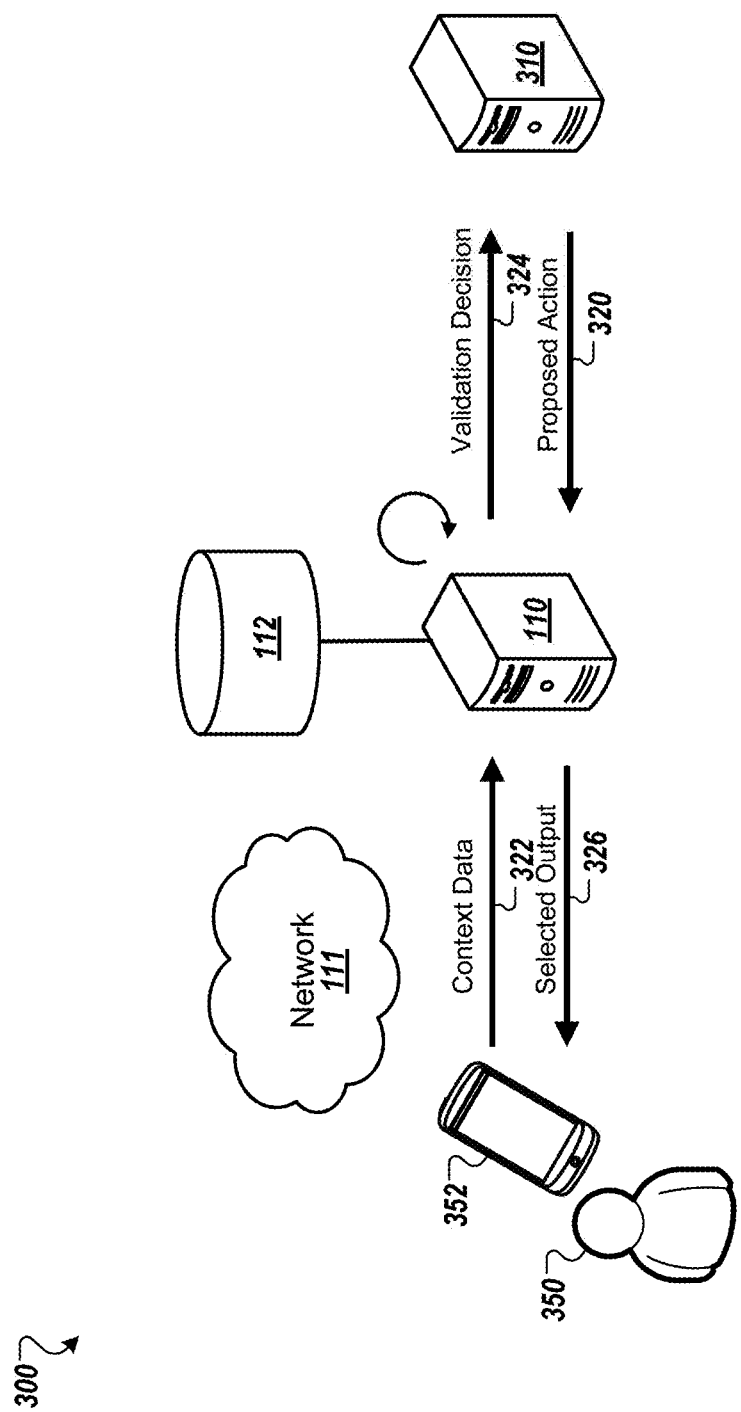
FIG. 3 is a diagram illustrating an example of a system for validating actions of a computer system.

FIG. 3 is a diagram illustrating an example of a system 300 that uses the computer system 110 to validate actions. In some cases, the computer system 110 can be used to evaluate the classifications or proposed actions of other systems. For example, a third-party computer system 310 may be used to manage or support a subject. In the healthcare field, the computer system 310 may be a computer system of a coach, nurse, doctor, insurer, researcher, or other party. The computer system 310 sends data indicating a proposed action 320, such as treatment for a subject 350, a therapy for the subject 350, a prescription for a pharmaceutical, an exercise regimen, a medical device, a digital therapeutic, or other intervention. The computer system 310 may also provide a classification for the subject 350, for example, a diagnosis or condition of the subject 350. The computer system 110 stores information about the subject 350 in the database 112 and also receives context data 322 from a device 352 associated with the subject 350. Using the information about the subject and the context data 322, the computer system 110 performs the evaluations discussed with respect to FIGS. 1A-1B and 2, to determine whether the proposed action 320 is appropriate for the subject 350 given the current context of the subject 350. The computer system 110 provides a validation decision 324 that indicates whether the proposed action 320 is approved or validated. If the computer system 110 does not approve the action, the computer system 110 can indicate the reasons (e.g., whether the classification was not considered reliable, whether the timing was not appropriate, etc.) The computer system 110 can also determine outputs to the device 352 using the techniques discussed with respect to FIGS. 1A and 1B.

Figure 4A:
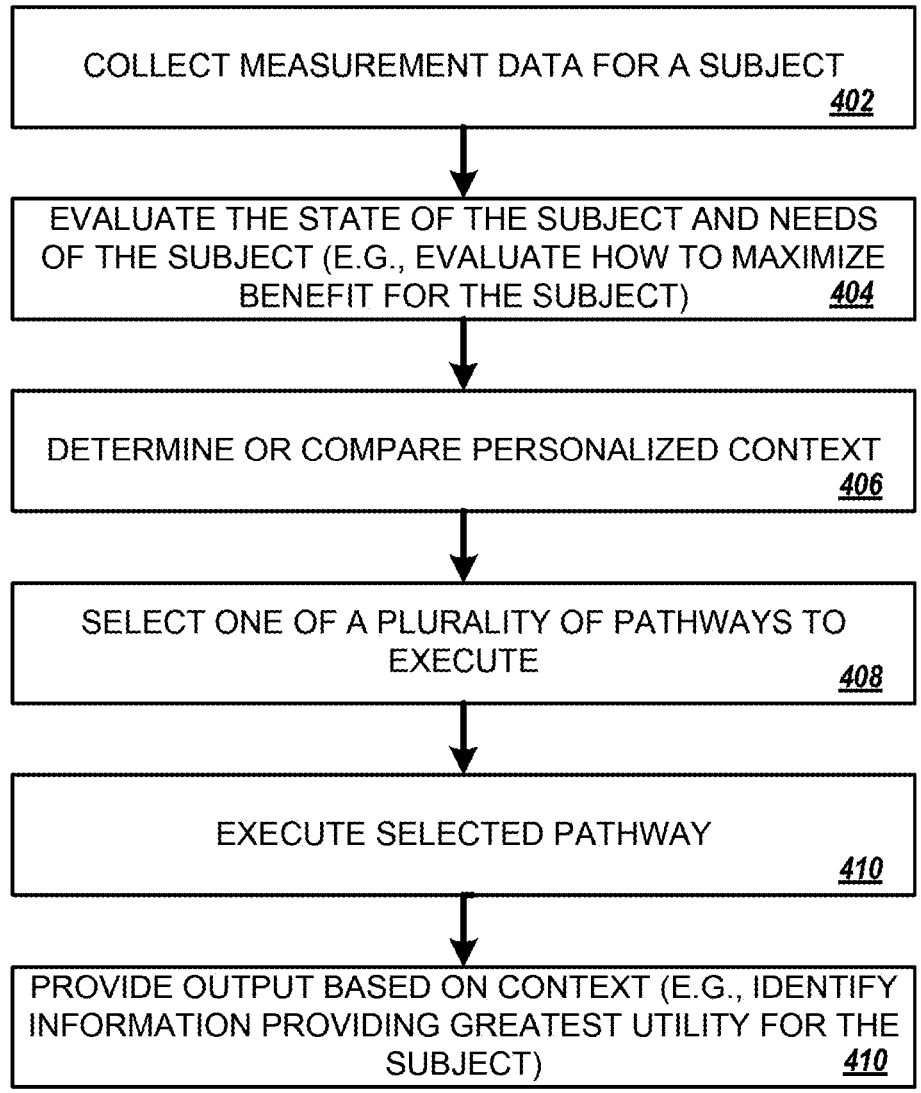
FIG. 4A is a flow diagram illustrating an example of operations performed by the server system.

FIG. 4A is a flow diagram illustrating an example process 400. The process 400 can be performed by one or more computers, for example, the computer system 110. In addition, or as an alternative, the process 400 may be performed by a client device, a collection of devices, a combination of processing between a server and client device, and so on.

The process 400 can be performed with the computer system 110 configured as a multi-tiered, multi-tenant system. The process 400 describes a single iteration for a single subject, but the process 400 may be repeated for the same subject, for different subjects, for subjects of different organizations, and so on. The process 400 can be used to maximize the benefit to the subject, for example, to improve a user experience for a user of a computing system, to improve the operation or condition of a device, to improve the experience of a patient or research participant, etc. In health care, there are four important factors affect the experience of a patient or research participant: safety, quality, personal satisfaction, and value. Value can represent a comprehensive measure of overall outcome with respect to overall cost (e.g., a composite of lost time, risk, foregone opportunities, financial cost, etc.). In some implementations, the analysis to determine appropriate output for presentation can evaluate which clinical and research information to return as part of the context-based analysis.

The process 400 includes collecting measurement data regarding a subject (402), evaluating the state of the subject and needs of the subject (404), evaluating a personalized context for the subject (406), selecting a pathway to be executed for the subject (408), executing the selected pathway for the subject (410), and reporting information selected for the subject (412).

In step 402, the computer system 110 collects data for a subject. Data can be collected through a variety of channels, including receiving data that is provided by the subject, provided by a device associated with the subject, provide by third parties, provided by sensors, and so on. For a subject that is a device, such as a mobile device, the subject may provide data directly over a computer network and other devices can also provide information about the subject. For a subject that is a person, such as an individual serving as a medical patient or a research participant, user input can be provided, e.g., to a phone, wearable device, computer, digital conversational assistant, or other system, and data can be obtained from other sources also. Data about many subjects (e.g., patients or participants) can be collected from disparate data sources that include: patient or participant provided information or outcomes; electronic medical records (EMR) or electronic health records (EHR); multi-omics including genomics (e.g., pharmacogenomics, genotyping, whole exome, and whole genome sequencing); measurement of bioassays and biomarkers from bio-specimens (e.g., blood, urine, saliva, or tissue biopsy). This data and other data collected about a subject can be stored in a database as characterization data for the subject, e.g., data that describes the attributes and activities of the subject. The characterization data can describe historical data for the subject, including a progression over time or series of measurements corresponding to different times.

In step 404, the computer system 110 evaluates the state of the subject and the needs of the subject. This can involve analysis to determine a classification for the subject. For example, the computer system 110 can receive or generate data indicating a classification that indicates a condition of the subject, for example, an undesirable condition that may impair the function of the subject (e.g., an error, a performance impairment, a disease or health impairment, etc.).

The computer system 110 can also receive or determine, based on the available data, a target state or target outcome (e.g., a desired outcome) to be achieved for the subject. For example, if the subject is classified as being in a condition of reduced performance or health, the computer system 110 can identify or confirm a desired target state for the subject to achieve in order to reach improved performance or health. The target state can be identified based on a number of types of records in the database 112, including records for the subject and other subjects. For example, the computer system 110 can use information about the subject's history to establish a baseline level of performance or health (e.g., a prior state or average state) as a target state. As another example, the computer system 110 can use the data in the database 112 to identify other subjects who have been classified with the same or similar classification of the subject. From the progression of the other subjects over time, and the states that the other subjects were able to achieve and the capabilities of subjects in those states, the computer system 110 can identify a target state that would provide an achievable improvement for the subject.

In step 406, the computer system 110 determines or compares a customized context for the subject. This can include generating or updating a context profile for the subject, where the context profile indicates how the characteristics of the subject affect the analysis of potential outputs to the subject and actions on behalf of the subject. For example, while the computer system 110 may be configured to perform the multi-factor analysis depicted in FIG. 2 (e.g., analysis of reliability, efficacy, applicability, timing, variability, etc.), the factors may need to be weighted differently for different subjects. Some subjects may be more sensitive to certain costs or problems, while some subjects may obtain different levels of benefit from the same types of actions and outputs. For example, certain users may be interested in viewing recent sensor data records, as evidenced by time viewing the information, requesting the information with user interface controls, and so on. Other users would find this to be a distraction and showing the data would reduce engagement and understanding. Similarly, even for a given user, the type and quantity of information may vary among subject (e.g., whether the user is viewing information about his Wi-Fi access point or his vehicle). The context profile can include weighting factors and preference data to indicate these user-specific or subject-specific parameters. With respect to the evaluations shown in FIG. 2, the context profile can customize functions or techniques for generating the evaluation scores, the reference values, and the manner of combining the results of different evaluations, thus indicating the differences among subjects and their circumstances. The context profile can include parameter values that specify adjustments to the analysis process (e.g., offsets, weighting values, scoring functions, threshold levels, etc.) that the computer system 110 can use to customize the evaluations of FIG. 2 and as otherwise described herein.

Frequently, the characterization data for a subject is of limited quantity or represents monitoring for a limited amount of time. As a result, the information collected about the subject alone may not be sufficient to determine the preferences, values, and needs of the subject, as well as to predict how the subject is likely to respond to or benefit from different actions by the computer system 110. To better adapt the evaluations to the particular subject of interest, the computer system 110 can use information about other subject to make inferences or fill in gaps in information about the particular subject. The computer system 110 can do this by clustering different subjects into groups or clusters, based on similarities among the subjects. The computer system 110 can use any of the information in the database 112 for this process, including characterization data and context data. Thus, the computer system 110 can cluster subject by similarities among one or more of: conditions or classifications of the subjects; attributes of the subjects; activities of the subjects; histories or patterns over time for the subjects; responses for the subjects; outcomes achieved by the subjects; inputs or preferences indicated by the subjects; and more. In this way, the computer system 110 can identify groups or clusters of subjects that have or have had similar attributes, similar problems, and/or similar contexts and then aggregate the data for the groups of clusters. For a particular subject, the computer system 110 can determine a distribution of the results of different outputs or actions for subjects in the cluster to which the particular subject is assigned. The computer system 110 can use this distribution, or other aggregated data from the cluster, to set preferences and parameters for the particular subject. Thus, if a certain action or output generally provided benefits to the subjects in a cluster, the context profile for an individual subject in the cluster can be defined or updated with parameter values to increase the likelihood or indicated benefit of the action or output.

In many cases, the preferences and relative benefits of different options are very different for subjects, even if the subjects have similar characteristics. The context of the subject and the relationships of the subject with people and devices can greatly vary from one subject to the next, and for a single subject over time. The context profile attempts to customize evaluation of potential actions based on inferences and analysis based on the data in the database 112. For example, a Wi-Fi router in a home and a Wi-Fi router in an office may perform essentially the same function, but there may be very different requirements in terms of quality of service, uptime, throughput, and so on. As a result, an action to restart an access point in a home environment may be acceptable where it may not be in the office environment. As another example, the timing of actions may be different, with maintenance actions for the router may be preferred in the day in the home environment but preferred in the evening in the office environment. When the subject is a person, there are various tradeoffs and weightings related to the values or beliefs of the individual, many of which may not be directly indicated by the individual. By assessing information about a cluster of similar individuals (e.g., records of their device interactions, behaviors, user inputs, etc.), the computer system 110 can better estimate or infer the likely characteristics and preferences that are shared to the cluster. The clusters of user can be considered "micro-cultures of meaning," for example, groups with needs or situations in common.

In step 408, the computer system 110 selects a pathway to be executed. This can include identifying candidate options for improving the state of the subject, evaluating the candidate options using the evaluations discussed with respect to FIG. 2, and selecting one or more candidate options that meet predefined criteria for applicability and benefit for the particular subject. As discussed above, this can include an evaluation of reliability or confidence in the data and classification for the subject, evaluation of the predicted efficacy of the option in improving the state of the subject (e.g., likelihood of improvement and/or magnitude of improvement), evaluation of applicability to the subject, and evaluation of the timing for performing the actions. In medical examples, this can include verifying that a patient has the right diagnosis, the right therapy and dose, and the treatment is appropriate for the patient.

In step 410, the computer system 110 executes the selected pathway that is predicted to benefit the subject. Execution can be conditioned on timing analysis, such as whether the current time is the appropriate time, given the most recent context information for the subject, to execute the pathway for the subject or if the action should be delayed or scheduled for a later time. This can include providing instructions and output to the subject directly (e.g., providing settings or control instructions to a mobile device, computer, control system, network infrastructure, etc.) This can also include providing instructions and output to other systems, e.g., third-party systems and so on. The actions to be performed are selected based on the sum of knowledge and actions for the patient and participant that can be gleaned from all data sources, e.g., individual provided information (IPI), individual reported outcomes (IRO), electronic health records (EHR)), bioassay(s), and genomics (and other-omics related data), any or all of which can be used to provide a comprehensive repository of individual data. As actions are performed on behalf of a subject, the computer system 110 continues to monitor the subject, track outcomes, receive context data, and update the characterization data for the subject.

In step 412, the computer system 110 provides output based on the overall data set for the subject, including context data indicating the current context of the subject. The computer system 110 performs curation, reporting, and return of information to provide output that is useful and understandable. The computer system 110 can use the context profile defined or updated in step 404 to evaluate the relevance of different types of outputs. The computer system 110 can reassess and optimize the information to be provided based on outcomes or changing context. Among other items provided for presentation, the computer system 110 can provide an indication of the current context of the subject, the classification for the subject, the actions taken to improve the state of the subject, and measured outcomes (e.g., measurements, potentially including sensor data, that indicates whether the selected actions have produced the desired effects). Depending on the outcomes measured, the computer system 110 can continue processing, for example, by repeating the process 400 to adjust the context profile, repeat the evaluations for different actions, and carrying out new actions and providing new outputs for the subject.

The computer system 110 can use machine learning and artificial intelligence to select the best action pathways for a patient. These techniques may also be used to identify appropriate interventions or interactions for a subject, to select outputs, and to select metrics to evaluate outcomes. In general, the computer system 110 can use machine learning to automatically optimize actions of the computer system 110, with feedback that adjusts outputs provided to subjects and associated users. Machine learning and artificial intelligence can also be used, based on observed outcomes and the data in the database 112, by the computer system 110 to make recommendations.

The computer system 110 can use unsupervised machine learning techniques and random forest models, which can provide advantages in reducing input preparation. Unsupervised training can create models that provide recommendations and predictors of areas where a subject is most likely to improve or have the highest risk in terms of setbacks. The computer system 110 can use the example data sets for different subjects from the database 112 as training data for supervised training that can generate predictive models.

Figure 4B:
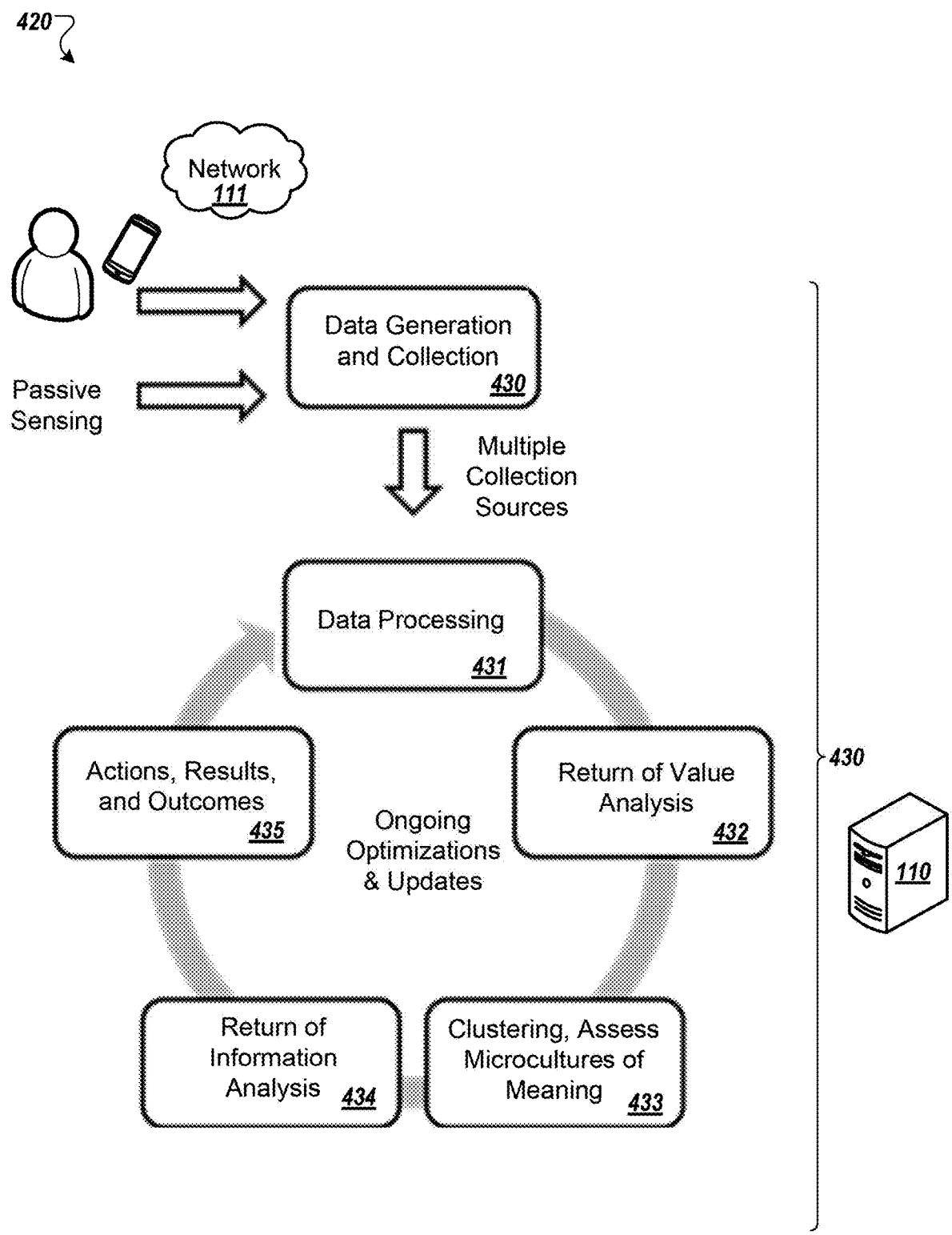
FIG. 4B is a diagram illustrating processing performed by the server system.

FIG. 4B is a diagram 420 illustrating processing performed by the computer system 110. FIG. 4B provides another way to visualize the actions of the computer system 110 and the ongoing updates and optimizations that can be performed for a subject. The example shows the dynamic nature of the process 430 performed by the computer system 110, and how the actions and outputs can evolve over time as data about the subject is continually refined with new information. The circular process can include machine learning and artificial intelligence techniques described above.

The process 430 includes generating and collecting data 431, including through reports of context data and passively sensed data from user devices, medical devices, and other sources. The computer system 110 performs data processing 432, for example, to update the database 112, determine classifications for subjects, set target outcomes, and so on. The computer system 110 performs return of value analysis 432, for example, the evaluations of reliability, efficacy, applicability, timing, etc. discussed with respect to FIG. 2. This can ensure that the actions performed, recommended, or endorsed by the server are likely to provide benefit to the subject. At the very least, the evaluations can ensure that the actions taken are safe and do not expose the subject to unnecessary risks or disruptions. The computer system 110 performs clustering and assesses microcultures of meaning 433. This processing can involve grouping users by the similarity in their attributes (e.g., demographic attributes, activities, medical conditions, locations, etc.) and their contexts. This information can be used to infer attributes, preferences, and values for the current subject based on the historical data of the other subjects identified as most similar. The computer system 110 performs return of information analysis 434, for example, selecting among the various types of output available (as discussed for FIGS. 1A-1B) to customize the content, formatting, and other aspects of output to the user. The computer system 110 then collects data about actions of the subject, results observed (e.g., through sensor data, medical records, user input, etc.), and outcomes with respect to targets for the subject 435. This newly acquired information is then processed in processing step 432, in which the computer system 110 can again update the database 112 and repeat the process 430 to evaluate and initiate actions on behalf of the subject and to selectively provide outputs customized for the context of the subject and the implicit and explicit preferences of the subject.

Figure 5:
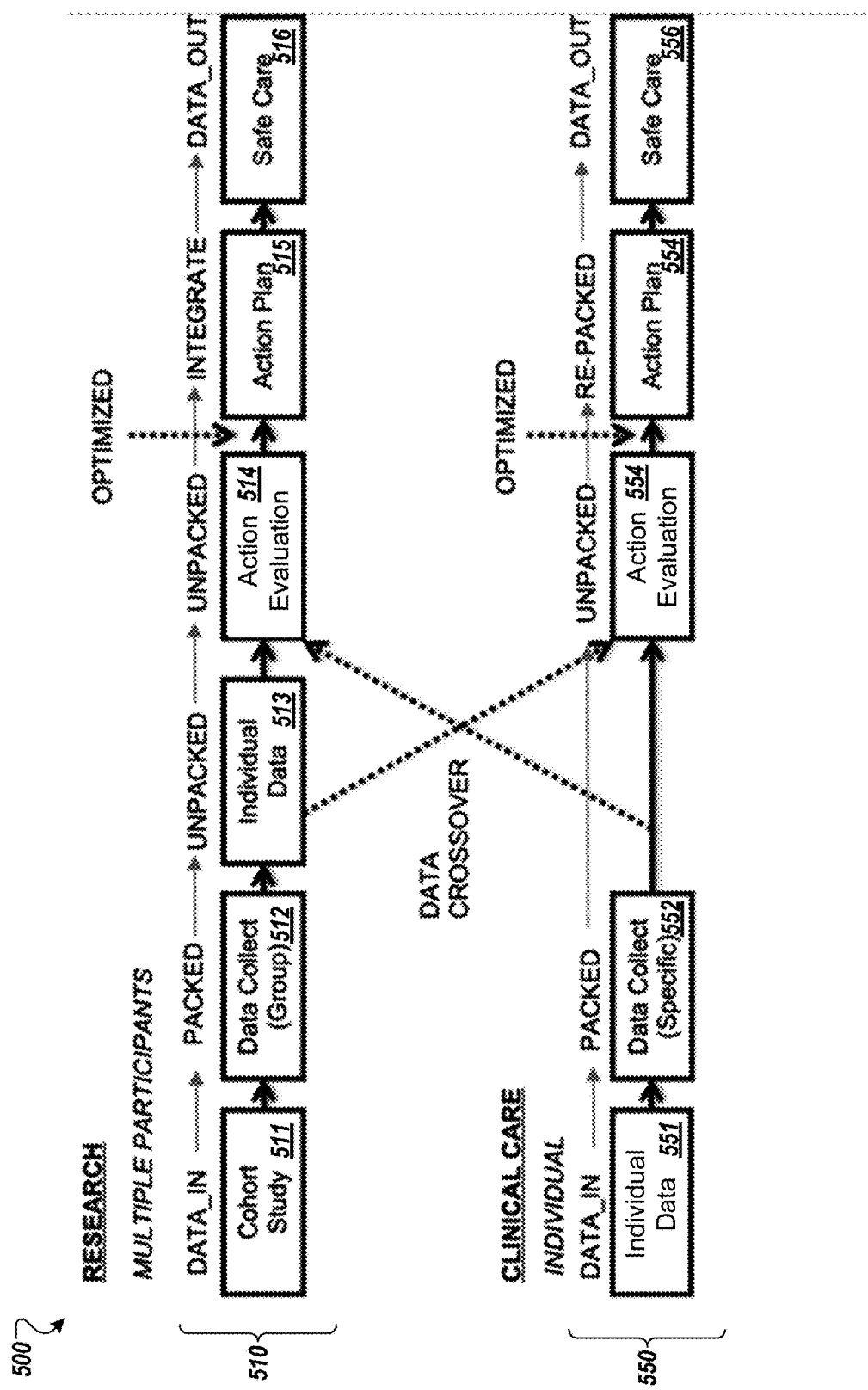
FIG. 5 is a diagram illustrating an example of data flow for customized context-based output.

FIG. 5 is a diagram illustrating an example of data flows 500 for customized context-based output. The example includes a first data flow 510 representing data collection and processing for multiple participants (e.g., a cohort) in a research study. The example includes a second data flow 550 representing data collection and processing for an individual in a clinical care setting. Information collected for a person as a clinical patient can be used in the research study, and information collected for the person in the research study can be used for the person in clinical settings.

In a cohort study, information is collected for each of a group of participants, for an research purpose such as to address a research question. By contrast, in the clinical scenario, a particular patient has a specific intake reason, and data is collected and evaluated with respect to the patient's specific diagnosis, conditions, or procedures. The actions of the data flows 510, 520 can be performed by the computer system 110. The actions may additionally or alternatively be performed by other devices, such as client devices, cloud computing platforms, or other systems, alone or in combination with the computer system 110.

The research data flow 510 includes a series of steps 511-516. In step 511, the cohort study is defined. The study is configured to use a specific marker or measurement obtained one or more data sources, e.g., surveys (e.g. family history), sensors (e.g. blood pressure), samples (e.g. blood) donated, and pre-existing information (e.g. EHR data). The cohort may include a wide variety of participants with varying backgrounds, demographics, age, ethnicity, gender, education, and family backgrounds.

In step 512, the data collected is "packed" as an aggregated group of information across the cohort and shared across studies, within the study, or otherwise planned to be disseminated.

In step 513, the aggregated data is "unpacked" for an individual study participant, and evaluations are performed to determine which outputs are most appropriate for the individual. This analysis can use the techniques discussed with respect to FIGS. 1A-1B. The analysis can be performed for each individual participant, so that the output to different study participants varies based on the set of information known about the participant (e.g., the participant's attributes, history, context, preferences, etc.). The information that is selected for an individual may be evaluated using the various evaluations discussed with respect to FIGS. 1A-1B, with only outputs that have at least a minimum score with respect to corresponding thresholds being provided. Steps 513-516 can be performed separately for each participant in a research study, to customize the actions taken and information provided for presentation for each participant individually.

In step 514, the unpacked data for an individual is evaluated using the evaluations discussed in FIG. 2 to select action(s) to perform for each participant in the research study individually. This can include identifying one or more candidate actions and evaluating reliability, efficacy, applicability, timing, and so on. In other words, the computer system 110 can determine whether actions are based on choosing the right diagnosis, selecting the right therapy (e.g., including type of therapy, medication selected, dose and dosage, etc.), verifying that the patient is the right one for the therapy (e.g., has the appropriate patient characteristics, background, and context), and verifying that the therapy is administered at the right time. This process can include identifying markers (e.g., predetermined combinations or sequences of measurements or other data in the participant data) that may indicate or corroborate that an action is appropriate for the participant. The action that is approved can then shared, e.g., with the participant, the participant's doctor, with researchers, or others involved. Information not available from the research study may be acquired from the patient in the clinical care scenario to supplement the data collected in the research study.

In general, the "dose" of a medication can include the amount of a pharmaceutical that was consumed, ingested, injected or otherwise received by a patient at a specific time. "Dosage" generally refers to the amount, quantity, and frequency at which doses are specified, scheduled or recommended over a gime period.

In step 515, data describing the validated or approved action to be taken is integrated into an action plan for the participant. For example, the action plan for the individual may be a treatment plan to address a medical condition, a training plan to increase performance, or another type of plan to reach a goal or target state. The computer system 110 can provide data describing the newly selection action, which has been selected to further the overall goal of the action plan or to otherwise maintain or improve health or wellbeing.

The selected action can be personalized for the specific participant, can be described in an understandable or intelligible way, and can be expressed in an actionable form. The personalization can mean that the computer system 110 selects different actions for different participants in the research study, for example, due to the different attributes, histories, and contexts of the participants. In addition, the form of output to each individual may be different, e.g., with customized content and formatting based on the preferences of the individual and the types of outputs that the individual has found useful previously (e.g., as indicated by explicit user feedback or implicit user feedback, such as increased usage or interaction). The action plan is made actionable by indicating actions that the individual can act on. For example, the information from the evaluations in step 514 can be set as specific recommendations or instructions for the individual to carry out (e.g., "Drink 3 more cups of water a day to avoid dehydration," "consider going to sleep a more consistent time (such as 10 pm)," "now would be a good time for a 15 minute walk outside," or "please take the 10 mg dose of your medication now"). In addition to or instead of providing general knowledge (e.g., "exercise can alleviate depression symptoms"), the action description can indicate a specific action for the user to perform to achieve a benefit for health or wellbeing. In some cases, the selected actions include changes that are performed automatically, such as instructions from the computer system 110 to a client device of the individual to change settings or configuration of the client device, e.g., by adjusting the settings of an application or other software on the client device. In some implementations, the data is made actionable by providing the user one or more interactive user interface elements that the user can interact with to carry out the selected action, such as to schedule a medical appointment, initiate a call with a caregiver (or friend, family member, or other call recipient), to start a survey or form for collecting input from the individual, to play a therapeutic game provided by the client device, to receive a digital intervention (e.g., a digital therapeutic or other content), etc.

In step 516, the action plan, which has been personalized, made intelligible, and made actionable, is then reported to the individual. The individual can be shown the updated elements of the action plan the next time the user views the plan. In some cases, the individual can be notified of the change to the action plan, e.g., by indicating the change in a message or through a prompt for the individual to view the updated plan that includes the changes. This can be done through a variety of ways, such as through a communication platform (e.g., e-mail, text message, phone notification, etc.) or through a user interface (e.g., an interface of a web page, a web application, a mobile device application, etc.). The recommendations made and actions taken on behalf of an individual represent safe care for the patient, being carefully customized for the user and taking into account the evidence-based evaluations in step 514 (e.g., assessing reliability of a diagnosis, efficacy of proposed treatment, applicability for the specific patient, appropriate timing, and so on, based on observed outcomes for a variety of individuals). In many cases, this process can avoid recommending or carrying out risky, unproven, unnecessary, and ineffective treatment actions.

The clinical data flow 550 includes steps 551-556, which can be performed by the computer system 110 and/or other devices. In step 551, upon an intake procedure, the patient has their signs, symptoms, medication, and current dosage recorded. Based on this intake, data collection needs are defined, for discrete follow-up data collection events (such as laboratory tests) and/or for ongoing or repeating data collection (e.g., through forms and surveys, sensors of the individual's phone or a medical device, etc.).

In step 552, the data collected is "packed" and represents information from lab results which may include, e.g., genomics, assays, blood results, imaging and examinations across varying physiological measures. This information may be self-reported or lab-based and is recorded within the EHR as structured or unstructured data.

In step 554, the data is "unpacked" and evaluated using the evaluations discussed in FIG. 2. This step can include the same actions discussed for the action evaluation 514.

In step 555, data describing the validated or approved action to be taken is integrated into an action plan for the individual. This can include the same actions discussed for step 515.

In step 556, the now personalized, intelligible and actionable plan is then reported and provide to the individual. This can include the same actions discussed for step 516. As noted above, the evaluations and checks performed can ensure that the actions and overall plan implement safe care for the patient, e.g., recommending and carrying out actions that have are expected, based on scientific and clinical evidence (including actual patient examples), to provide a net benefit for the current individual.

As shown in FIG. 5, information from the research data flow 510 and the individual clinical care data flow 550 can interact to provide better recommendations and care for individuals. There is a crossover of data between the research setting and the clinical setting, so that a research study participant's clinical data can be used to inform the action evaluation 514 based on the research study. Similarly, the collected data and findings from the research study can inform the selection of actions (step 554) in the clinical setting.

Figure 6:
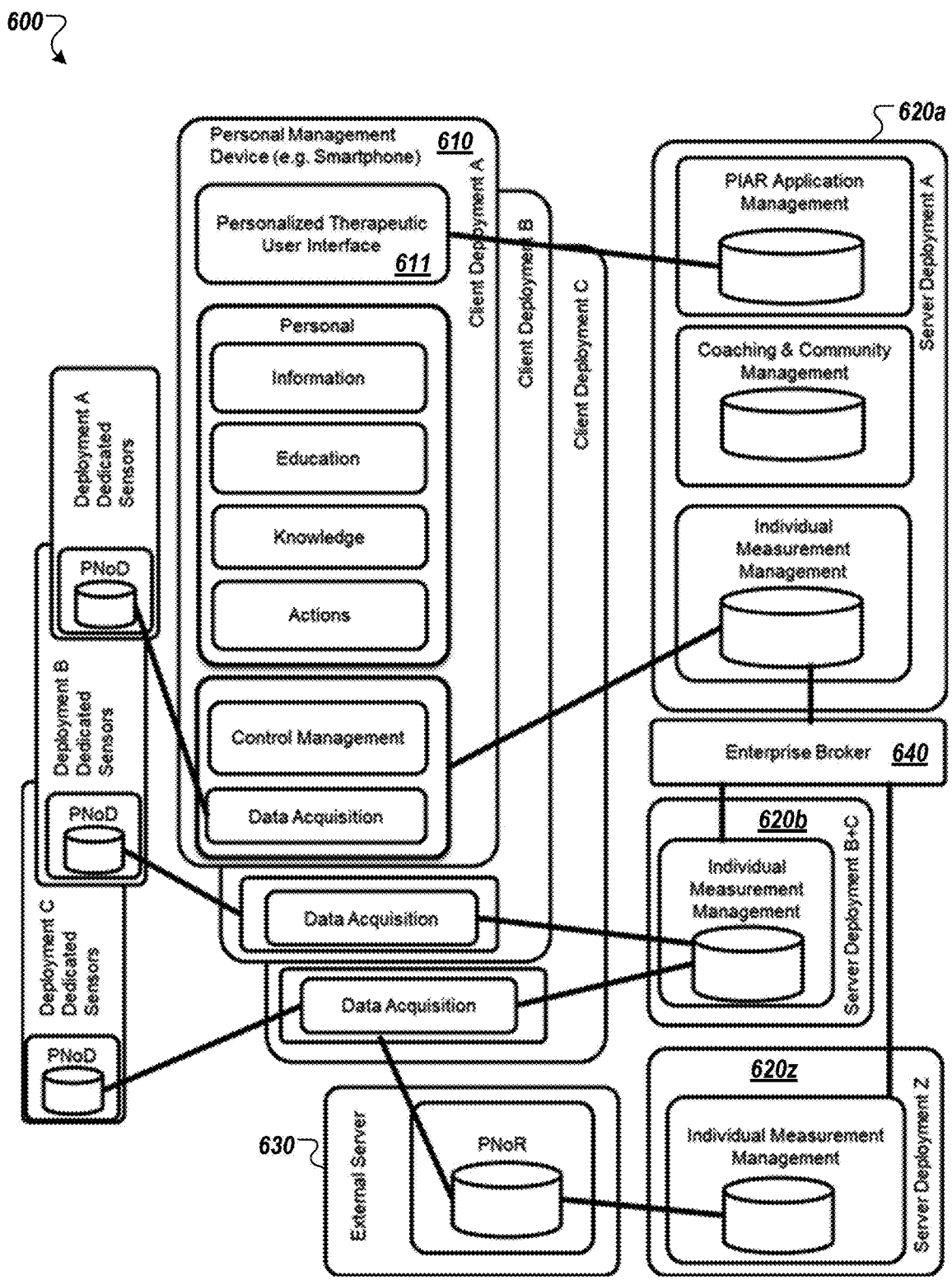
FIG. 6 is a diagram illustrating an example platform topology.

FIG. 6 is a diagram illustrating an example platform topology 600. The platform includes a user device 610, including a deployment of client software and associated data. The user device 610 may be any appropriate computing device, e.g., a phone, a smartwatch or other wearable device, a desktop computer, a laptop computer, a tablet computer, etc. Multiple different client software deployments (e.g., client deployments A, B, and C) may be provided for a single device or for different devices. These client deployments may represent, for example, different research studies, different health conditions being addressed, different clinical care providers, and so on. The platform includes server deployments 620a-620z which support data collection and delivery of output and therapeutics through the user device. The server deployments 620a-620z may use an external server 630 to facilitate data acquisition and may interact with an enterprise broker 640 to exchange information. The server deployments 620a-620z may individually or collectively implement the techniques described for computer system 110 above.

In more detail, for the user device 610, each client deployments indicates an installation of an application and/or configuration data on a personal management device for a specified user. In many cases, there would be multiple applications for the user each with a different purpose for data collection, observation, intervention and insights. Each of these specific purposes may communicate with multiple storage centers either locally or remotely connected by a server deployment 630a-630z. In some cases, user devices 610 can support multiple users each with their own personal data storage allocated as a user. As such, the application deployment is not specific to the device but the user.

The user device 610 provides a personalized therapeutic user interface 611. The user interface 611 is a delivery interface for recommendations and treatment actions selected for the individual using the evaluations of FIG. 2 and otherwise discussed herein. The interface 611 also receives and detect new data or requests input from the individual. The interface 611 can provide a combined solution to carry out data collection, observation, intervention, and delivery of analysis and recommendations. The user interface 611 is also responsive to the application management on the server (e.g., server deployment 620a in the example). The platform synchronization management between multiple deployments, users and their experiences is coordinated by the server to the mobile from a visual relevancy perspective.

The user device 610 can generate and store personal data 612, e.g., through the production and curation of information for each individual as it relates to a specific scenario or intervention. The information provides for effective return of information to an individual (e.g., contextually relevant and applicable information that is understandable to and actionable by the user), as well as return of value (e.g., actions and recommendations that are providing safe care and improving the state of the individual).

The user device 610 may have information about the user. Specifically, the user information 613 may describe the scenario or intervention for the user. Information 613 collected may include survey results (e.g., surveys related to a research question); health data (e.g., data about allergies, lab results, medication, health conditions, and EHR data); data from bioassays (e.g., information captured through blood, urine, or saliva test results); genomic information; and so on.

The user device 610 can provide an education pathway 614. Based on the user information collected, a pathway 614 representing a classification (e.g., diagnosis) and action plan is selected and provided. As the selected pathway 614 is carried out, the system collects results to measure progress. The pathway 614 can be determined based on the initial analysis of an individual, e.g., before a follow-up appointment in some cases, and may sometimes be provided as a prevention or learning pathway for improving health results or reducing risk of negative health results. The pathway 614 may include content from a content management system (CMS) such as videos, literature, audio recordings, and may collect scoring criteria for knowledge consumption/capture.

The user device 610 can provide knowledge 615 or processed inferences from the user information. This is the expected outcome of the pathway component and relates to the improvements or maintenance of specific characteristics related to health observations. It provides a scoring of the impact that such a pathway 614 may have on the individual and measures to what degree the success in providing such a pathway 614 or lifestyle changes impact the individual.

The user device 610 can provide an action component 616 that assesses actions for the individual. The action component 616 can collect data and perform processing to determine whether treatment was successful, and the individual has been treated appropriately. The action component 616 can communication with one of the server deployments 620a-620z to obtain this information also.

The user device 610 may perform various analysis and access functions related to the collection and management of individual data sources. In particular, the user device can manage the exchange of data between sensors 650 and the server deployments 620a-620z. This can include control management to perform higher-level management of the intake of sensor data. The control management can also specify and carry out delivery of sensor data, in coordination with of an intervention or specified goal. More generally, the user device 610 may manage data acquisition and data exchange for all user device sensors, e.g., internally, externally, and through sensor management systems and their counterparts.

Each client deployment on the user device 610 may use one or more sensors, e.g., some set of the sensors available on the user device 610 and potentially on other devices (e.g., medical devices, home automation systems, etc.). These sensors may be externally controlled, internally provided, or integrated through a web-related component. As such these are referred to as a personal network of devices (PNoD) and provide information related to the participant, e.g., in real-time or in a report at a predetermined schedule or manner.

The Server Deployment contains specifics to the PIAR Application Management, Coaching & Community Management, and Individual Management. The enterprise broker 640 manages multiple deployments through varying capabilities and exchanges related to ongoing individual measurement management. Each of these deployments 620a-620z may be involved in data collection, observation, intervention to individuals (e.g., delivery of therapeutics and recommendations), and determining and providing insights. They may be independent servers, or may be loosely or tightly coupled. External servers 630 can be referred to as a personal network of records, and may include servers like EHR-related servers connecting a disparate set of records related to the same individual.

Figure 7:
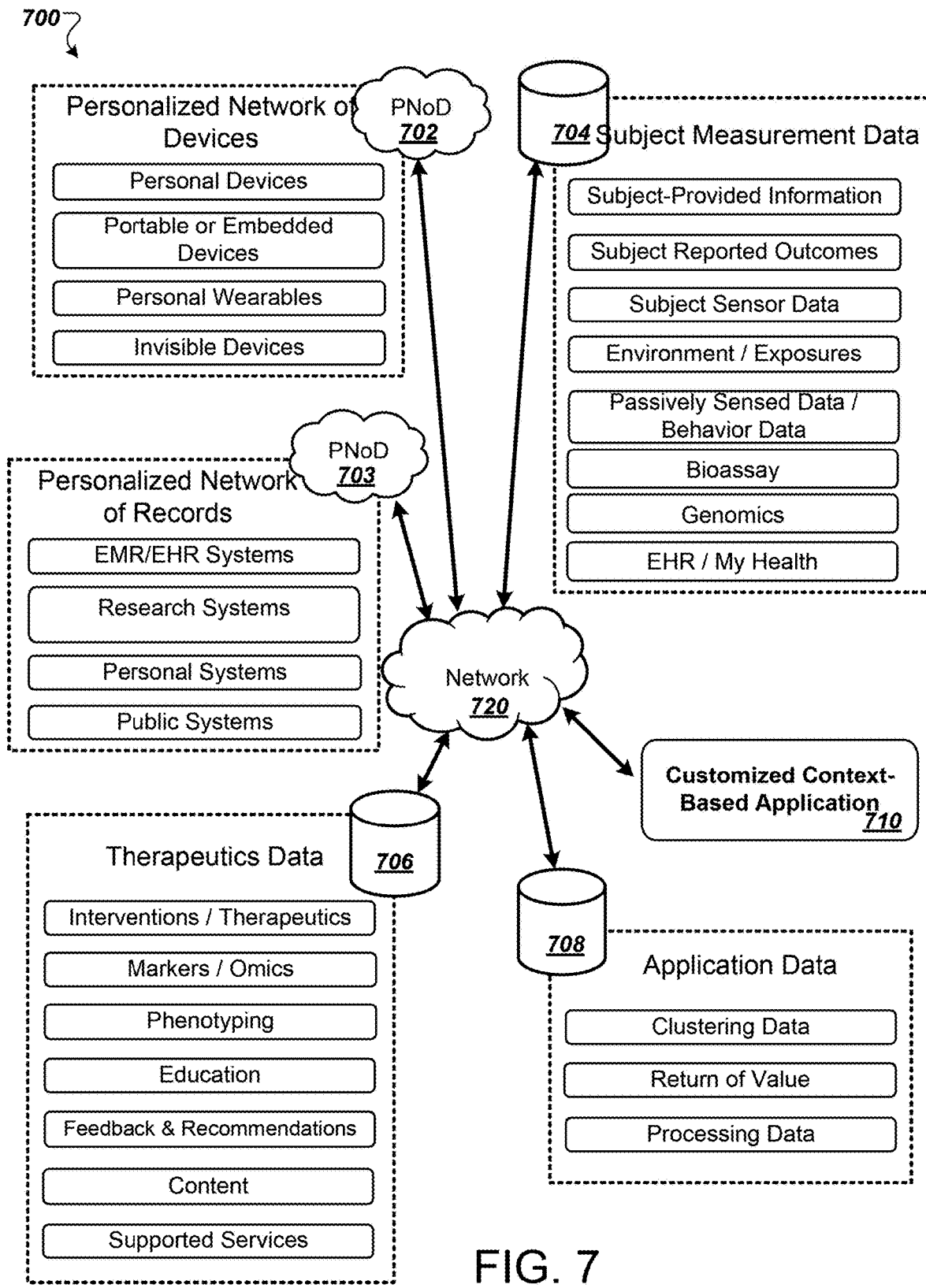
FIG. 7 is a diagram illustrating examples of data and devices interacting to provide customized context-based output.

FIG. 7 is a diagram illustrating examples of data and devices 700 interacting to provide customized context-based output. For example, the types of information that can be included in subject data 210 (and potentially context data 211) include data from a personalized network of devices 702, a personalized network of records 703, therapeutics data 706 generally, subject measurement data 704, and application data 708. All of these data sources can be used by a customized, context-based application, such as by the computer system 110 evaluating the information to determine actions to recommend or carry out to improve the state of a subject.

Figure 8:
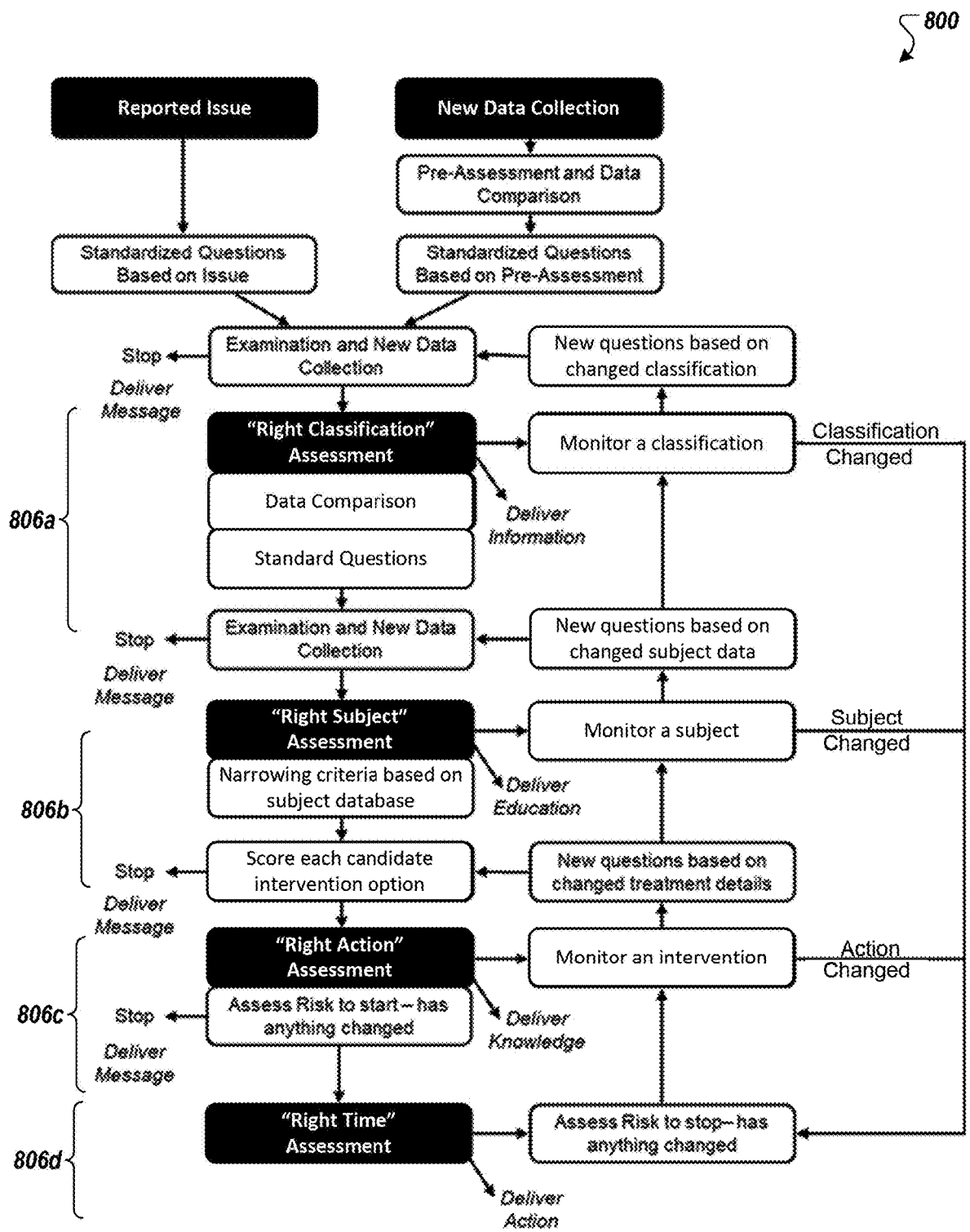
FIG. 8 is a flow diagram that illustrates processing for providing customized context-based output.

FIG. 8 is a flow diagram that illustrates a process 800 for providing customized context-based output. Generally there are two methods for acquiring information that begin the process. The first is a reported issue 810, in which an individual (such as a clinical care patient or research study participant) acknowledges a need (such as an ailment or potential ailment). The second is new data collection 820 that is independent of a specific, acute need. For example, the individual may be is enrolled in a program (e.g., general health maintenance, a research study) where the user provides information regardless of any need.

The individual may have expectations with the program to provide information, results, and overall value consistent with their original enrollment. In some cases, the individual may not expect the return of negative information (e.g., an indication of a diagnosis of a new disease or risks of ailments). Depending on the context, such information may be considered differently under the timing analysis.

The process includes data collection 802 for an individual, as well as an examination 804 (e.g., by a doctor), and the computer system 110 collects and monitors information on an ongoing basis. The process 800 includes feedback loops 806a-806d to respectively verify the right classification (e.g., diagnosis), the right subject (e.g., applicability to the individual), the right action (e.g., whether the treatment is correct), and the right time. Each feedback loop can involve an assessment to request more information. This can drive delivery of the updated information (e.g., "deliver message" after each assessment) for the individual and the doctor. The process can also respond to the needs of the patient, for example, to deliver information, education, knowledge (e.g., interpreted data), and ultimately to deliver an action (e.g., a treatment or other action) to benefit the patient.

An example is a change in dose of a medication. The doctor may prescribe a dose of a new drug to manage a condition. If the patient is receptive, then the dose can be changed. In a research setting, as part of a study, this may also occurs with the system used in the same way. One difference between a clinical trial and clinical practice is timing and risk-related monitoring. To facilitate research, the system 110 can include an observational scoring mechanism to determine effectiveness.

Information about the value or benefits of actions taken in a study can be provided as content to researcher, potentially as an ongoing outcome assessment during the study. This can indicate to the researcher whether the study is proceeding with results as desired. If adverse effects are detected, the system 110 can notify the researcher and assist to alert the correct agencies or review authorities. Information indicating adverse effects or increased risks may be provided to individual participants as well, allowing participants to better consult with their own physician regarding any adverse events.

Some studies allow for changing doses during a study. For example, a study may build in a period to re-evaluate dosages. A study may need to show effectiveness over 30 days. The study may proceed with individuals reporting outcomes for 30 days. If the desired level of benefit is not observed, the study may continue for 45 days to verify, and if no change, the dosage may be increased for another 45 days. Of course, if adverse effects are detected, the computer system can withdraw the affected participants from the study. Each of these changes, e.g., to increase a dose, to extend use beyond the initial 30 days, to begin the second period, and even whether to continue with an individual participant in the study, can be evaluated by the computer system 110 and either validated or recommended or disapproved. This is a similar process to the evaluation for clinical monitoring, e.g., a progressive analysis of changing a medication or dose, evaluating the effect, and then determining whether to take an action to move to a higher dose.

In some implementations, the computer system 110 generates information that is predictive for a research study cohort as a whole. For example, after or during a study for a medication at a first dose, a researcher may desire to understand if it would be beneficial to conduct a second study with a higher dose of the medication being used. Further, the researcher would want to know what type of people would be eligible or ineligible. For example, if a study with a 2 mg dose did not demonstrate effective results, the next attempt may be a study with a 10 mg dose. The computer system 110 may indicate that this increases risks for certain of the original participants, reducing the ability to include 50% of the original participants. Then, if dosage were increased to 20 mg, the computer system 110 may indicate that the set of available candidates may be reduced another 90%, resulting in only 5% of the original study cohort being eligible. This can show that, for example, in the final sub-study, the range of potential dosages of interest can be tested, but the original cohort size may need to be much larger to account for the attrition that occurs as dosage increases. The computer system 110 may also analyze the data sets to indicate the factors or risks that are related to ineligibility and indicate those to the researcher. This can allow the researcher to change the cohort recruitment parameters (e.g., cohort inclusion criteria) to focus on recruiting a set of individuals better suited for the higher dosage.

The analysis performed by the computer system 110 can be predictive of effects of different therapeutic options. For example, based on other tracked outcomes, the system can determine the probability that a drug and dosage is the right therapeutic for a particular patient given the patient's history. The computer system 110 also learns from recording and assessing the actual outcome after making the change. The system 110 may take into account a variety of factors for a holistic analysis. For example, increasing a dosage may increase the likelihood and magnitude of a positive effect, but only up to a certain point. In some cases, an increased dose may increase the target effect, but overall be a worse solution due to side effects or increased risks. The computer system 110 uses the analysis of FIG. 2 to assess these tradeoffs. This type of analysis is useful for clinical practice as well as for research, where it is important to measure not only whether the target effect is achieved but also whether side effects and risks have changed.

Figure 9:
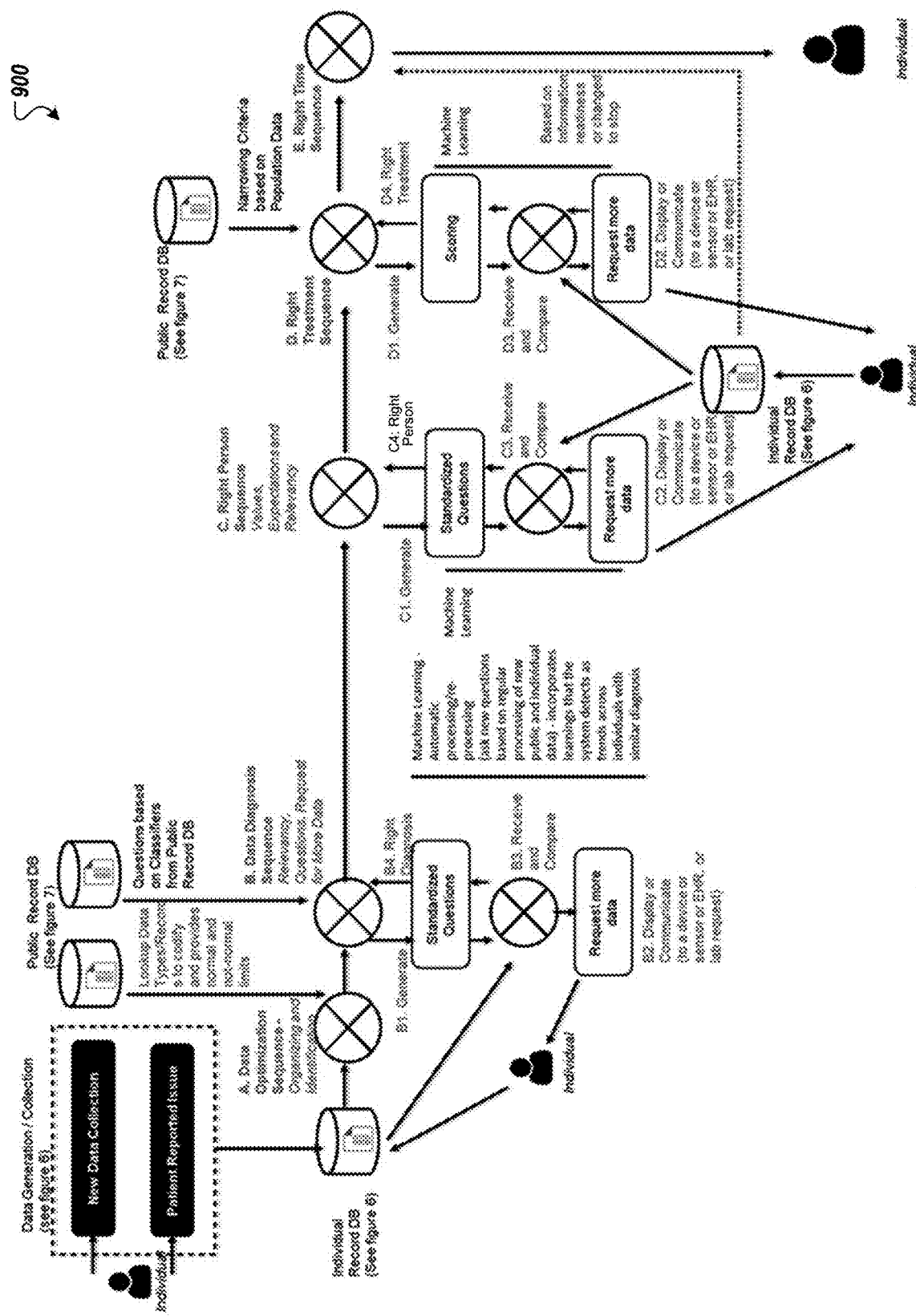
FIG. 9 is a diagram illustrating an example of data flow for customized context-based output.

FIG. 9 is a diagram illustrating an example of data flow 900 for customized context-based output. FIG. 9 show an example of a computerized process that shows an example of sequencing of various evaluations discussed with respect to FIG. 2. The steps described can be performed by the computer system 110 and/or other devices. The figure shows five main processes, denoted "A," "B," "C," "D," and "E," some with various numbered substeps. The five main processes include data collection and organization (A), classification and reliability analysis (B), an applicability or customization evaluation (C), an efficacy evaluation (D), and a timing evaluation (E). In any of these processes, the computer system 110 can use machine learning to automatically process or re-process data, including to identify topics or types of data needed, leading to new survey questions to the individual or new data requests from data sources. The machine learning can incorporate relationships learned as the system detects trends across groups of individuals that have similar diagnoses or are otherwise identified as having similarities.

The data collection and organization (A) includes organizing and identifying information. This can include looking up data types and records to standardize data, and to determine limits and ranges for what are normal and not-normal measurement values. This data can come from private data sources, public data sources, or a combination of both.

The classification and reliability analysis (B) can include a diagnosis sequence that determines relevancy of data, questions to ask the individual and/or doctor, and requests for additional data. This can include generating standardized questions or requests (B1), and displaying or communicating the requests for information to a device, e.g., to a sensor, an EMR/EHR system, a sensor, a user device, etc. (B2). The data received may trigger further requests for information from a database, from the individual, etc. The computer system 110 receives and compares the data (B3) with the limits or standards determined during step (A). The computer system 110 uses the information to verify whether the right diagnosis has been determined for the individual. If not, further information can be requested. If the diagnosis is verified, then the analysis proceeds to the next stage.

The applicability or customization evaluation (C) determines whether the individual has the right characteristics and context for the treatment. This can involve determining whether the person's values, expectations, and interests make the treatment relevant and suitable for the person. The computer system 110 generates requests for data (C1), displays or communicates the requests (e.g., to a user device, to a sensor, to a laboratory, to an EMR/EHR system, etc.) (C2), and compares the received data with data indicating standards for receiving the treatment (e.g., rules, indications and contraindications, data for others in a cluster or microculture of meaning for the individual, etc.) (C3). The computer system 110 then determines whether the treatment or other action is correct for the individual, and if so, proceeds to the next stage.

The efficacy evaluation (D) evaluates whether the treatment is right for the individual, e.g., whether the right treatment has been selected. This includes generating scores (D1) for the effectiveness of the treatment given the attributes of the individual, the context of the individual, outcomes of other individuals generally and/or those having similar attributes, and so on. If more information is needed to evaluate the potential effectiveness, the computer system 110 can display or communicate requests for information (e.g., to a user device, to a sensor, to a laboratory, to an EMR/EHR system, etc.) (D2), and then compare the scores to threshold or other reference values (C3). The computer system 110 determines whether the treatment being considered is the right one for the individual.

The timing evaluation (E) considers whether the current time or a scheduled time is right for the individual. If so, the computer system 110 recommends the treatment, provides information about the treatment, initiates the treatment, or takes other actions related to the treatment.

FIGS. 10A-10D illustrate examples of evaluation for customized context-based output. These figures follow an example involving assessment of a diagnosis and treatment for lead poisoning.

Figure 10A:
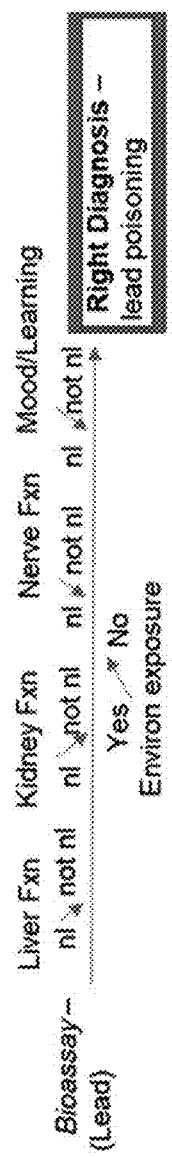
FIGS. 10A-10D illustrate examples of evaluation for customized context-based output.

FIG. 10A begins with receiving information about an issue, e.g., from a patient reporting a symptom or data being obtained from a blood test. If the patient reports an issue, such as leg pain, there are various steps that can be taken: a series of questions can be asked, an examination can be performed as a follow up to the responses, data can be requested and collected and compared with respect to standardized ranges and threshold, and a diagnosis or assessment is determined. In this case, the determination is that the individual may have lead poisoning. For the flow prompted by a lab report: a list of standardized question can be generated based on the limits exceeded in the data set from the lab results, answers to questions and lab tests may generate more questions, data can be requested and collected and compared with respect to standardized ranges and threshold, and a diagnosis or assessment is determined.

The example shows various questions that can be asked, about whether various body systems and observable characteristics are present. For example, the questions can ask whether the function of liver, kidneys, nerves, and mood regulation are normal or not normal (e.g., "nl/not nl").

Similarly the system can ask if there is environmental exposure to lead. These questions can be among may provided to a user, or can be the questions specifically selected when there is an indication that lead poisoning is a possibility (e.g., from blood test results). Either way, the results from the questions are used by the computer system 110 to confirm that lead poisoning is the right diagnosis for the patient. For example, the computer system 110 can have a data profile for the characteristics of lead poisoning, and can verify that the answers to the questions (and other data about the individual) are consistent with a lead poisoning diagnosis. This determination of a correct lead poisoning diagnosis leads to the next step shown in FIG. 10B.

In the example, the server can provide messaging to the individual to indicate the results that are determined, e.g., "There is a 90% chance that you have or will develop lead poisoning."

Figure 10B:
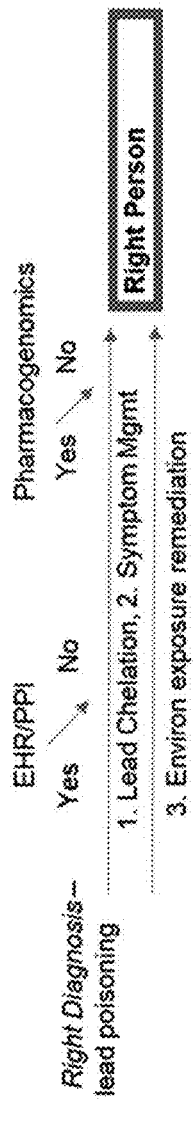

FIG. 10B show an evaluation of characteristics of the individual. Available treatments will allow a list of standardized questions and lab tests to be determined as pre-requisites for analysis. For evaluation of lead poisoning, one example is whether the person can tolerate chelation, e.g., will it improve the patient's condition or not. Other considerations include factors that may increase or decrease the effectiveness of treatment, cost (e.g., what the individual can afford), how symptoms need to be managed, and so on. These all are used to assess whether the patient has appropriate characteristics to receive treatment.

For this example, messaging to the patient can include educational materials. As an example, the computer system 110 may deliver a message for display such as, "Based on information provided, the lead result is based on environmental exposure and is causing the pain you detected in your leg. Lead exposure can be reduced by wearing proper gloves for protection, filtering air, selecting water from a clean source (such as bottled water), or changing your surroundings altogether. Lead poisoning can last several months when first exposed, and over time it can become more difficult to reduce the effects without medical attention."

Figure 10C:
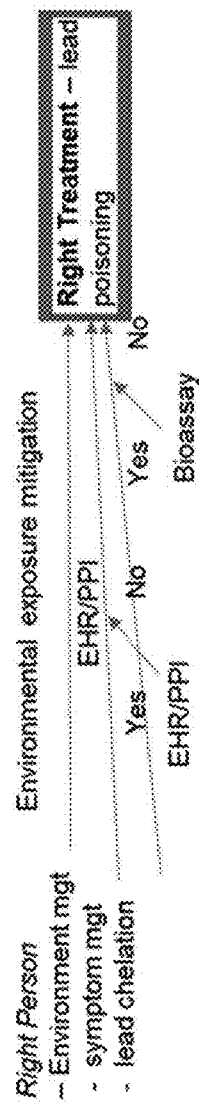

FIG. 10C uses various types of information to determine whether proposed treatment will be effective. Based on personalized tests and data, the computer system 110 needs to determine the right treatment to pursue. The computer system 110 can use population statistics, which may narrow selection or guidance to the range of options that have been shown to be effective. The computer system 110 can determine a score for each treatment option or opportunity based on the data collected. Even when a treatment calculated to be effective is selected, there are conditions where the status may change. For example, based on the desired outcome and continued observations, the analysis may be performed repeatedly to verify whether the data still confirms that the treatment is appropriate. Similarly, the desired outcome may be reconsidered based on the data, since new information may indicate other priorities or may alter the result that is expected. If measured outcomes are not providing the expected results, the computer system 110 may reassess the treatment's applicability for the individual. This may mean that the treatment is no longer the right one for the patient and a change needs to be made, such as increasing dosage. Additional assessments of the individual and his or her needs may need to be performed. The timing required can influence whether the treatment is right for the patient. For example, treatment that requires too long of a duration or wait for results may not be worth it for the individual.

For this example, knowledge is delivered to the participant on how to manage their condition. For example, a message to the individual may state, "to reduce the effects of lead poisoning, a combination of symptom management, environmental changes, and lead chelation are recommended. Symptom management recommended is to take a small pain medication to reduce the pain in your leg. Environmental changes recommended is to resolve drinking water issues in your home, and lead chelation based on your current observed levels and young age."

Figure 10D:
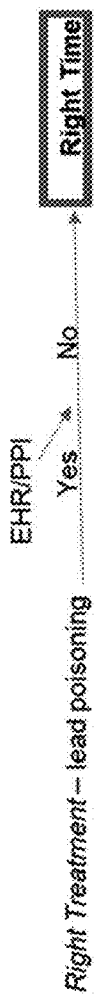

FIG. 10D the computer system 110 assesses timing for treatment. The computer system 110 needs to determine when is the right time to start, and when to stop (e.g., outcomes may not be achieved, pain increases, or changes in treatment will need to be re-evaluated). As treatment isn't risk free, the best solution may be to do nothing. The overall process may need to be restarted if the treatment is incompatible with the timing requirements of the individual or if the desired outcome is not achieved.

In the example, the recommended action is indicated to the participant on the events records. Medication is prescribed and the individual is requested to start immediately in sequence of environment remediation, symptom management, and lead chelation. The individual is recommended to revisit their status on a regular check-up to determine if changes are required.

Figure 11:
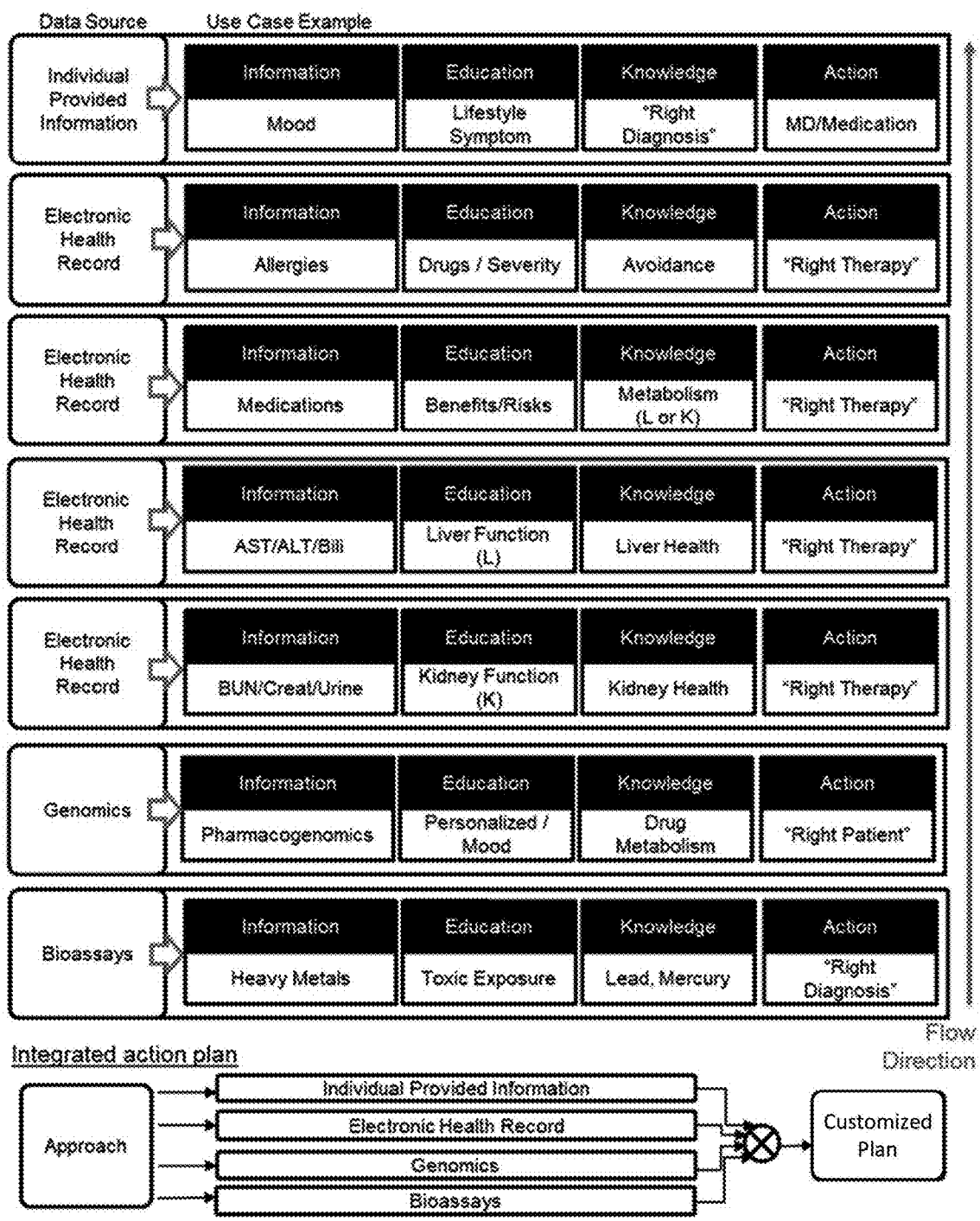
FIG. 11 is a diagram that illustrates an example of data sources and candidate actions that can be used to create a customized, context-based plan.

FIG. 11 is a diagram that illustrates an example of data sources and candidate actions that can be used to create a customized, context-based plan. Each row describes a different use case, across scenarios like mood, allergies, medications, liver health, kidney, health, drug metabolism and toxic exposure. Each example shows how a data source (e.g., individual provided information) and a use case (e.g., mood) can be used by the computer system 110 produce actions and outputs, e.g., providing information about the use case (e.g., mood information collected), information for an education pathway (e.g., education about healthy lifestyle and interpreting symptoms), knowledge (e.g., indicating to the patient that the current diagnosis is correct based on the collected data), and an action to perform (e.g., to visit a doctor and/or take a mediation).

The information from various data sources can be used to generate an integrated action plan. The combination of processing for each data source produces the comprehensive outcome of "safe care." Each example element has a dependency and is summed, with the combination of all actions to deliver the needs of each of the evaluations (e.g., right diagnosis, right patient, right therapy, right time) to achieve the desired outcome. For example, all of the data sources and examples may be used in the example of assessing lead poisoning. Bioassays can provide information that heavy metal exposure occurred and educational materials and knowledge about the topic can be output to the individual. The action based on the bioassay data can be to confirm that lead poisoning is the right diagnosis. This leads to the next data analysis step, involving genomics, in which pharmacogenomics is used to determine whether the patient is an appropriate candidate for lead chelation, e.g., whether it would likely be safe, effective, and well-tolerated (e.g., with only minimal or acceptable side effects). The result from this is a verification that the patient is the right kind of patient for lead chelation therapy. The electronic health record data is then used to assess lab test results, medications, and allergies to verify that lead chelation is the right therapy for the individual. Finally, information provided by the individual can confirm, among other things, that the diagnosis is correct and that the individual's input is consistent with the lab results, and then the action of performing lead chelation (as well as doctor visits, follow-up actions, etc.) with appropriate medication and dosage, is added to the customized plan for the individual.

Figure 12:
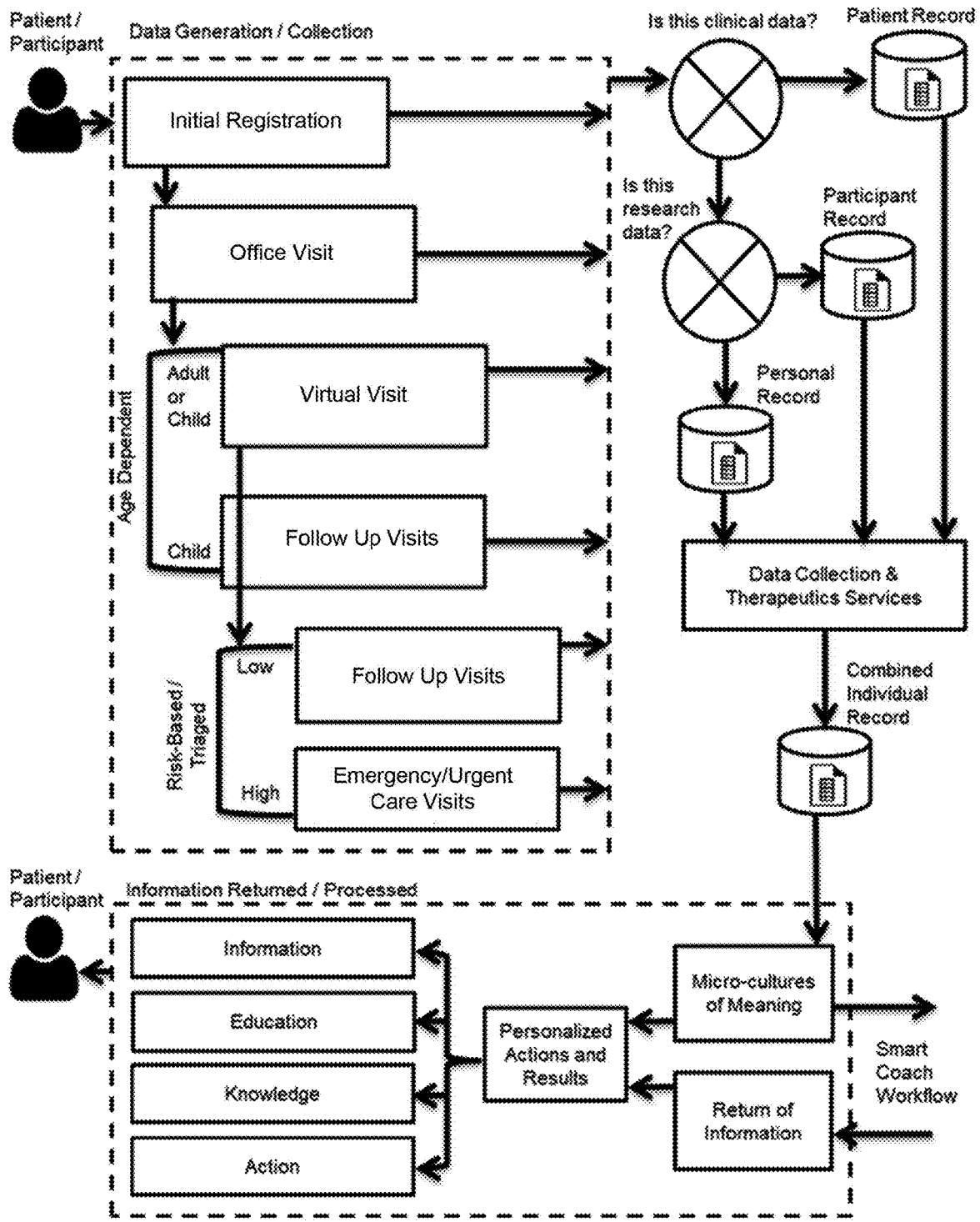
FIG. 12 is a diagram that illustrates an example of processing to use and manage data received about a subject.

FIG. 12 is a diagram that illustrates an example of processing 1200 to use and manage data received about a subject. The figure describes an individual workflow as a patient and participant for the collection, curation, and return of information and return of value. Data collection happens through many paths based on clinical workflows, research workflows and individual collection outside of these. As such, the data collected needs context that is ingested into the context framework. Data is coded and marked based on events that occurred to the individual that prompted the collection or ongoing collection of the data.

In the upper right section of the diagram, clinical data and research data can be identified and saved to separate clinical and research records. Both types of data can be provided to the data collection and therapeutics services provided by the computer system 110, which may have a combined record for the individual. The computer system 110 uses information about other individuals identified as similar, e.g., in similar micro-cultures of meaning. The computer system 110 generates personalized actions and results, and then selectively provides different levels of information to the individual based on the current needs and context inferred for the individual.

Figure 13:
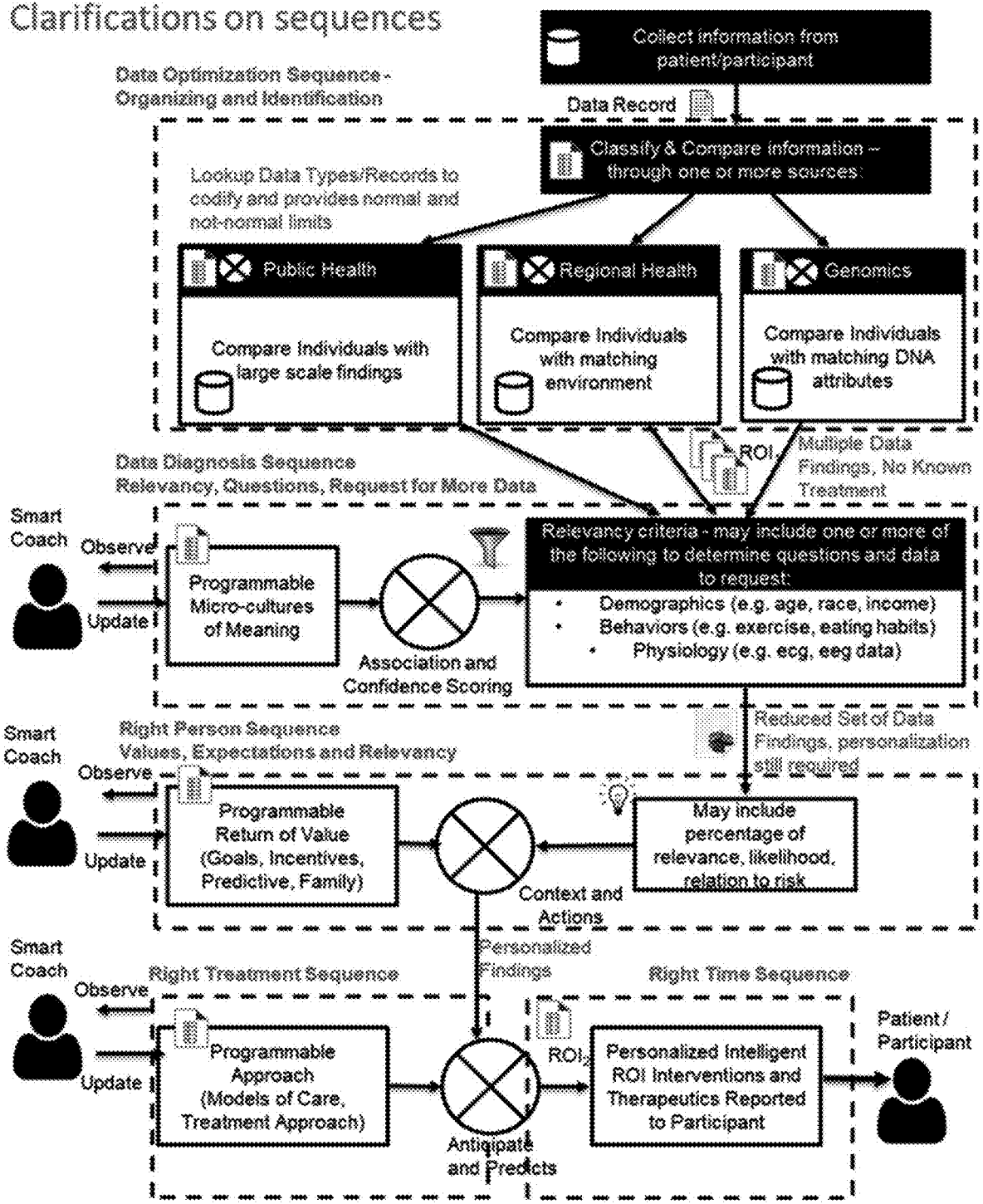
FIG. 13 is a diagram that illustrates an example of various data sources and evaluations using information from the data sources.

FIG. 13 is a diagram that illustrates an example of various data sources and evaluations using information from the data sources. The figures shows a smart coach workflow for intervention and return of information and value to the individual. The sequence takes the collected therapeutic data and follows an approach to repeatedly optimize, personalize, optimize, personalize, and so on. The "smart coach" can be a service provided by the computer system 110 or by a person aided by the tools the computer system 110 provides.

During the first optimization sequence, a first order information output is generated after classifying and comparing data through sources like public health, regional health and genomics. The first order information output is then compared, associated, and scored against programmable micro-cultures of meaning (e.g., information determined for a group or cluster of users determined to be similar to the current individual being evaluated). This, in turn, generates a reduced set of findings as a second optimization sequence which may include percentage of relevance, likelihood and physiology and context and actions. The output of which creates a second order return of information which, through the programmable models of care, allows the system 110 to anticipate and predict needs and actions to meet those needs. This ultimately provides a personalized output to return to the individual, participant, or patient.

FIGS. 14-17 illustrate examples of user interfaces for managing and providing customized context-based output. The client application interface could be a single application or multiple application supporting one or multiple features related to interventions. The application shows features related to multiple measures related to an intervention or prevention program. Within the measurements, there is the ability to track personalized reports, action plans and predictive trends in a health impact assessment to the individual.

Figure 14:
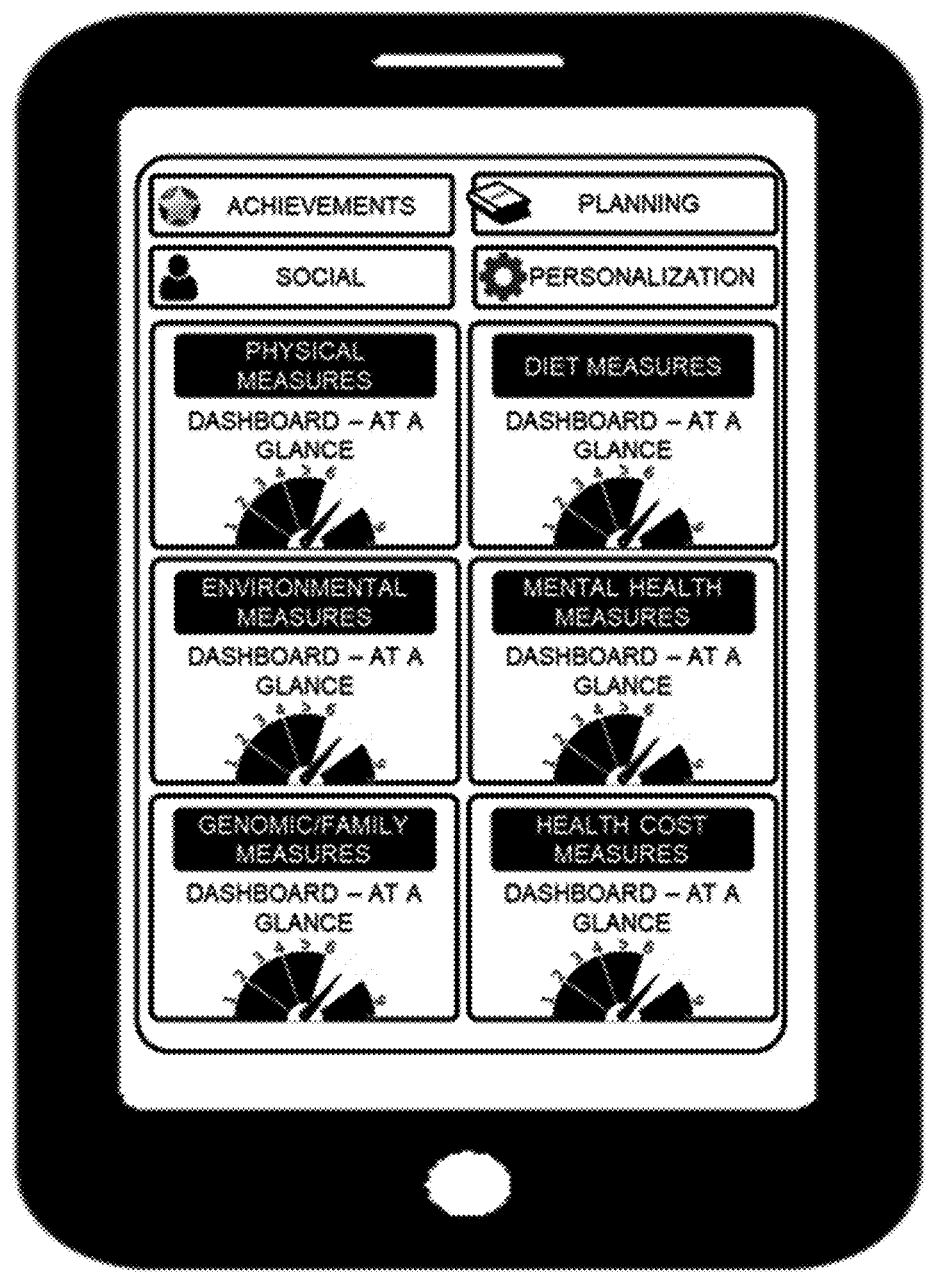
FIGS. 14-17 illustrate examples of user interfaces for managing and providing customized context-based output.

FIG. 14 shows a client application dashboard example 1400 to show to an individual (e.g., patient or research study participant). This can be an example of a user interface that may be shown to an individual to indicate, for example, scores for the individual for different tracked measures (e.g., physical measures, diet measures, environmental measures, mental health measures, genomic or family measures, health cost measures, etc.)

Figure 15:
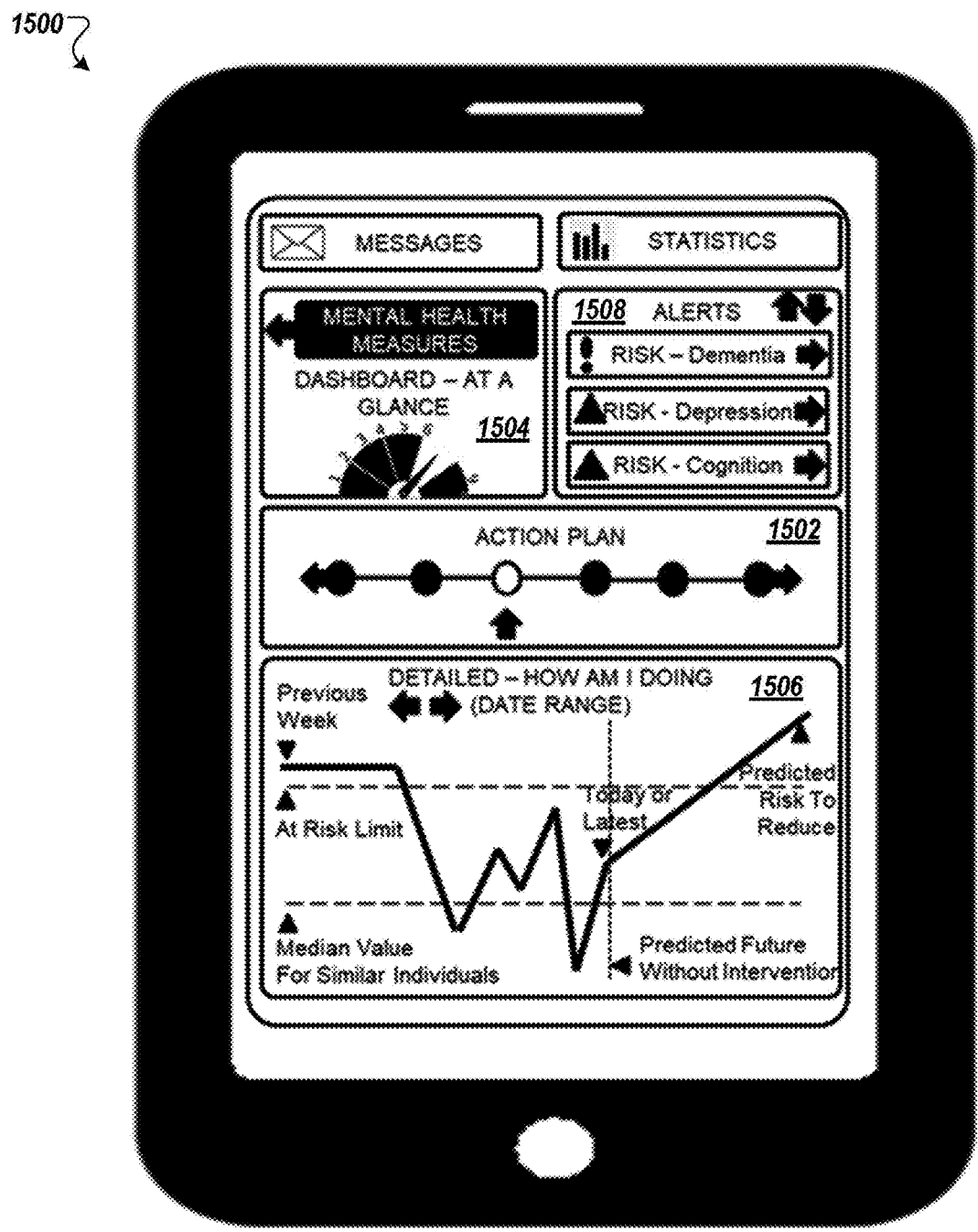

FIG. 15, shows a client application detailed view 1500, including an indication of progress along an action plan 1502, tracked or measured data 1504, and predictions about future risks and expected results 1506, including a history of risks or prognosis over time, and alerts (1508) of conditions or health areas that need attention, which the user may select to obtain more information.

Figure 16:
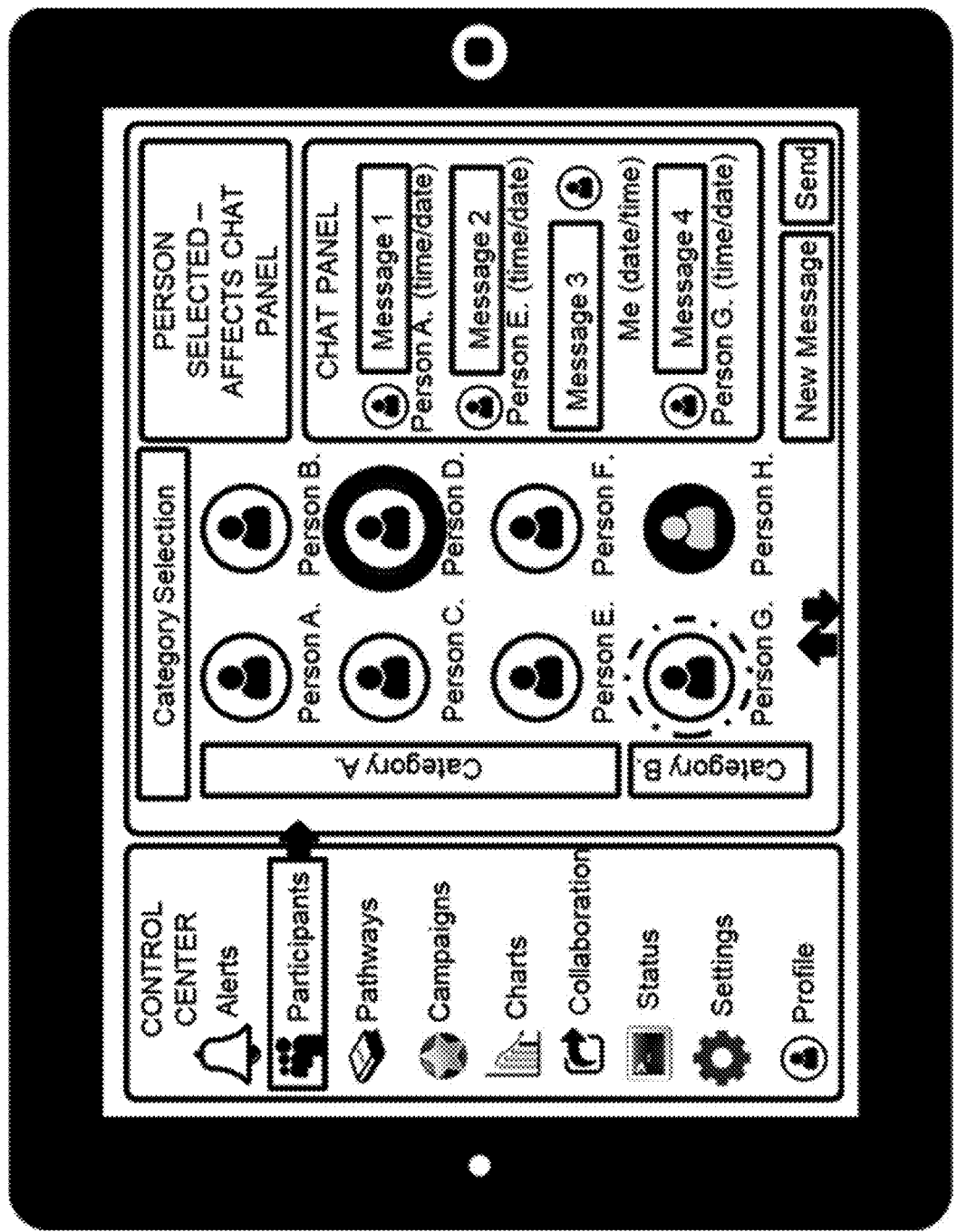

FIG. 16 shows an example of a dashboard interface 1600 for a coach or caregiver, e.g., for a someone who is helping support multiple different individuals. This interface could be a single application or multiple application supporting one or multiple features related to interventions. The figure shows visualizations of participants, shown based on categories and indicators that help identify when risks or changes occur. In the interface 1600, there are controls to select an individual to communicate with that individual or find out more about the status of that person. There is a messaging panel (e.g., "chat panel") that allows communicating with participants as a group or as individuals. When the user selects a different person, the interface loads a message thread for the selected person.

Additionally, the coaching application may provide features for the following areas.

Alerts—Messaging alerts from individuals, groups, started or completion events, and system notifications.

Participants—Ability to communicate and interact with specific individuals or groups of individuals.

Pathways—a journey or a work flow process. A coach may have 1 or many interventions which can be described through pathways (additional information on this is see in FIG. 9).

Campaigns—A coach may have a set of goals for a group or an individual which may offer rewards or virtual awarding opportunities to individuals and sponsor engagement and activity above and beyond ROI/ROV.

Charts—A coach may have charts that show overall progress of individuals, groups, segments, success rates from group to group.

Collaboration—Ability to work with other coaches and co-manage groups and individuals when required such as distributed support groups and time off/holidays.

Status—Includes overall auditing and health of network services.

Settings—Configurations to the overall application, reporting notifications, email digests.

Profile—Configurations to the given coach, passwords, email, details visibly available to other individuals.

Figure 17:
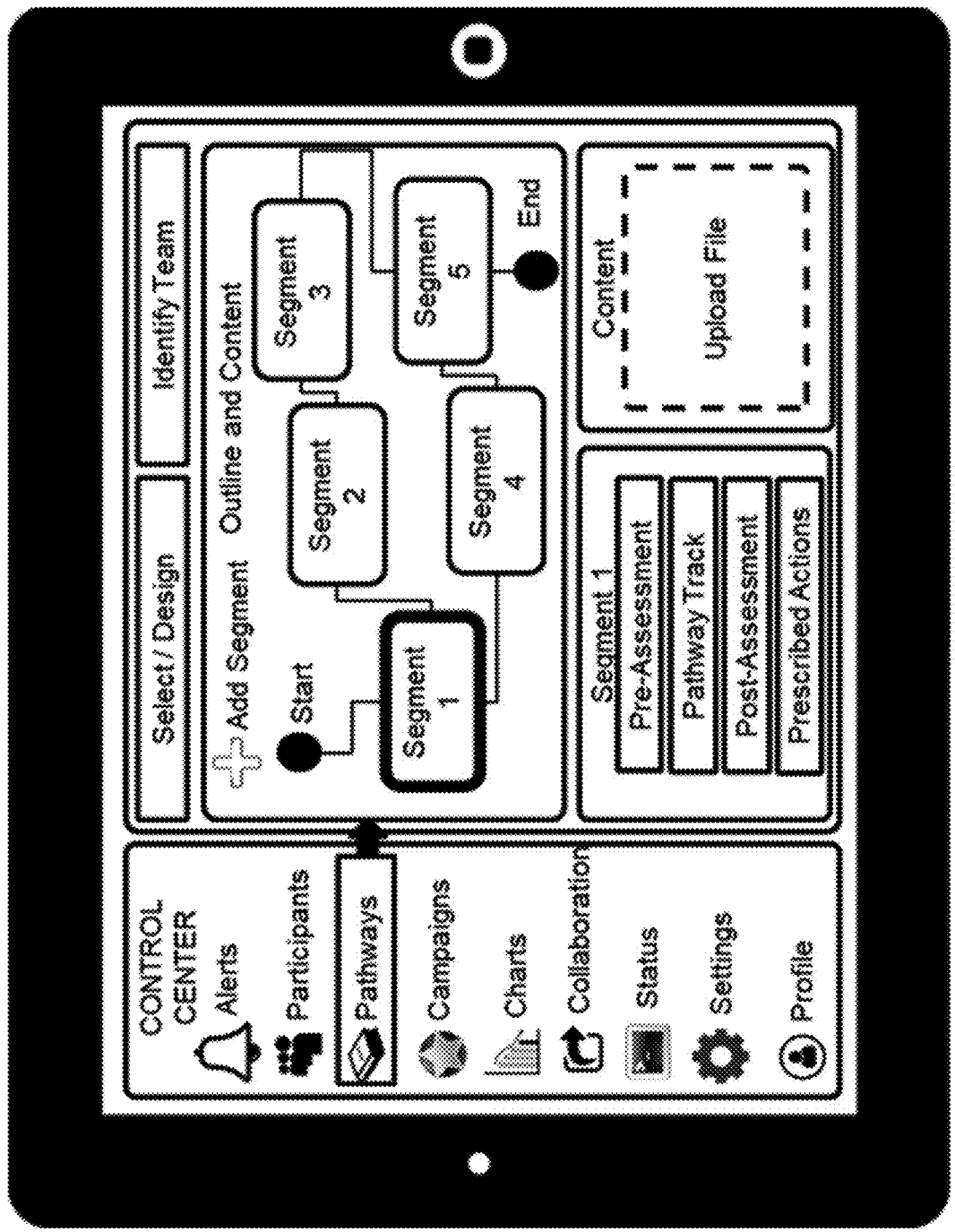

FIG. 17 shows a reconfigurable and managed system for delivering pathways to teams or groups of individuals for a given intervention. In it, the coach is able to select a predefined pathway or design a new pathway.

A pathway contains a set of segments which can be visually created through a start and end sequence. Some segments can be placed in sequence while others can be done in parallel. This allows the coach to determine the pre-requisites and allow some segments to be taken with flexibility to the individual and their desired order.

Some segments may be longer than others and based on time available an individual may want to complete an alternative segment in the meantime. A segment is utilized as component within the pathway. There can be pathways for disease management, research studies and sub-studies, health and wellness management and education, quality of care initiatives and precision health, and life event experience and exposures. The foundation is the view that segments/components must be incorporated into a comprehensive outcome defined in the pathway. As an example, a correct diagnosis alone is not sufficient, since verifying the right treatment and management, right person and at the right (correct) time are also important factors.

Each segment when defined allows the coach to upload a series of files in order to easily configure the system in how it relates data to the individual. These files include:

Pre-Assessment—a table that can describe with additional resource files the sources of data, their relationship to varying micro-cultures of meaning, and the weighting or score to be tallied.

Pathway Track—a relationship description such as a JSON message that describes scoring and customized linkage to resource, URLs, training videos, audio tracks, digital media and content management system for the given segment materials and content Post-Assessment—a table that describes queries as follow-up to a pathway, this may also be collected during the pathway track in case of monitoring activities and observing behaviors or physiological or environment details about the individual and then cross-relating with any prescribed surveys or notifications for follow-up Prescribed Actions—a relationship description such as a JSON message that handles the outcomes of the post-assessment with follow-up details related to the next segment or repeat of the current segment or recommendations of other clinical pathways of model of care/treatment in identifying the right level of the evaluations needed for safe care.

FIG. 18 illustrates an example of a table 1800 illustrating types of information and related scoring functions. The system manages pathways as interventions for individuals utilizing pre-assessments as information that programmatically through association and confidence scoring of the micro-cultures of meaning. The pre-assessments help identify and personalizes the pathways and return of value. Utilizing the pathways or intervention related personalized track for a given segment, these segments when stringed together creates a clinical pathway or model of care/treatment approach. Follow-up assessments are programmatically added to assess the model of care/treatment approach and determine whether the needed evaluations are followed. These 4 files are managed through the coach's interface and can be applied to the individual or group. These files are managed on the server but are locally managed by individuals on the client application to gain personalization provide through a personal network of devices (PNoD) and a personal network of records (PNoR). An example of a pre-assessment is shown in the table 1700.

Figure 19:
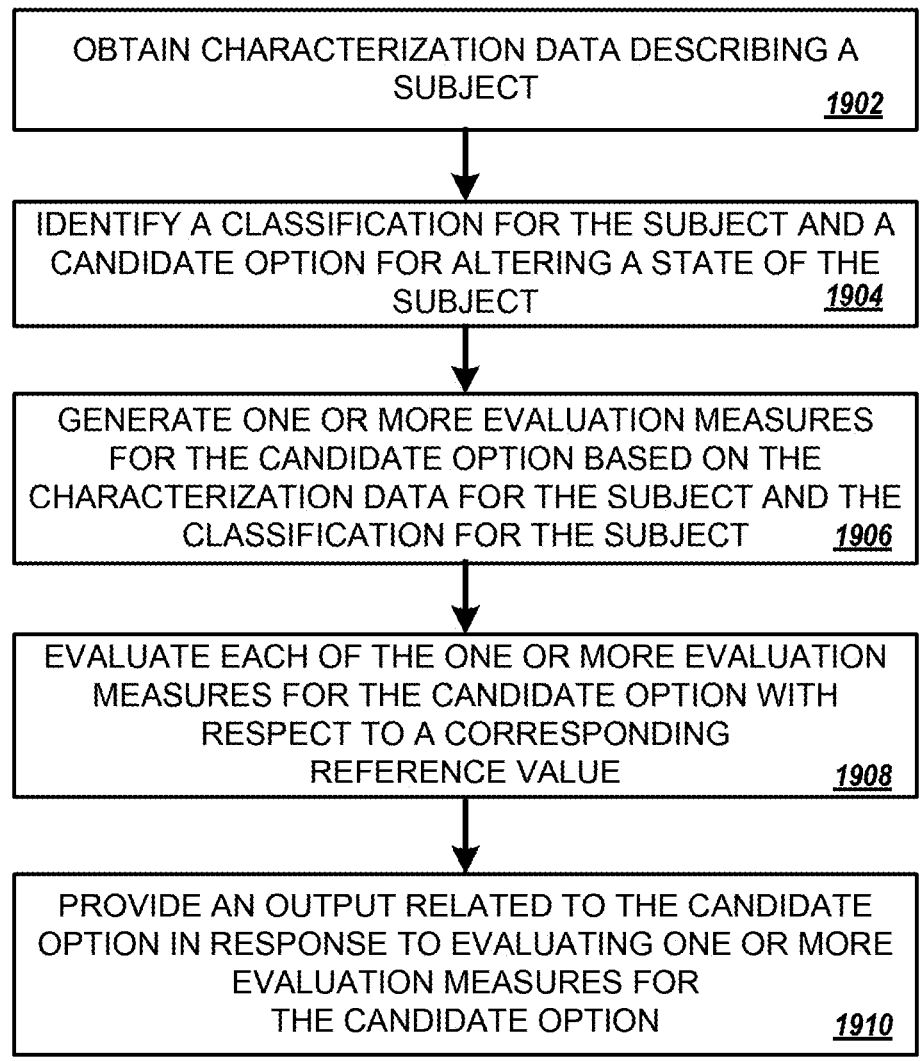
FIGS. 19 and 20 are flow diagrams illustrating examples of processes for context-based analysis to enhance computer output.

FIG. 19 is a flow diagram illustrating an example of a process 1900 for context-based analysis to enhance computer output. For example, the process 1900 can be used to ensure that an action by a computer system (e.g., a message, a recommendation, an alert, a visible or audible display of information, a change in configuration or operation, etc.) is appropriate for the current context of a subject. The process 1900 can also be used to ensure that the action provides sufficient benefit to a system, user, or other subject, e.g., will be efficient and/or effective given the context of the subject, avoids wasting resources and avoids negative or harmful effects, provides benefits that outweigh the costs and risks of the action, etc. The process 1900 can be performed by one or more computers, such as the computer system 110 discussed above.

Most computer systems and computer programs are not configured to perform the evaluation and control functions described herein. To complement and enhance other systems, the process 1900 may optionally be used to provide a check on the recommendations of other systems, e.g., as a second level of review to verify or confirm that the action proposed by another system meets a set of standards for proceeding. These can be independent, objective, and/or evidence-based standards determined from historical data compiled using many different examples involving data collected from different devices over time. In this manner, the computer system 110 can validate or certify actions that it determines to be appropriate, as well as warn about or block actions that it determines to be in appropriate (e.g., failing to meet the criteria for proceeding).

To facilitate this analysis, the computer system 110 may monitor the output or intermediate processing results of other systems, including third-party systems. For example, the computer system 110 can receive data indicating a recommendation, message, or other action proposed by a device (e.g., a server, a client device, a wearable device, a medical device, etc.) or for the device to carry out. The computer system 110 can then access related data from its databases or from databases of third party systems, for example, to obtain context data describing the current context, historical data for the subject, and so on. The computer system 110 can then use techniques of the process 1900 to determine whether to validate the proposed action and send a confirmation or instruction to allow the action to be carried out, or to decline validation and block the action (e.g., by failing to provide validation, or instructing that the action not be carried out). Thus, the computer system 110 can perform a gating function, e.g., act as a gatekeeper, to restrict actions (e.g., control functions, messages, recommendations, the display or transfer of data, etc.) of another system if the evaluation does not meet the standards enforced by the computer system 110. This function has broad application in fields such as physical security and access control, network security and data access control, customizing user interfaces, generating user interactions of artificial intelligence systems, monitoring and providing medical diagnosis and medical treatment, general management of devices and systems, and others.

The techniques can even be used to monitor and evaluate the actions of users, in order to avoid inadvertent or ill-advised actions. For example, changes initiated by a network administrator may be assessed by the computer system using the process 1900. If the network administrator initiates a change, the computer system 110 determines whether the change is appropriate given the current context of the device(s) involved in the change and for the network more generally. If the computer system 110 determines that the change is appropriate or beneficial, it can be allowed to proceed with no interruption or extra output, or an output confirming or recommending the action can be provided. If the computer system 110 determines that the change is no appropriate (e.g., not beneficial or does not outweigh risks of negative consequences), the computer system 110 can temporarily block the change and cause a warning message to be displayed, for example, asking the user to verify the change is desired, indicating that the change is not recommended and potentially indicating the scores, predicted effects, and/or systems and users likely to be adversely affected by the change. If the negative effects are determined to be of a serious type or magnitude (e.g., such as causing harm rather than mere slowdown or inefficiency), the computer system 110 may block the change without the option for the user to override, unless further authorization is provided.

In a similar manner, the techniques can be used in the medical field to avoid the issuance of, e.g., diagnoses, prognoses, prescriptions, treatments, instructions, or recommendations that are improper. Through the various factors evaluated, the computer system 110 avoid errors due to inadvertent mistakes, human biases, lack of scientific support (e.g., applying unproven techniques or techniques contrary to evidence), incorrect interpretation of the data for a patient, and so on. In some cases, a doctor or medical system may provide the correct treatment for a certain diagnosis, but the computer system 110 may detect that the diagnosis is wrong or at least not sufficiently supported by the patient data. In other cases, an action may not be the right treatment or therapy for the diagnosis. Even if the treatment is appropriate for the diagnosis in general, it may not be appropriate for the specific patient or at the specific time and context of the patient. Thus the computer system 110 can provide a valuable check to increase the likelihood that that actions that it recommends, or actions that a doctor or another system recommends, will provide safe, effective, and efficient results.

For example, machine learning systems are increasingly being used to generate diagnoses and recommend treatments, and the computer system 110 can provide a valuable check to determine whether the output of these systems is valid and appropriate for the patient (e.g., safe and effective given the user's unique combination of context, attributes, and history). For example, a machine learning system may analyze image data for a photo of a skin condition to determine a diagnosis or treatment. As another example, a machine learning model may obtain EKG data to diagnose a heart condition. As another example, a machine learning model may obtain a diagnostic imaging scan data (e.g., MRI, X-ray, CAT scan, ultrasound, etc.) to estimate or diagnose the presence of a condition (e.g., breast cancer, pneumonia, bone fracture, etc.). These systems, or doctors using the outputs of the systems, may also generate prognosis information and treatment plans (e.g., prescriptions, physical therapy, behavior changes, digital therapeutics, etc.). However, machine learning systems are not infallible and often operate on limited information in a very narrow domain. The computer system 110, on the other hand, can have access to information about the patient's history, preferences, total medical profile (e.g., not just the scan data or image data), and can assess an action (e.g., diagnosis, treatment selected, proposed treatment timing, etc.) determined by a computer system or a doctor.

Many other uses are possible, such as by hospitals, clinics, pharmacies, insurance companies, and others to analyze proposed actions or completed actions. The analysis and results can be done prospectively to verify actions before they are taken (e.g., in real time or near-real time) or retrospectively, (e.g., after actions are taken or outputs are provided). For example, the evaluation can be used to audit the performance of a device, system, organization, doctor, etc. and assess effectiveness, e.g., to determine how often the action taken or recommended meets the evidence-based standards for diagnosis, treatment selection, treatment timing, risk tolerance, and so on that the computer system 110 applies. Thus, in addition to or instead of enforcing the safety and effectiveness of actions before they are preformed, the computer system 110 may be used to audit and analyze records of previously performed actions, to determine whether and to what extent individual actions or a group of actions comply with best practices or other standards.

The process 1900 includes obtaining characterization data describing a subject (1902). The characterization data can describe, for example, attributes of the subject, activities of the subject, a context or situation of the subject, status of the subject, and so on. The characterization data may describe current information about the subject (e.g., information about the current attributes, current activities, current context, etc.), and may describe previous or former information about the subject (e.g., information about previous attributes, previous activities, previous context, etc.). The characterization data can be obtained from one or more databases, for example, a database associated with the computer system 110, a third-party database, etc. The characterization data may be derived from disparate data sources, such as EHR/EMR, user-entered or user-reported data (e.g., survey responses, interactions with prompts, user inputs, etc.), logs of actions, device configuration data, sensor data, data from a personal area network (e.g., data collected by a device, such as a phone, over a wireless connection from other nearby devices, such as wearable devices, medical treatment or monitoring devices, appliances, home automation equipment, etc.), and more.

The characterization data can include data provided by an electronic device to the one or more computers over a communication network. As discussed above, any of a diverse set of subjects can be evaluated and assessed using the techniques herein, such as a device, a system, a network, a model (e.g., a machine learning model), a hardware component, a research study, a software component, an organization, a team, an individual (e.g., a person), a combination of one or more people and equipment, and so on.

The characterization data indicated in the database can include any of various types of information that describe or characterize the state of the subject, and the attributes can be derived from many different sources. The attributes can describe, for example, physical characteristics (e.g., size, dimensions, weight, age, maintenance status, health status, physiological measures, genomics data, proteomics data, etc.) or functional characteristics (e.g., capacity, speed, efficiency, reliability, capabilities, etc.). The attributes can be self-reported by a subject, provided by a third party (e.g., an administrator, a coach, a technician, a doctor, a researcher, a supervisor, etc.), provided by one or more devices (e.g., devices used in training, tools, networking equipment, maintenance devices, medical equipment, phones, wearable devices, devices that interact with the subject or monitor the subject, etc.).

As a few examples, when the subject is a device, the characterization data can indicate attributes that are indicators of the structure and/or functional ability of the device. For example, attributes can indicate various measures of status or performance capability, such as storage capacity, processor usage, power consumption, memory usage, network bandwidth usage, network latency, response latency, throughput, error rates, and so on. Attributes can also refer to specifications or ratings of the device and its components; the make, model, or type of device; the number and types of components included in the device; hardware and/or software configuration of the device; configuration settings; and so on.

For a subject that is a person, attributes in characterization data can include vital signs or baseline indicators of health status (e.g., heart rate, respiratory rate, blood pressure, oxygen saturation, respiratory rate, respiratory effort, capillary refill time, temperature, etc.). Other attributes include height, weight, strength measurements, endurance measurements, blood chemistry measurements, genomics data (e.g., data indicating whether the subject has or lacks certain genes or certain classes of genes, indications of which form of a gene is present, etc.), proteomics data (e.g., data indicating the identification, localization, and functional characteristics of proteins of a subject). Subject attributes can include whether a person has been diagnosed with a disease or other condition (e.g., cancer, diabetes, heart disease, chronic obstructive pulmonary disease (COPD), etc.), the current status of the disease (e.g., disease stage or classification, effects or limitations due to the condition, a severity or level of progression of the disease), whether the person has received treatment and what type of treatment, and so on. Attributes may indicate the structure and/or functional capability of any structures or systems of the body. Subject attributes can include mental and psychological indicators such as anxiety levels, pain levels, scores for various personality traits, and so on. Behavioral attributes can also be indicated.

In some cases, the attributes of the characterization data indicate whether one or more markers are currently present or have been present previously for the subject. These may be for example, biomarkers, digital markers, or other types of markers.

The database can include data collected or generated for the subject over a period of time, the status data comprising information about activities or attributes of the subject at multiple points in time. Thus the characterization data can include or be based on longitudinal data, indicating trends or patterns that can be identified by the computer system 110, or indicating a sequence of events, e.g., time series data for any of the various types of information discussed herein. The computer system 110 track or monitor the activities of subjects over time and collect information obtained. For example, the computer system 110 may communicate with various other devices (e.g., phone, wearable devices, medical monitoring devices, medical treatment devices, entertainment devices, etc.) to track different aspects of an activity (e.g., type of activity, duration of the activity, intensity of the activity, results of the activity, effects of activity on the subject, etc.). Individual instances of activities may be tracked and/or composite measures of activities (e.g., frequency, average characteristics, etc.) can be tracked. Subjects can be monitored to detect changes in attributes as well.

In some implementations, the characterization data may include sensor data collected by one or more sensing devices and sent to the computer system 110, or information derived from sensor data. The sensor data may include data collected while the subject, e.g., person, is engaged in a particular activity, in particular, activities such as treatment, training activities, or assessments. The status data may include data self-reported by the subject, data collected from others, data from sensors, etc. The sensors may include one or more of, e.g., a GPS sensor, an accelerometer, a plesmography sensor, a heart rate sensor, and EKG sensor, an EEG sensor, a blood glucose sensor, an ECG sensor, a motion sensor, a pressure sensor, a temperature sensor, a blood oxygen sensor, an image sensor, an inertial sensor, etc.

In some implementations, for example, when the subject is a person, the status data may include one or more of heart rate data of the subject, oxygen saturation data of the subject, data indicating an exercise distance that the subject ran or walked, data indicating an exercise intensity that was performed by the subject, or data indicating a duration of an exercise that was performed by the subject. As discussed above, these can be current or recent values (e.g., the most recently measured) and/or prior values (e.g., a series of historical measurements taken at different times). These various data types and other may be collected using multiple sensors and/or devices.

The activities tracked by the computer system 110 can include actions that involve or are performed by the subject. Some tracked activities may be directly related to the capabilities or limitations of the subject, criteria used to classify or diagnose the subject. The context of the activities (e.g., the location, date, time day, resources allowed, whether performed alone or with another person, who supervised or instructed the activity, etc.) can be tracked and recorded as well. Some tracked activities may not be specifically related to a patient's health, diagnosis, or treatment, but nevertheless may provide information about behaviors that are indicative of relevant markers or conditions.

The computer system 110 can track attributes or activities of each of multiple subjects over a period of time, as well as changes the status of the multiple subjects over the period of time. The computer system 110 can the train models (e.g., rule-based models, machine-learning models, etc.) based on the tracked data. By tracking many variables (e.g., subject attributes, subject activities, context of the subject and activities, etc.) for many subjects and storing the data in the database, the computer system 110 can obtain a rich data set with which to discover elements that have relevance to factors evaluated by the computer system 110 (e.g., reliability, efficacy, applicability, timing, variability, and so on as discussed in FIG. 2) and the manner those factor impact outcomes. This data, whether used for machine learning training or through direct analysis and extraction of relationships by the computer system 110, can be used to identify which features are predictive of different results (e.g., whether a classification is correct, whether an action is effective with respect to a condition, whether an action is applicable for a certain combination of characterization data and/or context data, whether timing is appropriate given characterization data and/or context data, etc.) and to generate models that can be used to make predictions based on those features.

The process 1900 includes identifying a classification for the subject and a candidate option for altering a state of the subject (1904). In some implementations, the computer system 110 generates the classification and/or the candidate option based on the characterization data for the subject, context data for the subject, and or other information. For example, the computer system 110 may assess incoming data streams to classify the subject has having a failure or limitation (e.g., a malfunction of a device, a disease or health condition of a person, etc.). The computer system 110 may then use the available data to determine a set of one or more actions proposed to improve the state of the subject (e.g., to remove the malfunction of a device, to manage or treat a disease of a person, etc.). The candidate option may be one that has been selected or determined as likely to be effective (e.g., the highest-ranked or one of a set of highest-ranked options), or may simply be one of a large set of candidates that the computer system 110 will evaluate to determine which in the set may be effective.

The classification can be an indication of a condition of the subject, e.g., a current state of the subject estimated or determined based on the characterization data and/or the context data.

In some implementations, the classification for the subject and/or the candidate option for the subject are determined by another source, such as input by a user, provided by a device or system over a network, provided in a request for validation of the candidate option, accessed from a log used in an audit, etc. For example, the computer system 110 may receive data about the classification and/or candidate option in order to check or validate these data items using the characterization data, context data, and other data, which may be different from the data sets used to generate the classification and select the candidate option as a recommended set of actions. For example, the classification could be that a device is considered to be in a particular error state, and the candidate option may be a proposed action to remedy the error, provided by user input or by a machine learning system or other recommendation system. As another example, the classification could be a diagnosis that a person has a particular disease, and the candidate option could be a proposed treatment for the disease (e.g., a pharmaceutical, a behavioral therapy, a digital therapeutic, etc.).

The state of the subject can include physical state, for example, physical configuration of a device, a location or arrangement of devices or components, a physiological state of an individual, a disease state of an individual, etc. In addition, or as an alternative, the state of the subject may include a non-physical state, for example, a software state of a device, a logical state of a device, a collection of data on a memory or data storage device, a psychological or mental state of an individual, a mood of an individual, etc.

The candidate option can include one or more actions that are configured to change in the state of the subject. For example, the actions can be actions selected as likely to encourage or initiate change in the aspect of the state that led to the classification. In other words, if the classification is that a device is in an error state, the candidate option can include one or more actions that may reduce or remove the error or otherwise improve an aspect of device performance affected by the error. In the medical field, the candidate option may be a treatment option. The candidate option may include data or software to be sent, e.g., settings, instructions, software modules or other code to be run, media for presentation, etc. Even when the subject is an individual (e.g., a medical patient), the candidate option may include actions to be performed by a device associated with the individual, e.g., a medical monitoring device (e.g., a blood pressure cuff, a pulse oximeter, a scale, etc.), a medical treatment device, a user device (e.g., a phone, laptop computer, desktop computer, a wearable device, etc.), and so on. For example, the candidate option may involve sending a message (e.g., alert, notification, reminder, media, etc.) for presentation to the individual through a device or causing other interactions.

A candidate option may include one or more digital therapeutics, e.g., evidence-based therapeutic interventions driven by software programs to prevent, manage, or treat a medical disorder or disease. The interactions may be configured to change the user's behavior and may include targeted interactions that are relevant to the user's current needs or estimated future needs. Digital therapeutics can involve any of a wide range of interactions, such as providing: media; an interactive form, question, prompt, or survey; a notification; a recommendation; a reminder; an instructional activity or instructional information; a game; a test or assessment; initiating communication (e.g., a friend, family member, caregiver, doctor, emergency services, etc.); a prompt to set, adjust, or view a goal; and so on. Digital therapeutics can include interactions involving visual output, audio output, voice input, haptic output, gesture input, and other input/output modalities. The content of digital therapeutics interactions can include questions, videos, audio segments, images, instructional materials, messages (e.g., indicating encouragement, reminders, etc.), games, and other content. Similar to the way pharmaceuticals are administered at different dosages, the computer system 110 may evaluate and/or provide different dosages of digital therapeutics, e.g., through interactions of different types, frequencies, intensity, duration, etc., for research studies and/or clinical use.

Even when an individual is a subject, a candidate option may involve providing data, code, or instructions to a device, for example, to control, operate, acquire data, report data, change settings, or otherwise interact with a device. For example, the candidate option may be to cause operations by or change a configuration of a medical device, e.g., a thermometer, a blood glucose meter, a blood coagulation (PT/INR) meter, a pulse oximeter, a weight scale, a blood pressure monitor, an apnea monitor, a CPAP machine, an electrocardiogram monitor, a fetal monitor, a ventilator, a pump, a camera or other sensing device, etc.

In some implementations, the computer system 110 determines a target outcome for the state of the subject. The computer system 110 can then select the candidate option, from among multiple candidate options, based on the target outcome for the state of the subject. For example, the target outcome may be for the subject to transition from the current classification or state to a different classification or state. As another example the target outcome may be to increase the capabilities or performance of the subject, e.g., to increase a particular ability or health measure of the subject. The target outcome may be defined in terms of a desired level or range of a score, measurement, sensor observation, etc. that the subject should reach. The computer system 110 may then evaluate options in a list of potential options to identify options that are predicted likely to support, encourage, or cause the change. These can be options identified as having resulted in the target outcome or increased the likelihood of the target outcome, as determined from the aggregated outcome data and characterization data for other subjects.

The process 1900 includes generating one or more evaluation measures for the candidate option (1906). The evaluation measures can be determined based on the characterization data for the subject and the classification for the subject. The generation of the evaluation measures can take into account the subject's attributes of characteristics as well as its history. For example, for a device, the specifications of the device may provide some attributes general to all devices of the same model. In addition, attributes and context information for the specific instance of that device can be taken into account in determining evaluation measures, e.g., the current temperature, current workload, age, firmware or software version, etc. Thus, while one candidate action may be appropriate generally for one model of device in a certain state (e.g., restarting a device when an error condition occurs), the computer system 110 can determine from the characterization data and context data when the action is not appropriate for the specific device in its specific context (e.g., when the device is in critical infrastructure where restarting is not permitted, or when the current load is high enough that restarting causes too large of a disruption).

The evaluation measures can be scores for one or more different factors or dimensions of suitability of the candidate option for improving the state of the subject. One example score is a likelihood that the candidate option will improve the state of the subject (e.g., improving the health, performance, or wellbeing of the subject, potentially a likelihood of changing or stabilizing the classification for the subject). Another example score is a magnitude of effect expected for the candidate option (e.g., an amount of expected improvement in the state of the subject, according to a predetermined measurement scale). For example, the one or more evaluation measures may be evaluation scores 230 (e.g., scores 231-236) shown in FIG. 2 and discussed above. In some cases, the one or more evaluation measures may include a composite score or combined score that incorporates the contributions of multiple factors. For example, a weighted combination of the evaluation scores 231-236 may be determined.

The one or more evaluation measures can be determined by obtaining output of one or more machine learning models, where the output comprises a prediction (e.g., likelihood score, classification, probability distribution over different options, etc.) based on feature data derived from the characterization data for the subject. The one or more models can be trained based on training data indicating (i) activities or attributes of other subjects and (ii) outcomes identified for the other subjects. The one or more machine learning models can include at least one of a neural network, a support vector machine, a classifier, a regression model, a reinforcement learning model, a clustering model, a decision tree, a random forest model, a genetic algorithm, a Bayesian model, or a Gaussian mixture model.

The computer system 110 can adjust the manner of determining the evaluation scores 231-236 and/or of weighting the scores to determine a combined score based on information about other subjects having similar characterization data (e.g., similar attributes, activities, histories, contexts, etc.). For example, the data available for any individual subject may not be complete enough to assess the probability of an effect by the candidate option, as there may be different amounts of historical data and different types of data tracked for different subjects. Nevertheless, the computer system 110 can fill in the gaps in the data for a subject using aggregate information for a group or cluster of subjects identified has having similar data profiles or histories as the current subject. For example, even if an attribute is not specified for the subject, the distribution or statistical measures for the attribute can be estimated based on the values of the attribute for members of the group or cluster determined to be similar to the user.

As another example, the weights for weighting and combining contributions of different factors (e.g., different scores 231-236) may be determined based on the attributes and outcomes of other users determined to be similar (e.g., having similarity scores indicating at least a threshold level of similarity). These weights may be stored in context profile or other data for a subject, so that scoring is customized for the subject. As another example, the scoring functions themselves, e.g., algorithms, parameters, etc., for generating the scores 231-236 may be selected or modified based on the characteristics and outcomes of other subjects in a group determined to be similar to the subject. For example, for a particular context or action, the tracked outcomes for a cluster of similar subjects show a risk of occurrence or magnitude of a negative effect that is higher than typical, e.g., showing that members of the cluster have responded poorly to an intervention in the past. The scoring for a subject in that cluster may be set to provide greater weight for factor(s) related to this increased risk of a negative result or to penalize the suitability of options that relate to the action.

As another example, the computer system 110 may train and use one or more machine learning models to determine scores, and the machine learning models may be configured to generate scores in response to receiving, as input (e.g., as one of various inputs), an indication of the cluster or group to which the subject belongs. Machine learning models may be generated for different clusters, using the historical data and characterization data for the subjects in a cluster to tailor the responses of the model for the characteristics and outcomes of the set of subjects in the cluster. As a result, the computer system 110 can select the model that most closely matches the characterization data for the subject and use the selected model to make tailored predictions. In some cases, a context profile for the subject may specify one or more models to use, or data to assist in selecting which model to use, such as an indication of a cluster or group of subjects to which the subject is assigned.

The computer system 110 may obtain context data indicating a current context of the subject, with the context data indicating a current status of the subject. The context data may include sensor data from one or more sensors of the subject or a device associated with the subject. The one or more evaluation measures for the candidate option are based on the characterization data for the subject and the context data for the subject.

The process 1900 includes evaluating each of the one or more evaluation measures with respect to a corresponding reference value (1908). The computer system 110 can use reference values (e.g., thresholds, ranges, data distributions, etc.) to validate the candidate option as appropriate for the subject, given the subject's characterization data and current context. The computer system 110 can determine whether the evaluation measures satisfy corresponding thresholds, and if so, the candidate option can be validated (e.g., approved, certified, qualified, etc.) and allowed to be used (e.g., carried out, indicated to a user or system, etc.). If the evaluation measures do not satisfy corresponding thresholds, then the computer system 110 can decline validation and then block the candidate option from being used or issue a warning or other indication that the candidate option may not be appropriate.

In some implementations, the reference values may have standard or default values. For example, a minimum level of reliability may be required in a default value for in the confidence threshold 241. The computer system 110 may generate the reference values based on the aggregated data for different subjects. The reference values may be customized or personalized in some implementations. For example, the value for the confidence threshold 241 may be adjusted based on the outcomes tracked for subjects in a cluster or group of users determined to be similar to the current subject. As another example, the confidence threshold 241 may be adjusted for an individual based on the individual's characterization data and context.

The decision whether to validate the candidate option can include comparing at least one of the evaluation measures with a predetermined threshold. The decision whether to validate the candidate option may additionally or alternatively include comparing at least one of the evaluation measures with a reference value representing an evaluation measure for an alternative candidate option for altering the state of the subject. For example, the reference value may represent the score for a standard option (e.g. a default option or general best practice or standard-of-care option) or the best option identified so far (e.g., score indicating the highest suitability or match for the subject), and the computer system 110 can evaluate whether the current candidate provides a better fit (e.g., higher efficacy, greater applicability given the context, better timing, etc.) than the previously determined best option. Thus, as the computer system 110 evaluates different options the thresholds can be raised as better and better options are identified, and the computer system 110 can ultimately select the option(s) having the highest suitability indicated.

In some cases, one or more reference values may be determined using a machine learning model. For example, a machine learning system can be trained using the histories, contexts, interventions attempted, and outcomes for many different subjects, in order to learn the relationships among the data. The machine learning system can then be used to determine the thresholds that would result in different likelihoods of success, e.g., reference values which, if applied, would provide some desired success rate for the data, such as 80%, 90%, 95%, etc.

The process 1900 includes providing an output related to the candidate option in response to evaluating the one or more evaluation measures (1910). When the evaluation results in validating the candidate option for the subject (and the subject's current context), the computer system 110 can provide output enabling the candidate option to proceed. For example, the output can initiate one or actions of the candidate option. As noted above, the actions can involve sending instructions or control information to a device, changing settings or operation of a device, and so on. The actions can include providing data causing user interactions, e.g., presentation of an alert or other content on a user interface, providing interactions of digital therapeutics, and so on. As another example, the output can cause the candidate option to be stored in association with the subject. The computer system 110 or another system can store a validated option in a management plan, a treatment plan, a care plan, a list of approved actions, a schedule or calendar, etc. As another example, the output can cause a notification presenting the candidate option to be provided to a device associated with the subject. The notification can be a recommendation to carry out the candidate option. The notification can be sent by the computer system 110 over the Internet to a client device associated with the subject, such as a person's phone, an IT administrator's phone or computer, etc.

If the evaluation indicates that the candidate option is not validated, the computer system 110 does not indicate that the candidate option is approved. The computer system 110 may send data indicating that the candidate option is not approved or may request a substitute option be proposed. The computer system 110 may provide data (e.g., through an application programming interface (API), for presentation on a user interface, to a client device for presentation, etc.) that indicates a reason that the candidate option is not approved, e.g., lack of evidence to support the classification, inconsistency or failure of the data to support the classification, the timing of the candidate option is not correct, a reason the action is not suitable for the particular subject or for the current context of the subject, and so on.

The candidate option can relate to a research study. For example, the subject can be a person who is an enrolled participant in a research study or a candidate for a being included as a participant in a research study. The candidate option that the computer system evaluates and selects may be to include the subject in a cohort of the research study, include the person in a sub-study or follow-up study, disqualify or remove the person for consideration for a study, send an invitation to the study to the subject, send or initiate interactions to enroll or obtain consent of the subject for the study, etc. Other potential candidate options that can be initiated include changing the dose of a medication within the study, e.g., evaluating whether to give the subject a higher dose of the medication. Other potential candidate options include prescribing a medication, initiating a research activity, changing the inclusion criteria defining who is eligible to participate in the cohort, and so on. In addition or as an alternative, any of various clinical changes may be potential candidate options that are evaluated, validated, and then carried out or indicated by the computer system 110.

The computer system may perform the process 1900 multiple times, e.g., at different times, in response to changes in context of the subject, in response to changes in the characterization data describing the subject, for different candidate options of the same subject, for different classifications for the same subject, for different subjects, and so on. The computer system 110 may also be configured to support many subjects concurrently, running the process 1900 for different subjects in different situations.

In some implementations, the process 1900 can be used in a clinical setting. The subject can be an individual, such as a patient being evaluated by a doctor. The process 1900 can be used by the computer system 110 to consider different candidate treatment options for the patient and determine which are applicable for the patient. As another example, the process 1900 can be used to monitor input data from a doctor, computer system, etc. and validate an option (or warn about non-validated options) that is suggested for the individual.

In some implementations, the process 1900 can be used in a research setting. The subject can be an individual, such as an enrolled member of a research study or a candidate for a research study. The process 1900 can be used by the computer system 110 to consider different candidate options related to the study, e.g., whether to include the individual in the study cohort, whether to retain the individual in the study cohort, whether to increase, decrease, or maintain a medication dose as part of the study, etc.

Figure 20:
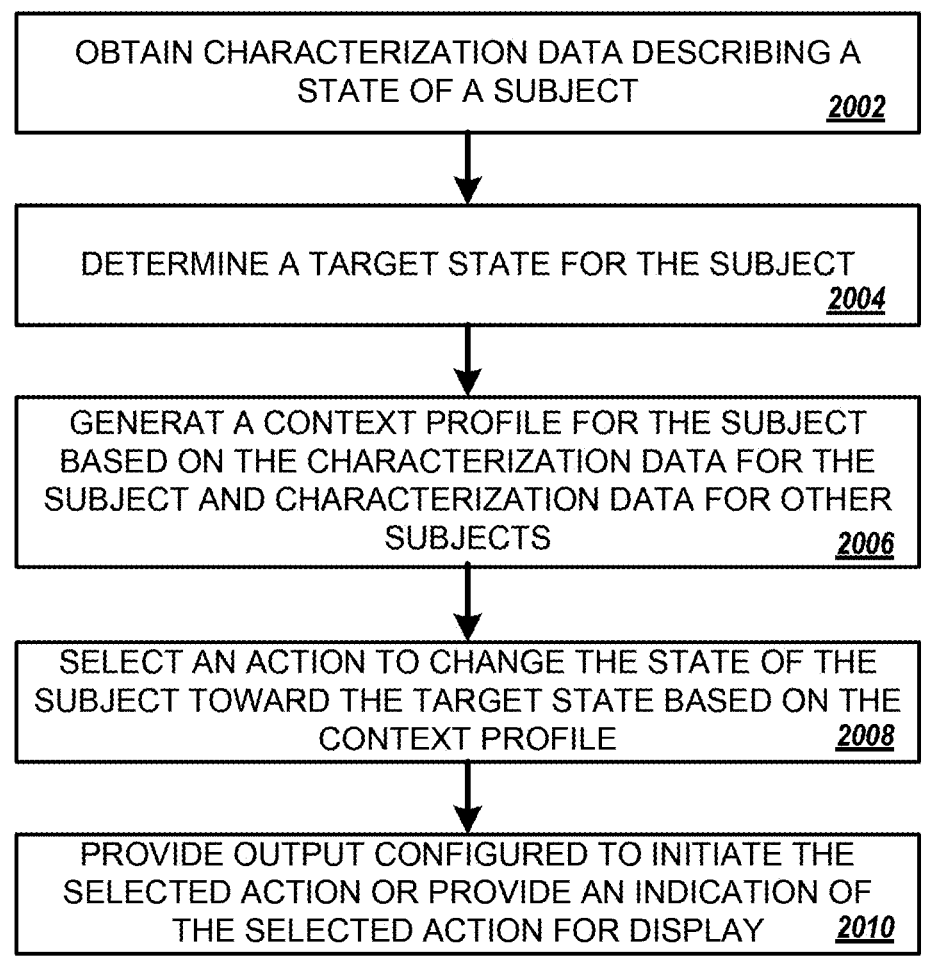

FIG. 20 is a flow diagram illustrating an example of a process 2000 for context-based analysis to enhance computer output. The process 2000 can be performed by one or more computers, such as the computer system 110 discussed above. The process 2000 can be used to select an action to change the state of a subject, e.g., to determine an action to change from a current state of the subject to a desired target state. The process 2000 can be used for many different types of subjects, as discussed above. As with the process 1900, the process 2000 may be used in a clinical setting, a research setting, etc.

The process 2000 includes obtaining characterization data describing a state of a subject (2002). The characterization data can indicate one or more physical characteristics of the subject. The characterization data can also indicate one or more non-physical characteristics of the subject, e.g., operating state, software characteristics, a person's psychological attributes or mood, etc. The characterization data and process of obtaining it can be as discussed above, for example, with respect to step 1902 of process 1900 (FIG. 19), subject data discuss for FIGS. 1A, 1B, 2, and so on. For example, the characterization data can include a combination of passively monitored user inputs, actively requested user-entered information (e.g., responses to surveys, questions, prompts, etc.), sensor data, etc.

The process 2000 includes determining a target state for the subject (2004). Achieving the target state may require a change in the state of the subject. The target state can indicate a physical characteristic for the subject to achieve, a device operating state, a psychological state or mood, a state in which the subject has a particular ability or function, etc. The target state may be defined in terms of a measurement or sensor observation indicating a value that satisfies a threshold or falls in a target range. For example, a subject that is a device may have a target state of a temperature below a threshold level, a response time of less than a threshold time, a throughput above a threshold, etc. Similarly, a subject that is a medical patient may have a target state of blood sugar in a target range, a lab result for a specimen resulting in a positive or negative result or a measurement value in a target range, a behavioral measure above or below a threshold, an exercise level above a minimum threshold, a pain level below a threshold, treating a disease (e.g., lessening or removing the disease, or reducing symptoms), maintaining a disease state (e.g., avoiding progression of the disease), preventing a disease state (e.g., maintaining health to avoid relapse or a disease the person is at risk of), etc.

Reaching the target state may involve the subject transitioning from the current classification or state to a different classification or state. As another example, the target state may be a state of increased the capabilities or performance of the subject, e.g., to increase a particular ability or health measure of the subject. The target state may be defined in terms of a desired level or range of a score, measurement, sensor observation, activity, behavior, pattern over time, combination of attributes, etc.

The process 2000 includes generating a context profile for the subject based on the characterization data for the subject and characterization data for other subjects (2006). Generating the context profile can include updating an existing context profile, e.g., a default profile or a previous context profile for the subject. The context profile can include data to customize evaluation of actions to interact with the subject. This customization can be used to affect the generation of scores for the subject and/or reference values used to compare with the scores. For example, the data can include preferences, weightings to set the relative influence or importance different factors (e.g., reliability, efficacy, applicability, timing, etc.), selection of or modifications to scoring functions for generating evaluation measures, values for scaling factors or offsets for generating evaluation measures, values for thresholds or other reference values for evaluating scores and evaluation measures, and so on. In general, the context profile can define the relevant personalized context in which actions will be evaluated.

Rather than simply representing the context of the subject, e.g., the current context data, the context profile can represent an broader interpretation of the subject's context, e.g., data generated based on the context data that specifies how the context affects scoring and evaluation and not merely what the context is. For example, the context profile can indicate not just what the subject's context is, but effects of that context on evaluation for the subject, given the outcomes observed from other subjects with the same or similar context. In other words, the context profile can specify the significance of the current context, and its effects on the selection of actions for the subject, determined according to the patterns and trends of other subjects that have experienced similar contexts.

For example, a subject's context data may include a set of sensor measurements and operating parameters for a device. The computer system 110 can identify a group of subjects that have similar attributes as the subject, and then identify a subgroup that also have had contexts, at least at one point, that have at least a minimum similarity to the subject's context (e.g., a similar pattern or combination of sensor measurements and operating parameters). Using the records for this subset, the computer system 110 can identify outcomes that occurred after this type of context occurred. For example, the records may indicate that further performance degradation is likely from the current context, and that certain options (e.g., changing a first setting) was not effective to improve performance, but that other options (e.g., changing a second setting) improved performance more than for other subjects generally. These effects may be different for the selected group or subgroup compared to the entire population of subjects of this type. In other words, by evaluating the cluster or group of subject that have similar attributes and histories, the computer system 110 can identify propensities and predictive factors that are specific to the subjects having a certain background or set of attributes. The computer system 110 can then specify the identified factors and the effects in the context profile for the user. For example, the computer system 110 can add an efficacy penalty for the change to the first setting that was not effective and add an efficacy boost for the change to the second setting that was more effective than average for subjects of this type.

To determine how the user's context affects scoring and evaluation, and thus how the context profile should be generated, the computer system 110 can evaluate the data for other subjects determined to have at least a minimum level of similarity with the current subject. The similarity analysis can be made using static attributes that do not change, attributes that may change over time, and/or dynamic aspects of context that are highly variable. Analysis of a group of similar subjects may indicate differences in the preferences and requirements of the group compared to the population at large, and those differences can be reflected in the context profile for the subject. For example, subjects having a certain set of attributes (e.g., devices having a certain configuration, role in a system, individuals having certain demographic characteristics, etc.) may be more sensitive to timing than subjects of that type generally. As a result, the context profile for a subject included in that group or cluster of subjects can indicate a weighting value for the timing factor that indicates the higher sensitivity. Similarly, the context profile may indicate a reference value, an adjustment to a reference value, a function for generating a reference value, etc. that additionally or alternatively indicates increased sensitivity to timing. This can demonstrate that, based on patterns observed for other subjects with similar backgrounds and/or context, the current subject is less able than average to tolerate inconvenient timing and so actions determined to have poor timing should be penalized more than for typical subjects. Similar analysis can be done for any or all of the factors evaluated by the computer system 110. The context profile 110 can also include data that indicates other differences from typical subjects, such as (1) negative effects (e.g., incompatibilities, contraindications, risks of harm, etc.) that are more pronounced than for typical subjects and so should be penalized, and (2) positive effects (e.g., synergies, better-than-average responses, etc.) that are more pronounced than for typical subjects and so should be boosted or rewarded in the evaluation.

In some implementations, the computer system 110 uses one or more machine learning models to generate a classification for the subject, and the classification for the subject is used to generate the context profile. For example, the computer system 110 can identify other subjects that have the same classification, and potentially other attributes in common with the subject, as the group to use in generating the context profile. In some implementations, the model is used to determine a diagnosis or classification of a health condition for an individual, then others having the same diagnosis are included in the group of similar subjects.

The machine learning model can be trained based on the characterization data of the other subjects. To generate a classification for the subject, the computer system 110 can (i) process input feature data for the subject that is derived from the characterization data for the subject using the machine learning model, and (ii) determine the classification based on output that the machine learning model provided in response to processing the input feature data for the subject. The machine learning model can include at least one of a neural network, a support vector machine, a classifier, a regression model, a reinforcement learning model, a clustering model, a decision tree, a random forest model, a genetic algorithm, a Bayesian model, or a Gaussian mixture model.

The process 2000 includes selecting an action to change the state of the subject toward the target state (2008). The action can be selected from among a plurality of candidate actions. The action can be selected based on the context profile. For example, the action can be selected using evaluation of various factors (e.g., reliability of data, expected efficacy of the action in moving the subject toward the target state, applicability of the action for the particular subject and the subject's current context, timing, etc.). The evaluation can use the context profile to generate scores or other evaluation measures and/or to determine reference values with which to compare scores.

The plurality of candidate actions can be a set of actions that correspond to a classification, current state, and/or target state of the subject. For example, if a network device is classified as having a low performance, the current state is throughput of 5 Mb and the target state is throughput of 20 Mb, the set of candidate options can be actions (e.g., changes to settings, operation, etc.) that are designated for increasing throughput or which the computer system 110 determines (e.g., based on tracked outcome data) have increased throughput for similar subjects in similar situations in the past. As another example, if a person is diagnosed with diabetes, currently has a high blood sugar level, and the target state is a blood sugar level within an acceptable range, the set of options can be diabetes treatments (including potentially subject behaviors or actions) that are have been shown to have the effect of reducing blood sugar level.

In some cases, a predetermined set of candidate actions are set for the classification of a subject, the current state of the subject, and/or the target state of the subject. For example, a given medical diagnosis or desired health outcome, there may be a predetermined set of treatment options. The computer system 110 can perform an evaluation of each of the different options and determine the subset that meet all of the evaluations the computer system 110 performs, to determine if the treatments would be safe, effective, and applicable to the subject's current context. The computer system 110 may further select one or more actions from the set of actions that are acceptable or appropriate. For example, the computer system 110 may rank the options that have at least a minimum combined score, and select the option that has the highest combined score. As another example, of the approved or validated options for a subject, the computer system 110 may then assess scores for individual factors, such as identifying an option that has the highest applicability score and is thus most suited for the particular subject, or has the highest efficacy score indicating the highest likelihood of positive effect and/or magnitude of effect, and so on. In some implementations, the computer system 110 uses the efficacy scores to determine a predicted amount of improvement toward the target state that different options may provide, e.g., based on a machine learning model output or analysis of historical tracked outcomes. The computer system 110 may select multiple actions whose predicted effects combine in expected magnitude to be able to move the subject from its current state to the target state.

The process 2000 includes providing output configured to initiate the selected action for the subject or provide an indication of the selected action for display on a user interface of a device associated with the subject (2010). In some implementations, the computer system initiates actions of the selected option directly, for example, by sending data to a device over a network, such as the Internet. For example, the computer system 110 may perform or cause another device to perform the action, by sending instructions, updated settings, data, updated software, etc. that causes a device to change its configuration or otherwise change its state. For example, when the subject is a network appliance, a selected action of restarting the device may be initiated by the computer system 110. As another example, if the subject is a person, the computer system 110 may send data causing a phone or other device of the person to initiate a digital therapeutic interaction with the person.

In some implementations, the computer system 110 sends data for presentation to a user, e.g., for sending data for display in a user interface of a client device. The indication of the selected action can include an explanation of the action selected, instructions for carrying it out, etc. For example, when the subject is a network appliance, the indication may be an indication of a step to perform, such as to restart the device, potentially with an interactive control (e.g., on-screen button, slider, etc.) that initiates restarting the device in response to user interaction with the control. As another example, for a subject that is a medical patient, the indication of the action can be a treatment action sent for presentation on a device of the patient or of medical staff.

The action that the computer system 110 selects can relate to a research study, including management and creation of a cohort to recruit for future participation in data collection, monitoring, laboratory tests, etc. For example, the subject can be a person who is an enrolled participant in a research study or a candidate for a being included as a participant in a research study. The action that the computer system evaluates and selects may be to include the subject in a cohort of the research study, include the person in a sub-study or follow-up study, disqualify or remove the person for consideration for a study, send an invitation to the study to the subject, send or initiate interactions to enroll or obtain consent of the subject for the study, etc. Other potential actions that can be initiated include changing the dose of a medication within the study, e.g., evaluating whether to give the subject a higher dose of the medication. Other potential actions include prescribing a medication, initiating a research activity, changing the inclusion criteria defining who is eligible to participate in the cohort, and so on. In addition or as an alternative, any of various clinical changes may be potential actions that are evaluated, validated, and then carried out or indicated by the computer system 110.

As discussed above for FIGS. 1A and 1B, the computer system 110 can evaluate any of various types of outputs to or about the subject. These outputs can be related to the subject's context, the target state for the subject, the selected action, and so on. For example, the computer system 110 may provide text, graphics, media or other elements to explain the selected action, identify actions not selected and indicate a reason they were not selected (e.g., for inappropriate timing, for not being appropriate for the subject's context, etc.). In general, any of the subject characterization data, context data, or context profile used to select the action or indicate that an action is not selected can be provided. Nevertheless, the computer system 110 can evaluate the relevance and potential benefit of providing the information to selectively provide outputs that are appropriate.

In some implementations, the computer system 110 enhances information delivery by selectively providing data and interactive elements. For example, the computer system 110 can obtain characterization data describing a subject and context data indicating a context of the subject. The computer system 110 can access a data package comprising data for delivery to the subject. This data package may be assembled by the computer system 110 or by another system. The data package may include results for a cohort of a research study of which the subject is a participant. The data package may additionally or alternatively include individual results (e.g., personal clinical data) for the subject.

The computer system 110 can identify one or more actions corresponding to the data for delivery based on at least one of the characterization data and the context data. The one or more actions may be a recommendation determined to be relevant to the subject based on the subject's data and context. The computer system 110 can provide to a device associated with the subject, user interface data for a user interface configured to present (i) at least portions of the data for delivery that have been selected based on the context data for the subject and (ii) one or more interactive user interface controls corresponding to the identified one or more actions. In some implementations, the user interface controls enable a user to initiate an action (e.g., change sensor data collection, change monitoring and reporting of data, initiate a call or other communication, etc.), save the one or more actions (e.g., add them to a management plan, a care plan, etc.) plan, add the actions to a schedule, etc.

In some implementations, identifying the one or more actions is based on output generated using a machine learning model in response to receiving input data derived from at least one of the characterization data and the context data.

The data collected by the computer system 110 (e.g., as subject data, context data, outcome data, etc.) and used in any of the examples and implementations discussed above can include a variety of information from a variety of sources. Data can be collected for categories representing a variety of individual, community, or public health conditions and behaviors. This data can include attributes that are biological, physical or physiological, mental, emotional, environmental, or social. The collected data can include biological attributes, such as genetic makeup, genomics, family history, sensory abilities (e.g., ability to see, perception of light and dark, perception of color, extent of ability to smell, ability to touch and sensitivity, ability to hear and sensitivity, etc.). These may reflect biological factors that a person cannot control. The collected data can include physical or physiological attributes, e.g., weight, muscle mass, heart rate, sleep, nutrition, exercise, lung capacity, brain activity, etc. Some physical attributes may result from the impact of lifestyle choices or things that a person can control. The collected data can include mental attributes, such as interpretation of brain related signals, indications of chemical imbalances, education levels, results of mental tests, etc. The collected data can include emotional attributes, such as interpretation of self-reported data, or classified audio or video related data that suggests individual responses to stimuli. The collected data can include environmental data, such as location data, air quality, audible noise, visual noise, temperature, humidity, movement (and potentially effects of movement such as motion sickness, etc. The collected data can include social attributes, such as whether a subject is socially engaged, exhibits social avoidance, experiences the impact of acceptance or responsiveness emotionally, and so on.

The data collected and used by the computer system 110 (e.g., to generate feature values, to train models, to validate and select actions, etc.) can include various other types of data including:

- Lab and diagnostic data (e.g., assay data, blood test results, tissue sample results, endocrine panel results);
- Omics data (e.g., data relating to genomics, proteomics, pharmacogenomics, epigenomics, metabolomics, biointeractomics, interactomics, lifeomics, calciomics, chemogenomics, foodomics, lipidomics, metabolomics, bionomics, econogenomics, connectomics, culturomics, cytogenomics, fermentanomics, fluxomics, metagenomics, metabonomics, metallomics, O-glcNAcomics, glycomics, glycoproteomics, glycosaminoglycanomics, immunoproteomics, ionomics, materiomics, metalloproteomics, metaproteogenomics, metaproteomics, metatranscriptomics, metronomics, microbiomics, microeconomics, microgenomics, microproteomics, miRomics, mitogenomics, mitoproteomics, mobilomics, morphomics, nanoproteomics, neuroeconomics, neurogenomics, neuromics, neuropeptidomics, neuroproteomics, nitroproteomics, nutrigenomics, nutrimetabonomics, oncogenomics, orthoproteomics, pangenomics, peptidomics, pharmacoeconomics, pharmacometabolomics, pharmacoproteomics, pharmaeconomics, phenomics, phospholipidomics, phosphoproteomics, phylogenomics, phylotranscriptomics, phytomics, postgenomics, proteogenomics, proteomics, radiogenomics, rehabilomics, retrophylogenomics, secretomics, surfaceomics, surfomics, toxicogenomics, toxicometabolomics, toxicoproteomics, transcriptomics, vaccinomics, variomics, venomics, antivenomics, agrigenomics, aquaphotomics);
- Biologically sampled data (e.g., data describing blood, urine, saliva, breath sample, skin scrape, hormone levels, ketones, glucose levels, breathalyzer, DNA, perspiration, and other biological samples and derived data);
- Cardiac-related biodata (e.g., data from ECG/EKG monitors, heart rate monitors, blood pressure monitors);
- Respiratory-related biodata (e.g. data from spirometers, pulse oximeters);
- Neurological-related biodata (e.g. data from EEG monitors);
- Behavior data (e.g. movement patterns, gait, social avoidance);
- Drug data (e.g., prescription information, pharmacological data);
- Substance use data (e.g., alcohol, medication, insulin, recreational drugs, tobacco);
- Sleep data (e.g., motion data, heart rate data, body temperature, perspiration, breathing data, ambient light, ambient sound, ambient temperature);
- Exercise data (e.g. performance data, distance covered, activity, VO2 Max),
- Physical activity data (e.g., step counts, heart rate, flights climbed, altitude, other data from fitness trackers);
- Mood data (e.g., happiness, depression, PHQ9, BMIS data and other scales/reporting mechanism);
- Positioning and location data (e.g., GPS data, gyroscope, altimeter, accelerometer, linear acceleration, received signal strength indicator from nearby emitters such as WiFi access points, Bluetooth sensors and sensor networks and Cellular towers);
- Environmental data (e.g., air quality data, ozone data, weather data, water-quality data, audible decibel levels, interpreting measured audio data, measuring luminance lux, interpreting measured light wavelengths, measuring temperature and gases or particles—such as formaldehyde (Molecular Formula: $H_2CO$ or $CH_2O$); alcohol vapor (Molecular Formula: hydroxyl group-OH, e.g., Isopropyl$C_3H_8O$ or $C_3H_7OH$, as well as Ethanol: $C_2H_6O$ or $C_2H_5OH$); benzene ($C_6H_6$); Hexane ($C_6H_{14}$); Liquefied Petroleum Gas (LPG) which could include a mixture of butane (Molecular Formula: $CH_3CH_2CH_2CH_3$ or $C_4H_{10}$) and isobutene (Molecular Formula: $(CH_3)_2CHCH_3$ or $C_4H_{10}$ or $(CHC_4H_{10})_2CHCH_3$); propane (Molecular Formula: $CH_3CH_2CH_3$ or $C_3H_8$); natural coal or town gas which could include of methane or natural gas (Molecular Formula: $CH_4$); carbon dioxide (Molecular Formula: $CO_2$); hydrogen (Molecular Formula: $H_2$); carbon monoxide or possibly smoke (Molecular Formula: CO); and oxygen (Molecular Formula: $O_2$) in the environment surrounding an individual inside and outside the contextual location of the potential subjects such as home, office, and including vehicle data— such as speed, location, amount of time driving, mood while driving, environmental data in the car).

A number of implementations have been described. Nevertheless, it will be understood that various modifications may be made without departing from the spirit and scope of the disclosure. For example, various forms of the flows shown above may be used, with steps re-ordered, added, or removed.

Embodiments of the invention and all of the functional operations described in this specification can be implemented in digital electronic circuitry, or in computer software, firmware, or hardware, including the structures disclosed in this specification and their structural equivalents, or in combinations of one or more of them. Embodiments of the invention can be implemented as one or more computer program products, e.g., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a tablet computer, a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the invention can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments of the invention can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the invention, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

In each instance where an HTML file is mentioned, other file types or formats may be substituted. For instance, an HTML file may be replaced by an XML, JSON, plain text, or other type of files. Moreover, where a table or hash table is mentioned, other data structures (such as spreadsheets, relational databases, or structured files) may be used.

Particular embodiments of the invention have been described. Other embodiments are within the scope of the following claims. For example, the steps recited in the claims can be performed in a different order and still achieve desirable results.

What is claimed is:

1. A method performed by one or more computers, the method comprising:
   obtaining, by the one or more computers, characterization data describing a subject, wherein the characterization data comprises data indicating one or more physical characteristics of the subject obtained from data stored in a database;
   identifying, by the one or more computers, a classification for the subject and multiple candidate options for altering a state of the subject;
   generating, by the one or more computers, a set of one or more evaluation measures for each of the multiple candidate options for altering the state of the subject, the one or more evaluation measures being based on output generated by one or more models based on feature data derived from the characterization data for the subject, wherein the one or more models have been trained based on training data indicating (i) activities or attributes of other subjects and (ii) outcomes identified for the other subjects, and wherein each set of one or more evaluation measures indicates a level of appropriateness of the corresponding candidate option for the subject that has the identified classification and the one or more physical characteristics;

selecting, by the one or more computers, a candidate option from among the multiple candidate options based on assessment of the evaluation measures by the one or more computers, the selected candidate option being one of a plurality of the multiple candidate options that are applicable for the classification;

validating, by the one or more computers, that the selected candidate option is appropriate for the subject based on determining that each of the one or more evaluation measures for the selected candidate option satisfies a condition with respect to a corresponding reference value; and in response to validating that the selected candidate option is appropriate for the subject, providing, by the one or more computers, output to cause at least one of initiating one or more actions of the selected candidate option, storing data indicating the selected candidate option in association with the subject, or causing a notification presenting the selected candidate option to be provided to a device associated with the subject.

2. The method of claim 1, wherein the method includes obtaining context data indicating a current context of the subject, the context data indicating a current status of the subject, wherein the context data comprises sensor data from one or more sensors of the subject or a device associated with the subject; and wherein the one or more evaluation measures for each of the candidate options are based on the characterization data for the subject and the context data for the subject.

3. The method of claim 1, wherein validating that the candidate option is appropriate comprises at least one of:

comparing at least one of the evaluation measures for the selected candidate option with a predetermined threshold; or comparing at least one of the evaluation measures for the selected candidate option with a reference value representing an evaluation measure for an alternative candidate option for altering the state of the subject.

4. The method of claim 1, wherein the subject is a device, a system, a network, a model, a hardware component, a software module, an individual, a group of people, or an organization.

5. The method of claim 1, where obtaining the characterization data comprises obtaining information generated based on sensor data from one or more sensors.

6. The method of claim 1, wherein the method comprises:

generating the reference value corresponding to at least one evaluation measure using a machine learning model.

7. The method of claim 1, wherein generating the evaluation measures comprises generating an efficacy score for each of the candidate options, wherein the efficacy score is indicative of predicted results of carrying out the corresponding candidate option for the subject based at least on the one or more physical characteristics of the subject obtained from data stored in a database.

8. The method of claim 7, wherein generating the efficacy score for each of the candidate options comprises:

providing feature data derived from the characterization data for the subject and context data for the subject to a trained machine learning model that has been trained based on example data sets including (i) characterization data for other subjects, and (ii) context data for the other subjects, and (iii) outcomes of performing the candidate option for at least some of the other subjects; and generating the efficacy score based on output that the trained machine learning model generated by processing the feature data.

9. The method of claim 1, comprising receiving context data indicating a context of the subject, wherein generating the evaluation measures comprises generating, for each of the candidate options, a customization score indicating a level of applicability of the candidate option for the subject, the customization score being generated based on the context data.

10. The method of claim 1, wherein generating the evaluation measures comprises generating, for each of the candidate options, a timing score indicating an appropriateness of the candidate option for the subject, wherein the timing score is based on (i) historical data for the subject and (ii) context data for the subject.

11. The method of claim 1, wherein generating the one or more evaluation measures comprises generating, for each of the candidate options, a variability score indicating a level of variation among results of implementing the candidate option for other subjects.

12. The method of claim 1, wherein generating the evaluation measures comprises generating, for each of the candidate options, one or more scores that quantify potential risks of harm to the subject that may result from performing the candidate option.

13. The method of claim 1, comprising determining a target outcome for the state of the subject; and selecting the candidate option, from among multiple candidate options, based on the target outcome for the state of the subject.

14. The method of claim 1, comprising clustering a plurality of subjects into clusters based on similarities among physical characteristics of the plurality of subjects; and identifying, from among the clusters of subjects, a cluster for the subject;

wherein generating the one or more evaluation measures is based on the identified cluster for the subject.

15. The method of claim 1, wherein the classification of the subject is a classification of a health status of a user of a device.

16. The method of claim 1, wherein the classification is a disease diagnosis, the multiple candidate options comprise multiple potential treatments for the disease, and the selected candidate option is one of the multiple potential treatments for the disease.

17. The method of claim 1, wherein the one or more models comprise one or more neural networks.

18. A system comprising:

one or more computers; and one or more computer-readable media storing instructions that, when executed by the one or more computers, cause the one or more computers to perform operations comprising:

obtaining, by the one or more computers, characterization data describing a subject, wherein the characterization data comprises data indicating one or more physical characteristics of the subject determined from data stored in a database;

identifying, by the one or more computers, (i) a classification of a current state of the subject that indicates an impairment of the subject and (ii) multiple candidate options for altering the current state of the subject;

generating, by the one or more computers, a set of one or more evaluation measures for each of the multiple candidate options for altering the state of the subject, the one or more evaluation measures being based on output generated by one or more models based on feature data derived from the characterization data for the subject, wherein the one or more models have been trained based on training data indicating (i) activities or attributes of other subjects and (ii) outcomes identified for the other subjects;

selecting, by the one or more computers, a candidate option from among the multiple candidate options based on assessment of the evaluation measures by the one or more computers, wherein the selecting includes ranking the multiple candidate options based on the one or more evaluation measures for the respective candidate options and selecting the candidate option based on the ranking, the selected candidate option being one of a plurality of the multiple candidate options that are capable of reducing or removing the impairment;

validating, by the one or more computers, that the selected candidate option is appropriate for the subject based on evaluating each of the one or more evaluation measures for the selected candidate option with respect to a corresponding reference value; and in response to validating that the selected candidate option is appropriate for the subject, providing, by the one or more computers, output to cause at least one of initiating one or more actions of the selected candidate option, storing data indicating the selected candidate option in association with the subject, or causing a notification presenting the selected candidate option to be provided to a device associated with the subject.

19. The system of claim 18, wherein each set of one or more evaluation measures for includes an efficacy score indicating (i) an estimated likelihood that the corresponding candidate option will reduce the impairment or (ii) an estimated level of effect of the corresponding candidate option in reducing the impairment; and wherein the selected candidate option is selected based at least in part on the corresponding efficacy score.

20. One or more non-transitory computer-readable media storing instructions that, when executed by the one or more computers, cause the one or more computers to perform operations comprising:

obtaining, by the one or more computers, characterization data describing a subject, wherein the characterization data comprises data indicating one or more physical characteristics of the subject determined from data stored in a database;

identifying, by the one or more computers, (i) a classification for the subject that indicates impaired function of the subject and (ii) multiple candidate options for altering a state of the subject;

generating, by the one or more computers, a set of evaluation measures for each of the multiple candidate options for altering the state of the subject, wherein each set of one or more evaluation measures is generated based on the characterization data for the subject and the classification for the subject, and wherein each set of one or more evaluation measures includes an efficacy score that quantifies an estimated ability of the candidate option to improve function of the subject, wherein the efficacy scores are determined based expected magnitudes of improvement determined from outcomes observed in a cluster of subjects that includes the subject and is determined based on similarity among physical characteristics of the subjects in the cluster;

selecting, by the one or more computers, a candidate option from among the multiple candidate options based on assessment of the evaluation measures by the one or more computers, the selected candidate option being one of a plurality of the multiple candidate options that are applicable for the classification;

validating, by the one or more computers, that the selected candidate option is appropriate for a current context of the subject and a history of the subject; and in response to validating that the selected candidate option is appropriate for the subject, providing, by the one or more computers, output to cause at least one of initiating one or more actions of the selected candidate option, storing data indicating the selected candidate option in association with the subject, or causing a notification presenting the selected candidate option to be provided to a device associated with the subject.

21. The one or more non-transitory computer-readable media of claim 20, comprising determining a reliability score indicating a level of confidence in the accuracy of the classification for the subject;

wherein validating the selected candidate action is based on determining that the reliability score satisfies a threshold.

22. The one or more non-transitory computer-readable media of claim 20, comprising determining a reliability score indicating a level of consistency among data collected regarding the subject;

wherein validating the selected candidate action is based on determining that the reliability score satisfies a threshold.

23. A method performed by one or more computers, the method comprising:

obtaining, by the one or more computers, characterization data describing a subject, wherein the characterization data comprises data indicating one or more physical characteristics of the subject determined from data stored in a database;

identifying, by the one or more computers, (i) a classification of a current state of the subject that indicates an impairment of the subject and (ii) multiple candidate options for altering the current state of the subject;

generating, by the one or more computers, a set of one or more evaluation measures for each of the multiple candidate options for altering the state of the subject, the one or more evaluation measures being based on output generated by one or more models based on feature data derived from the characterization data for the subject, wherein the one or more models have been trained based on training data indicating (i) activities or attributes of other subjects and (ii) outcomes identified for the other subjects;

selecting, by the one or more computers, a candidate option from among the multiple candidate options based on assessment of the evaluation measures by the one or more computers, wherein the selecting includes ranking the multiple candidate options based on the one or more evaluation measures for the respective candidate options and selecting the candidate option based on the ranking, the selected candidate option being one of a plurality of the multiple candidate options that are capable of reducing or removing the impairment;

validating, by the one or more computers, that the selected candidate option is appropriate for the subject based on evaluating each of the one or more evaluation measures for the selected candidate option with respect to a corresponding reference value; and in response to validating that the selected candidate option is appropriate for the subject, providing, by the one or more computers, output to cause at least one of initiating one or more actions of the selected candidate option, storing data indicating the selected candidate option in association with the subject, or causing a notification presenting the selected candidate option to be provided to a device associated with the subject.

24. A method performed by one or more computers, the method comprising:

obtaining, by the one or more computers, characterization data describing a subject, wherein the characterization data comprises data indicating one or more physical characteristics of the subject determined from data stored in a database;

identifying, by the one or more computers, (i) a classification for the subject that indicates impaired function of the subject and (ii) multiple candidate options for altering a state of the subject;

generating, by the one or more computers, a set of evaluation measures for each of the multiple candidate options for altering the state of the subject, wherein each set of one or more evaluation measures is generated based on the characterization data for the subject and the classification for the subject, and wherein each set of one or more evaluation measures includes an efficacy score that quantifies an estimated ability of the candidate option to improve function of the subject, wherein the efficacy scores are determined based expected magnitudes of improvement determined from outcomes observed in a cluster of subjects that includes the subject and is determined based on similarity among physical characteristics of the subjects in the cluster;

selecting, by the one or more computers, a candidate option from among the multiple candidate options based on assessment of the evaluation measures by the one or more computers, the selected candidate option being one of a plurality of the multiple candidate options that are applicable for the classification;

validating, by the one or more computers, that the selected candidate option is appropriate for a current context of the subject and a history of the subject; and in response to validating that the selected candidate option is appropriate for the subject, providing, by the one or more computers, output to cause at least one of initiating one or more actions of the selected candidate option, storing data indicating the selected candidate option in association with the subject, or causing a notification presenting the selected candidate option to be provided to a device associated with the subject.

* * * * *

UNITED STATES PATENT AND TRADEMARK OFFICE
CERTIFICATE OF CORRECTION

PATENT NO. : 11,102,304 B1
APPLICATION NO. : 16/881081
DATED : August 24, 2021
INVENTOR(S) : Praduman Jain, James Clive Wade and Josh Schilling It is certified that error appears in the above-identified patent and that said Letters Patent is hereby corrected as shown below:

In the Claims

In Claim 19, Column 69, Line 46, delete "measures for includes" and insert -- measures includes --, therefor.

Signed and Sealed this
Twenty-third Day of November, 2021

Drew Hirshfeld
*Performing the Functions and Duties of the
Under Secretary of Commerce for Intellectual Property and
Director of the United States Patent and Trademark Office*